(12) United States Patent
Kondejewski et al.

(10) Patent No.: US 6,358,921 B1
(45) Date of Patent: Mar. 19, 2002

(54) ANTIMICROBIAL PEPTIDE COMPOSITIONS AND METHOD

(75) Inventors: Leslie H. Kondejewski; Robert S. Hodges; David S. Wishart, all of Edmonton; Robert E. W. Hancock, Vancouver; Ronald N. McElhaney, Edmonton; Elmar J. Prenner, Edmonton; Ruthven N. A. H. Lewis, Edmonton, all of (CA)

(73) Assignee: Pence, Inc., Edmonton (CA)

( * ) Notice: Subject to any disclaimer, the term of this patent is extended or adjusted under 35 U.S.C. 154(b) by 0 days.

(21) Appl. No.: 08/949,059

(22) Filed: Oct. 10, 1997

Related U.S. Application Data

(60) Provisional application No. 60/028,315, filed on Oct. 11, 1996.

(51) Int. Cl.$^7$ .............................................. A61K 38/12
(52) U.S. Cl. ..................... 514/11; 530/317; 530/318
(58) Field of Search ................................ 530/317, 318; 514/11

(56) References Cited

U.S. PATENT DOCUMENTS 5,602,097 A * 2/1997 Edwards ...................... 514/17

OTHER PUBLICATIONS

Kondejewski et al. Design, Synthesis and Characterization of a peptide B–Sheet Model, Peptides: Chemistry, Structure and Biology, Ed. Pranin et al. Scientific Ltd. pp. 68–70, 1996.*

Katsu et al. Mode of Action of the Gramicidin S Analogs Lacking Hydrophobic Amino Acid Residues on Biomembranes, Chem. Pharm. Bull. 38(10) 2280–2881 (1990).*

Altmann and Mutter, "A General Strategy for the De Novo Design of Proteins—Template Assembled Synthetic Proteins," *Int. J. Biochem.* 22(9):947–956, 1990.

Angus et al., "Mapping and Characterization of Two Mutations to Antibiotic Supersusceptibility in *Pseudomonas aeruginosa*," *J. of General Microbiology* 133:2905–2914, 1987.

Braunschweiler and Ernst, "Coherence Transfer by Isotropic Mixing: Application to Proton Correlation Spectroscopy," *J. of Magnetic Resonance* 53:521–528, 1983.

Clark, "Novel Antibiotic Hypersensitive Mutants of *Escherichia coli* Genetic Mapping and Chemical Characterization," *FEMS Microbiology Letters* 21:189–195, 1984.

Creighton, *Proteins: Structures and Molecular Principles*, W. H. Freeman and Company, New York, 1983.

Erickson and Merrifield, *The Proteins*, vol. II, Neurath and Hill eds., Academic Press, New York, 1976, Chapter 3, "Solid–Phase Peptide Synthesis," 255–527.

Guo et al., "Prediction of Peptide Retention Times in Reversed–Phase High–Performance Liquid Chromatography," *J. of Chromatography* 359:499–517, 1986.

Hancock and Wong, "Compounds Which Increase the Permeability of the *Pseudomonas aeruginosa* Outer Membrane," *Antimicrobial Agents and Chemotherapy* 26(1):48–52, 1984.

Hancock, "Aminoglycoside Uptake and Mode of Action—With Special Reference to Streptomycin and Gentamincin: Effects of Aminoglycosides on Cells," *J. of Antimicrobial Chemotherapy* 8:429–445, 1981.

Hull et al., "The Crystal Structure of a Hydrated Gramicidin S–Urea Complex," *Nature* 275:206–207, 1978.

Izumiya et al., *Synthetic Aspects of Biologically Active Cyclic Peptides: Gramicidin S and Tyrocidines*, Kodansha Ltd., Tokyo; Halsted Press, New York, 1979, 49–89.

Kitagawa et al., "Convenient One–Pot Method for Formylation of Amines and Alcohols Using Formic Acid and 1,1'–Oxalyldiimidazole," *Chem. Pharm. Bull.* 42(8):1655–1657, 1994.

Klostermeyer, "Synthese von Gramicidin S mit Hilfe der Merrifield–Methode," *Chem. Ber.* 101:2823–2831, 1968 (+English Summary).

Krause et al., "Conformation of a Water–Soluble β–Sheet Model Peptide," *Int. J. Peptide Protein Res.* 48:559–568, 1996.

Kreiswirth et al., "The Toxic Shock Syndrome Exotoxin Structural Gene is Not Detectably Transmitted by a Prophage," *Nature* 305:709–712, 1983.

Kumar et al., "A Two–Dimensional Nuclear Overhauser Enhancement (2D NOE) Experiment for the Elucidation of Complete Proton–Proton Cross–Relaxation Networks in Biological Macromolecules," *Biochemical and Biophysical Research Communications* 95(1):1–6, 1980.

Loh et al., "Use of the Fluorescent Probe 1–N–Phenylnapthylamine to Study the Interactions of Aminoglycoside Antibiotics with the Outer Membrane of *Pseudomonas aeruginosa*," *Antimicrobial Agents and Chemotherapy* 26(4):546–551, 1984.

Losse and Neubert, "Synthese Von Gramicidin S Durch Neue Varianten Der Festphasensynthese," *Tetrahedron Letters* 15:1267–1270, 1970 (+English Summary).

Maeda et al., "Purification and Characterization of a New Metal Protease Which Hydrolyzes the Cyclic Decapeptide, Gramicidin S," *J. of Fermentation and Bioengineering* 75(3):173–177, 1993.

(List continued on next page.)

*Primary Examiner*—F. T. Moezie
(74) *Attorney, Agent, or Firm*—SEED Intellectual Property Law Group PLLC

(57) ABSTRACT

The invention concerns antimicrobial cyclic peptides and peptide analogs having relatively low hemolytic activity. Peptides of the invention are effective in killing and/or inhibiting growth of a number of microorganisms, including gram-positive bacteria, gram-negative bacteria, fungi and mycoplasma. Also disclosed are methods for inhibiting or killing such microorganisms, and therapeutic preparations for such inhibiting or killing.

11 Claims, 21 Drawing Sheets

OTHER PUBLICATIONS

Moore et al., "Interaction of Polycationic Antibiotics with *Pseudomonas aeruginosa* Lipopolysaccharide and Lipid A Studied by Using Dansyl–Polymyxin," *Antimicrobial Agents and Chemotherapy* 29(3), 496–500, 1986.

Neu, "The Crisis in Antibiotic Resistance," *Science* 257:1064–1073, 1992.

Parker et al., "New Hydrophilicity Scale Derived from High–Performance Liquid Chromatography Peptide Retention Data: Correlation of Predicted Surface Residues with Antigenicity and X–ray–Derived Accessible Sites," *Biochemistry* 25:5425–5432, 1986.

Peterson et al., "Decrease Binding of Antibiotics to Lipopolysaccharides from Polymyxin–Resistant Strains of *Escherichia coli* and *Salmonella typhimurium*," *Antimicrobial Agents and Chemotherapy* 31(2):230–237, 1987.

Piantini et al., "Multiple Quantum Filters for Elucidating NMR Coupling Networks," *J. Am. Chem. Soc.* 104:6800–6801, 1982.

Rackovsky and Scheraga, "Intermolecular Anti–Parallel β Sheet: Comparison of Predicted and Observed Conformations of Gramicidin S," *Proc. Natl. Acad. Sci.* 77(12):6965–6967 1980.

Rothemund et al., "Peptide Destabilization by Two Adjacent D–Amino Acids in Single–Stranded Amphipathic α–Helices," *Peptide Research* 9:79–87, 1996.

Sato et al., "Studies of Peptide Antibiotics. XXXV. Synthesis of Gramicidin S by a Fragment Solid–Phase Method," *Bulletin of the Chemical Society of Japan* 50(8):1999–2004, 1977.

Sawyer et al., "Interaction of Macrophage Cationic Proteins with the Outer Membrane of *Pseudomonas aeruginosa*," *Infection and Immunity* 56(3):693–698, 1988.

Schwyzer and Ludescher, "Untersuchungen über die Konformation des cyclischen Hexapeptids cyclo–Glycyl–L–prolyl–glycyl–glycyl–L–prolyl–glycyl mittels protonenmagnetischer Resonanz und Parallelen zum Cyclodecapeptid Gramicidin S," *Helvetica Chimica Acta* 52(7):2033–2040, 1969 (English Summary on page 2033).

Schwyzer et al., "Verdoppelungserscheinungen beim ringschluss von Peptiden V. Relative Bedeutung der sterischen Hinderung und der Assoziation über Wasserstoff–Brücken bei Tripeptiden. Spektroskopische Versuche zur Konformationsbestimmung," *Fasciculus* 47(54):441–464, 1964 (English Summary on p. 463).

Sönnichsen et al., "Effect of Trifluoroethanol on Protein Secondary Structure: An NMR and CD Study Using a Synthetic Actin Peptide," *Biochemistry* 31:8790–8798, 1992.

States et al., "A Two–Dimensional Nuclear Overhauser Experiment with Pure Absorption Phase in Four Quandrants," *Journal of Magnetic Resonance* 48:286–292, 1982.

Tamaki et al., "Adsorption of Cyclic Peptides Analogous to Gramicidin S and Gratisin onto Octadecylsilica Stationary Phase and Bacterial Cells," *J. of Chromatography* 413:287–292, 1987.

Wishart et al., "The Chemical Shift Index: A Fast and Simple Method for the Assignment of Protein Secondary Structure Through NMR Spectroscopy," *Biochemistry* 31:1647–1651, 1992.

Woody, "Circular Dichroism," *Methods in Enzymology* 246:34–71, 1995.

Yukioka et al., "Enzymatic Hydrolysis of Gramicidin S," *The J. of Biochemistry* 60(3):295–302, 1996.

Zhou et al., "Effect of Preferred Binding Domains on Peptide Retention Behavior in Reversed–Phase Chromatography: Amphipathic α–Helices," *Peptide Research 3*:8–20, 1990.

Ando, S., et al., "Studies of Peptide Antibiotics," *Int. J. Peptide Protein Res.,* 25:15–26 (1985).

Ando, S., et al., "Antimicrobial Specificity and Hemolytic Activity of Cyclized Basic Amphiphilic B–structural Model Peptides and their Interactions with Phospholipid Bilayers," *Biochim. Biophys. Acta,* 1147:42–49 (1993).

Ando, S., et al., "Drastic Reduction of Antimicrobial Activity by Replacement of Orn Residues with Lys in Cyclized Amphiphilic β–structural Model Peptides," *Int. J. Peptide Protein Res.,* 46:97–105 (1995).

Ando, Setsuko et al., "Biological Activities of Basic Amino Acid Rich Gramicidin S–Related Cyclic Peptides," *FFI Journal,* 170:75–81 (1996).

Aoyagi, Haruhiko et al., "Design and synthesis of bioactive cyclic peptides, AM–toxin I and gramicidin S," *Journal of Molecular Graphics,* 5:35–40 (Mar. 1987).

Aoyagi, H., et al., "Syntheses of Antibacterial Peptides, Gramicidin S Analogs and Designed Amphiphilic Oligopeptides," *Tetrahedron,* 44:877–866 (1988).

Gough, M., et al., "Antiendotoxin Activity of Cationic Peptide Antimicrobial Agents," *Infection and Immunity,* 64:4922–4927 (1996).

Katayama, T., et al., "Quantitative Structure–Hydrophobicity and Structure–Activity Relationships of Antibacterial Gramicidin S Analogs," *J. Pharm. Sci.,* 83:1357–1362 (1994).

Katsu, T., et al., "Mode of Action of the Gramicidin S Analogs Lacking Hydrophilic Amino Acid Residues on Biomembranes," *Chem. Pharm. Bull.,* 38:2880–2881 (1990).

Komiya, Ryoichi et al., "Interaction of Basic Tetradecapeptides Containing Isoleucine or Leucine Residues with Phospholipid Membrane and Their Hemolytic Activities," *Protein Research Foundation,* Osaka 201–204 (1996).

Kondejewski, L. H., et al., Chapter 22: "Design, Synthesis and Characterization of a Peptide β–sheet Model," in P.T.P. Kaumaya and R.S. Hodges, Eds., (Mayflower Scientific Ltd., 1996).

Kondejewski, L.H., et al., "Gramicidin S is Actice Against Both Gram–Positive and Gram–Negative Bacteria," *Int. J. Peptide Protein Res.,* 47:460–466 (1996).

Krauss, E.M. and Chan, S.I., "Complexation and Phase Transfer of Nucleic Acids by Gramicidin S," *Biochmistry,* 23:73–77 (1984).

Legendre, J.–Y. and Szoka, F.C.Jr., "Cyclic Amphipathic Peptide–DNA Complexes Mediate High–Efficiency Transfection of Adherent Mammalian Cells", *Proc. Natl. Acad. Sci.,* 90:893–897 (1993).

Matsushima, S., et al., "Immunosuppressive Effect of Gramicidin S on Experimental Ocular Neuritis and Allergic Encephalomyelitis," *Jpn. J. Ophthamol.,* 34:306–313 (1990).

Ono, S., et al., "Environment–Dependent Conformation and Antimicrobial Activity of a Gramicidin S Analog Containing Leucine and Lysine Residues," *FEBS Lett.,* 220:332–336 (1987).

Tamaki, M., et al., "Synthesis of Gramicidin S Analogues Consisting of Fourteen Amino Acid Residues," *Bull. Chem. Soc. Jpn.,* 61:3925–3929 (1988).

Tamaki, M. and Akabori, S., "Synthesis and Properties of Gramicidin S Analogs Consisting of Eight Amino Acid Residues," *Bull. Chem. Soc. Jpn.,* 64:2569–2571 (1991).

Tamaki, M., et al., "Role of Ring Size on the Secondary Structure and Antibiotic Activity of Gramicidin S," *Int. J. Peptide Protein Res.,* 46:299–302 (1995).

Thennarasu, S. and Nagaraj, R., "Design of 16–residue Peptides Possessing Antimicrobial and Hemolytic Activities or Only Antimicrobial Activity from an Inactive Peptide," *Int. J. Peptide Protein Res.,* 46:480–486 (1995).

Vaara, M. and Porro, M., "Group of Peptides that Act Synergistically with Hydrophobic Antibiotics Against Gram–Negative Enteric Bacteria," *Antimicrob. Agents Chemother.,* 40:1801–1805 (1996).

Wishart, D.S., et al., "A Method for the Facile Solid–Phase Synthesis of Gramicidin S and its Analogs," *Letters in Peptide Science,* 3:53–60 (1996).

* cited by examiner

Hydrophobic Face (3 Val and 3 Leu)

Basic Face (4 Lys)

ANTIMICROBIAL PEPTIDE COMPOSITIONS AND METHOD

This application claims the benefit of U.S. provisional application Ser. No. 60/028,315, filed Oct. 11, 1996, incorporated herein by reference in its entirety.

FIELD OF THE INVENTION

This invention relates to a class of cyclic peptides that exhibit gram-positive and gram-negative bactericidal activity, as well as fungicidal and anti-mycoplasma activity, and are useful as antimicrobial agents.

BACKGROUND OF THE INVENTION

The emergence of many medically relevant resistant strains of bacteria is a major issue in human health (Neu, 1992). It is becoming essential that new therapeutic agents be developed to combat microorganisms resistant to traditional antibiotics.

Gramicidin S (GS) is a naturally occurring cyclic peptide antibiotic (cyclo(Val-Orn-Leu-D-Phe-Pro)$_2$) first isolated from *Bacillus brevis*. There may be a reduced incidence of resistance developed against GS analogs, allegedly because the target of these analogs is the cell membrane of sensitive microorganisms; nonetheless, their mechanism of action is still not well understood. Furthermore, only two proteases are known to degrade GS, GS and its analogs are predicted to be stable in vivo (Maeda, et al., 1993; Yukioka, et al., 1966).

X-ray and NMR studies of GS have confirmed that it forms a two-stranded antiparallel β-sheet structure with the strands fixed in place by two type II' β-turns (Izumiya, et al., 1979; Rackovsky and Scheraga, 1980; Hull, et al., 1978). Based on studies of GS and its analogs, a number of structural requirements believed to be important for GS activity have been determined. These include: i) the requirement for an amphipathic structure containing basic residues on the hydrophilic face of the molecule (Izumiya, et al., 1979); ii) a β-sheet structure, or the ability to achieve a β-sheet structure in the presence of lipid bilayers (Izumiya, et al., 1979; Ando, et al., 1993, 1995), and iii) a high overall hydrophobicity (Kondejewski, et al., 1996; Katayama, et al., 1994; Tamaki and Ludescher, 1969).

A drawback to the use of GS as an antibiotic is its ability to lyse certain eukaryotic cells, which can result in a high level of hemolysis. Consequently GS is generally restricted to topical administration.

GS analogs containing more than ten residues have been shown to exhibit a change in activity profile (i.e., a change from gram positive specificity to gram negative specificity) when evaluated using agar-based assays, and to exhibit reduced hemolytic activity compared to GS (Ando, et al., 1993, 1995; Aoyagi, et al., 1988). Further, Aoyagi, et al. (1988) reported on a cyclic 14-mer having activity against gram positive and gram negative bacteria. Tamaki, et al. (1988) present CD data that shows that a 14-mer having two D-Phe residues as a non-L amino acid exists in a beta-sheet conformation, which can be disrupted by incorporation of a third D-amino acid in the peptide.

As mentioned above, despite its desirable properties as a broad spectrum antibiotic, the use of GS is limited by its side effects, specifically, its propensity for hemolysis. Therefore it would be useful to have a broad spectrum, cyclic peptide antibiotic that possess a high level of broad spectrum antimicrobial activity with much reduced hemolytic activity. Peptides having such properties form one aspect of the present invention.

More specifically, it is the discovery of the present invention that cyclic peptides that do not conform to the β-pleated sheet conformation that is characteristic of GS, exhibit superior properties, including broad spectrum antimicrobial activity and a high therapeutic index. The present invention provides guidance for the design and testing of cyclic peptides that exhibit such exceptional properties.

SUMMARY OF THE INVENTION

The present invention is generally directed to cyclized peptides that have antimicrobial activity. Such peptides are generally greater than 11 amino acids in length. The invention provides guidance for the design, production, testing and use of such peptides.

In one embodiment, the invention includes an analog of the 14-mer cyclic peptide having the amino acid sequence V1-K2-L3-K4-V5-$\underline{Y6}$-P7-L8-K9-V10-K11-L12-$\underline{Y13}$-P14 also identified by SEQ ID NO: 1, where Y represents D-tyrosine, numerals represent relative positions in the sequence of the peptide analog, and P14 is linked to V1. The analogs are further characterized by the presence of an amino acid substitution selected from the group consisting of (i) a D-amino acid in at least one of positions 1–5, 7–12 and 14 or an L-amino acid in position 6 or 13;

(ii) same class substitution at any of positions 1, 3, 5, 8, 10 or 12 with a class I hydrophobic sidechain;

(iii) same class substitution at any of positions 2, 4, 9 or 11 with a class II basic sidechain;

(iv) same class substitution at any of positions 6 or 13 with a D-amino acid comprising a class I hydrophobic sidechain;

(v) transposition of adjacent positions with substitutions of a class I sidechain at any of positions 1, 3, 5, 8, 10 or 12 with a class II basic sidechain and substitution of an adjacent class II sidechain with a class I sidechain to form a non-amphipathic cyclic peptide analog with respect to a plane formed by the peptide backbone of the cyclic structure;

(vi) substitution of class I sidechains for class II sidechains at one end of the cyclic structure and substitution of class II sidechains for class I sidechains at the opposite end of the cyclic structure to form a polarized non-amphipathic cyclic peptide having basic residues at one end of the cyclic peptide and hydrophobic residues at the opposite end of the structure; and (vii) combinations of any of (i)–(vi).

In one embodiment the analog referred to above excludes the peptide known as GS14 (SEQ ID NO: 1). In another embodiment, the analog is further characterized by a disrupted β-sheet structure, as evidenced by a circular dichroism spectrum that is shifted relative to a spectrum measured from a cyclic peptide having the sequence SEQ ID NO: 1 (GS14). In another embodiment, the analog has a specified hydrophobicity, defined in terms of a hydrophobicity window, herein. In a preferred embodiment, the peptide analog is further characterized by a therapeutic index of greater than 1, where the therapeutic index value is determined as a ratio of the concentration of analog required to produce hemolysis of human red blood cells divided by the concentration of analog required to inhibit growth of a specified microbe.

According to further preferred embodiments, the peptide analog is effective against one or more microbes selected from the group consisting of Pseudomonas, *Escherischia coli*, Salmonella, Staphylococcus, Bacillus, Enterococcus, Corynebacterium, Candida, and mycoplasma.

In another preferred embodiment, amino acid substitution to form the analog comprises substitution of a D-valine at a position selected from the group consisting of position 1 and position 5. In a further preferred embodiment, the amino acid substitution comprises substitution of a D valine at position 10. In still a further embodiment, the amino acid substitution comprises substitution of a D-leucine at a position selected from the group consisting of position 8 and position 12. The amino acid substitution may also include substitution of a D-leucine at a position 3.

In a related embodiment, the peptide analog of the invention has an amino acid substitution of a D-lysine at a position selected from the group consisting of position 2, position 4, position 9 and position 11. A further embodiment includes substitution at any of positions 1, 3, 5, 8, 10 or 12 with an amino acid selected from the group consisting of alanine, valine, leucine, norvaline, isoleucine, norleucine, methionine, phenylalanine, tyrosine and tryptophan. Here, the amino acid substitution is preferably selected from the group consisting of a leucine at each of positions 1, 5 and 10 (V3/L3), an alanine at each of positions 3, 8 and 12 (L3/A3), an alanine at each of positions 1, 5 and 10 (V3/A3), and an alanine at each of positions 1, 3, 5, 8, 10, and 12. Within this group, the amino acid substitution will preferably consist of a leucine at each of positions 1, 5 and 10 and further comprising a D-phenylalanine at each of positions 6 and 13. A further modification of this particular construct can be made by substitution at position 4 by D-lysine.

In a related embodiment, peptides in accordance with the invention are GS14 analogs having amino acid substitutions at any of positions 2, 4, 9 or 11 with an amino acid selected from the group consisting of lysine, arginine, ornithine, histidine, 2,4-diaminobutyric acid and 2,3-diaminoproprionic acid.

In a further embodiment, the peptide analog will have an amino acid substitution at any of positions 6 or 13 with an amino acid selected from the group consisting of a class I hydrophobic D-amino acid. Preferably, such a construct will include a substitution at each of positions 6 and 13 with a D-phenylalanine.

Additional peptide analogs in accordance with the invention include amino acid substitutions that represent a transposition of adjacent positions with substitutions of a class I sidechain at any of positions 1, 3, 5, 8, 10 or 12 with a class II basic sidechain and substitution of an adjacent class II sidechain with a class I sidechain to form a non-amphipathic cyclic peptide analog with respect to a plane formed by the peptide backbone of the cyclic structure. According to this feature of the invention, the substitution may consist of a valine at position 4, a lysine at position 5, a leucine at position 11 and/or a lysine at position 12.

In still another preferred embodiment, peptides of the present invention include peptide analogs of GS14 having a lysine at position 1, a valine at position 2, a lysine at position 3, a leucine at position 4, a lysine at position 5, a lysine at position 8, a valine at position 9, a lysine at position 10, a leucine at position 11, and a lysine at position 12. In a preferred embodiment, such a peptide includes a D-lysine at position 1. In another preferred embodiment, the peptide has a D-valine at position 12.

In another general embodiment, GS14 peptide analogs in accordance with the present invention include substitution of class I sidechains for class II side chains at one end of the cyclic structure and substitution of class II sidechains for class I sidechains at the opposite end of the cyclic structure to form a polarized non-amphipathic cyclic peptide having basic residues at one end of the cyclic peptide and hydrophobic residues at the opposite end of said structure. Such substitutions may be effected by a leucine at position 1, a valine at position 2, a lysine at position 5, a lysine at position 8, a leucine at position 11, and a valine at position 12.

In a related aspect, the invention includes a method of enhancing the therapeutic index of an antimicrobial amphipathic cyclic peptide having a β-pleated sheet structure. According to this aspect of the invention, amino acids in the peptide are replaced so as to to disrupt the β-pleated sheet structure, according to the methods discussed herein. In a preferred embodiment, the amphipathic cyclic peptide has the sequence SEQ ID NO: 1 [GS14] and comprises an amino acid substitution selected from the group consisting of (i) a D-amino acid at at least one of positions 1–5, 7–12 or 14;

(ii) an L-amino acid in at least one of positions 6 and 13;

(iii) same class substitution at any of positions 1, 3, 5, 8, 10 or 12 with a class I hydrophobic sidechain;

(iv) same class substitution at any of positions 2, 4, 9 or 11 with a class II basic sidechain;

(v) same class substitution at any of positions 6 or 13 with a class I hydrophobic sidechain;

(vi) transposition of adjacent positions with substitutions of a class I sidechain at any of positions 1, 3, 5, 8, 10 or 12 with a class II basic sidechain and substitution of an adjacent class II sidechain with a class I sidechain to form a non-amphipathic cyclic peptide analog with respect to a plane formed by the peptide backbone of the cyclic structure;

(vii) substitution of class I sidechains for class II side chains at one end of the cyclic structure and substitution of class II sidechains for class I sidechains at the opposite end of the cyclic structure to form a polarized non-amphipathic cyclic peptide having basic residues at one end of the cyclic peptide and hydrophobic residues at the opposite end of said structure; and (viii) combinations of any of (i)–(vii).

In a further preferred embodiment, the method includes making a substitution that is effective to form any of the peptide analogs of claims 2–24.

In a related embodiment, the invention also includes a pharmaceutical composition that includes any of the peptide analogs of claims 1–24, characterized by a therapeutic index of greater than 1 against a specified microbe. Such a composition may also include an acceptable pharmaceutical excipient. Such composition may be effective against gram positive or gram negative bacteria, for example, Pseudomonas, *Escherischia coli*, Salmonella, Staphylococcus, Bacillus, Enterococcus, or Corynebacterium; against fungi, for example, Candida.

The invention also includes a method of treating a microbial infection in a subject. According to this aspect of the invention, the subject is given any of the peptide analogs of claims 1–24 in an amount effective to produce a microbe-inhibitory concentration of said peptide analog in the subject.

In a related aspect, the invention includes a method of treating a mycoplasma infection or contamination, such as in cell culture. Here, the mycoplasma is exposed to any of the peptides of claims 1–24 in an amount effective to produce a mycoplasma inhibitory concentration of said peptide analog. In a preferred embodiment, the peptide is GS14.

In a more general aspect, the invention includes a cyclic antimicrobial peptide having the sequence $[(X1X2)_n X1\text{-}X3\text{-}$ P], (Examples of these include the sequences presented as SEQ ID NOs: 35–38) where X1 is independently selected from the group consisting of alanine, valine, leucine, norvaline, isoleucine, norleucine, methionine, phenylalanine, tyrosine and tryptophan, X2 is independently selected from the group consisting of lysine, arginine, histidine, ornithine, 2,4-diaminobutyric acid, and 2,3-diaminopropionic acid, X3 is a D-amino acid selected from the class I group of hydrophobic amino acids consisting of of alanine, valine, leucine, norvaline, isoleucine, norleucine, methionine, phenylalanine, tyrosine and tryptophan, and n is an integer that is greater than or equal to 2, said cyclic peptide characterized by a disrupted amphipathic β-pleated sheet structure, as evidenced by a circular dichroism spectrum that is shifted relative to a spectrum measured from a cyclic peptide having the sequence SEQ ID NO: 1 [GS14].

In a preferred embodiment, n is an integer between 2 and 5. In still another preferred embodiment, at least three amino acids comprising said peptide are D-amino acids. More specifically, the peptide has the sequence V1-K2-L3-K4-V5-Y/F6-P7-L8-K9-V10-K11-L12-Y/F13-P14, wherein Y/F designates a D-tyrosine or a D-phenylalanine residue and wherein said third D-amino acid is selected from the group consisting of K2, K4, V5, L8, K9, V10, and K11. In another embodiment, one of positions X1 or X2 is a deletion.

In still another related aspect, the invention includes a cyclic peptide having the sequence $(X1X2)_n$-X3-P-$(X2X1)_n$-X3-P (Examples of these include the sequences presented as SEQ ID NOs: 39–42), where n is an integer greater than or equal to 2, further characterized as lacking a β-pleated sheet structure, as evidenced by circular dichroism spectrum lacking peaks characteristic of β-pleated sheet structure. Here, each X1 is independently selected from the group consisting of alanine, valine, leucine, norvaline, isoleucine, norleucine, methionine, phenylalanine, tyrosine and tryptophan, each X2 is independently selected from the group consisting of lysine, arginine, histidine, ornithine, 2,4-diaminobutyric acid, and 2,3-diaminoproprionic acid, each X3 is a D-amino acid independently selected from the group consisting of alanine, valine, leucine, norvaline, isoleucine, norleucine, methioine, phenylalanine, tyrosine and tryptophan. In preferred embodiments, this peptide takes the form VKLYPKVKLYP (GS12, SEQ ID NO:29) LKVKYPKLKVY (GS12LV, SEQ ID NO:30), VKLKFPKVKLFP (GS12F, SEQ ID NO:31), VOLOFPOVOLFP (GS12FO SEQ ID NO:32), or LOLOFPOLOLFP (GS12FO/LL, SEQ ID NO:33). The peptide may also have a deletion at one of the positions X1 or X2.

These and other aspects of the invention can be discerned by persons skilled in the art from the Descriptions and Examples that follow.

Figure 15:
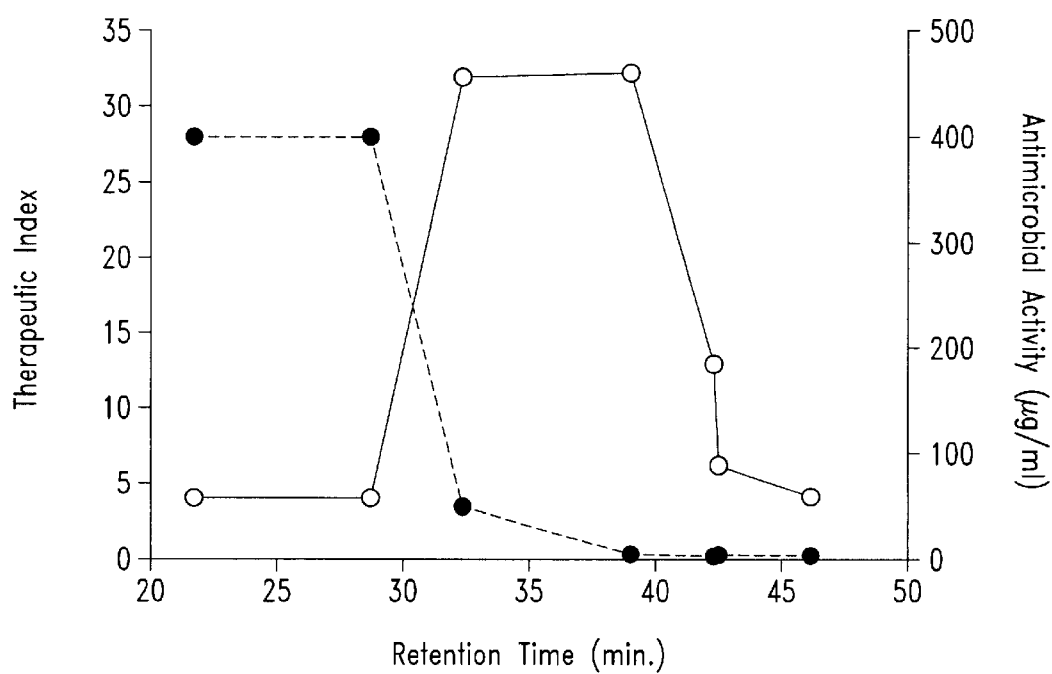

FIG. 15 shows antifungal activity and microbial specificity of GS14K4 hydrophobicity analogs. The antifungal activity (closed circles) and the therapeutic index (open circles) of the GS14K4 analogs shown in Table 3 are plotted as a function of retention time on RP-HPLC. A value of 400 μg/ml was used for values of >200 μg/ml in Table 6 for the plot as well as for calculation of the therapeutic index. For hemolytic activity values >800 μg/ml (Table 4) a value of 1600 μg/ml was used for calculation of the therapeutic index.

Figure 16:
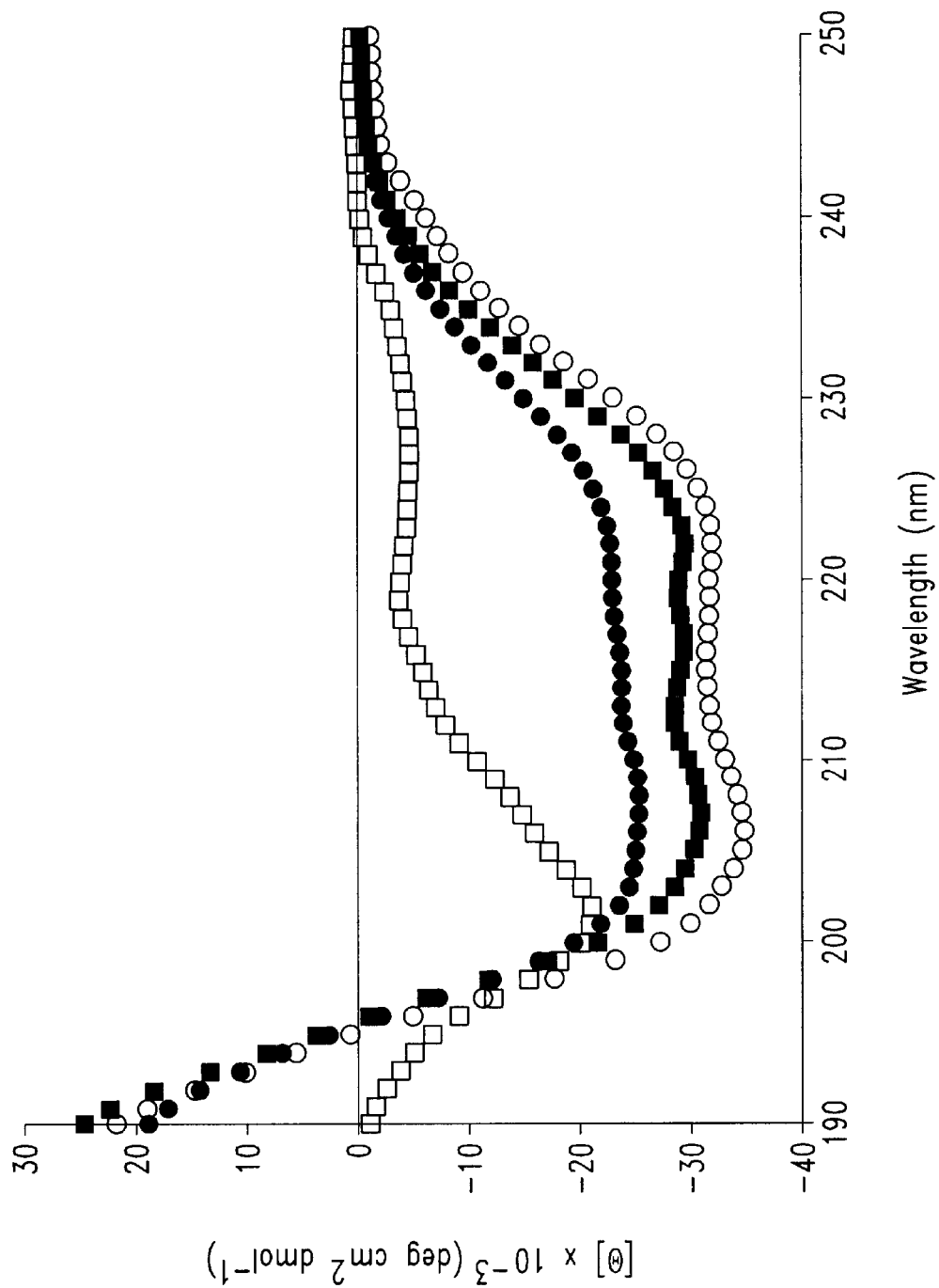

FIG. 16 shows CD spectra of GS14 (open circles), GS14na (closed squares), GS14napol (closed circles) and GS14inv (open squares).

DETAILED DESCRIPTION OF THE INVENTION

I. Definitions

As used herein, the terms "antimicrobial" and "antibiotic" are used to refer to compounds which kill and/or inhibit the growth of microbes, including but not limited to bacteria, fungi, mycoplasma and microscopic algae and parasites. The use of the term "antibiotic" in reference to certain compounds is not meant to limit the activity to bacteria.

The term "peptide" as used herein refers to two or more amino acids joined by a peptide bond, which is a —CO—NH—, or "amide" linkage. A cyclic peptide is one in which the α-amino group on the first amino acid is joined via an amide linkage to the α-carboxyl group of the last amino acid in the chain. For purposes of convenience, cyclic peptides are shown as linear sequences herein.

Amino acid residues are referred to herein by their standard single letter notations: A, alanine; C, cysteine; D, aspartic acid; E, glutamic acid; F, phenylalanine; G, glycine; H, histidine; I, isoleucine; K, lysine; L, leucine; M, methionine; N, asparagine; O, ornithine; P, proline; Q, glutamine; R, arginine; S, serine; T, threonine; V, valine; W, tryptophan; X, hydroxyproline; Y. tyrosine. Naturally occuring amino acids are generally L-enantiomers; D-amino acids are so-designated (such as "D-lysine").

Examples of hydrophobic class I amino acids include alanine, valine, leucine, isoleucine, norvaline, norleucine, methionine, phenylalanine, tyrosine and tryptophan.

Basic class II amino acids include lysine, arginine, ornithine, histidine, 2,4-diaminobutyric acid, and 2,3-diaminoproprionic acid.

The term "peptide analog" as used herein refers to a peptide that is derived from a parent or reference peptide, and which is characterized by certain defined amino acid substitutions with respect to the reference peptide. It will be understood that in addition to the substitutions specifically defined herein, the term peptide analog can be considered to cover conservative substitutions of any particular amino acid residue, such as a basic amino acid for another basic amino (e.g., lysine in place of arginine).

The term "amphipathic" refers to molecules having two groups with characteristically different properties; in the context of the present invention, it refers to a molecule in which positively charged groups are positioned above a reference axis (plane of cyclic peptide backbone) while hydrophobic groups are positioned below the axis.

The term "therapeutic index" is a measure of toxicity of a specific compound and is expressed as a ratio that is obtained by dividing the dose or concentration of the drug that induces an undesirable effect by the dose or concentration of the drug that provides a beneficial effect.

II. Antimicrobial Peptides

The well-characterized cyclic 10-mer peptide antibiotic gramicidin S is notable for its amphipathic structure; as described in more detail below, in an aqueous environment the two peptide arms of the molecule form an anti-parallel β-pleated sheet. These arms are separated by a type II' β-turn at either end of the cyclic structure. The amphipathic character of the molecule is dictated by alternating hydrophobic and basic residues that segregate to opposite sides of the plane of the backbone ring when the peptide adopts the anti-parallel β-pleated sheet formation.

Figure 1:
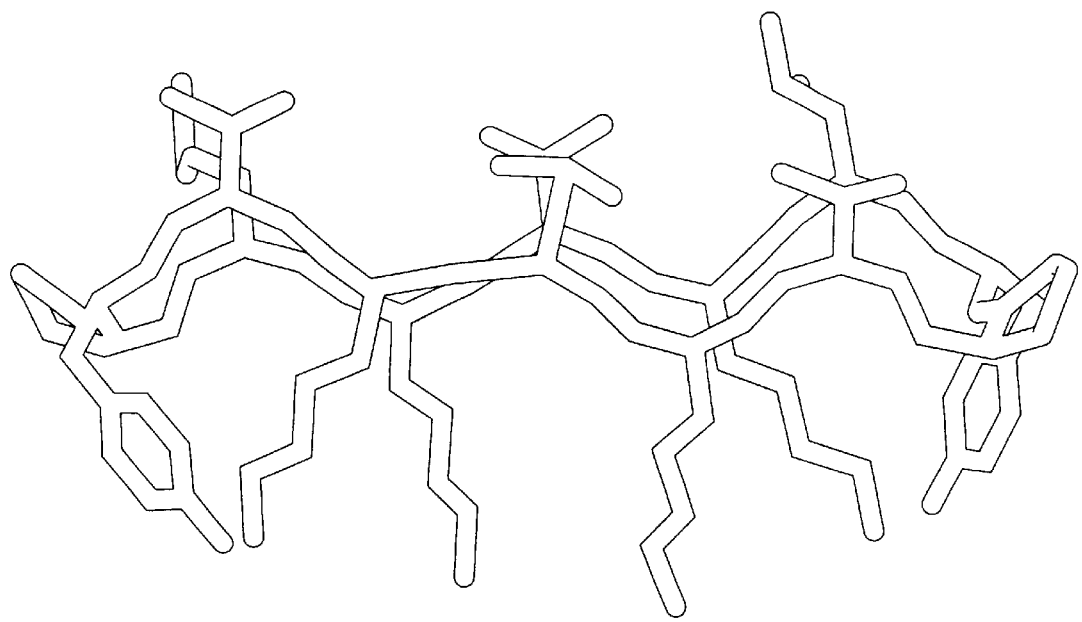
FIG. 1 shows a schematic structural representation of GS14, illustrating its amphipathic cyclic anti-parallel β-sheet structure, where basic residues (4 Lys) orient on one face and hydrophobic residues (3 Val, 3 Leu) orient on the other face of the molecule.

In support of the present invention, a 14-mer peptide was designed that, while having a very different amino acid sequence, shares many of the properties of gramicidin S (GS). Similar to GS, this 14-mer, termed GS14 herein, exhibits limited antimicrobial activity as well as hemolytic activity in biological systems. According to studies carried out in support of the present invention, GS14 forms an anti-parallel β-pleated sheet in solution, and its alternating hydrophobic and basic amino acid residues orient to opposite sides of the molecule (FIG. 1).

It is the discovery of the present invention that perturbation of the anti-parallel β-pleated sheet structure, by one or more of a number of means exemplified below, results in compositions having unique properties that are distinguishable from the parent compound as well as from GS.

Specifically, according to an important aspect of the present invention, molecules are formed that have the characteristic anti-microbial properties of GS, while lacking the deleterious hemolytic properties of these compounds. Moreover, using the methods and teachings provided herein, a practitioner will be able to design and select such compounds, as well as to test them for selected antimicrobial activity.

A. Synthesis of Peptide Analogs

Cyclic peptides were synthesized by solid phase peptide synthesis using t-butyloxycarbonyl chemistry and cyclized, as detailed in Examples 1 and 2. The method described in Example 1 is preferred and also forms part of the present invention, since it avoids racemization of the composition during cyclization.

In addition to the methods described herein, the prior art contains other descriptions of cyclic peptide synthesis of GS, using solid phase techniques. However, each of these methods required either two additional steps or the use of non-conventional solid phase protocols. Klostermeyer (1968) used tosyl-protected delta-amino groups of ornithine and, following cleavage of peptide from the resin, cyclized the tosylated peptide with DCC in the presence of p-nitrophenol. Removal of the tosyl groups gave the desired cyclic product in 22% yield. A similar procedure for the solid phase synthesis of gramicidin S has also been described by Losse and Neubert (1970). In this case, cyclization of the furfuryloxycarbonyl protected peptide was accomplished using DCC and p-nitrophenol with a final yield of 20%. In 1977, Sato et al. synthesized gramicidin S using the nitro-benzyl protecting group for Orn residues and cyclized the azide activated linear peptide for three days in pyridine. Yields of the cyclic deprotected peptide were typically 30%. More recently, a heavy atom derivative of gramicidin S was synthesized by solid phase synthesis using Boc chemistry. In this synthesis Orn was initially protected by the benzyloxycarbonyl (Z) group and the α-amino terminal by the HF-stable troc group. Following HF cleavage, Orn was re-protected with Boc, followed by selective removal of the troc protecting group.

Cyclization was carried out using EDAC and NHS. While each of these earlier methods has shown some success, they: (1) typically require at least two additional synthetic steps, (2) have not been adapted to automatic peptide synthesizer, (3) have not been tested on more than one gramicidin analog, (4) have reported yields of less than 30% and (5) require the use of unconventional protected amino acids or unconventional solid phase chemistry.

While any of the prior art methods described above are adaptable to the peptides of the present invention, the methods described in Examples 1 and 2 are preferred, since they use standard solid phase technology and a single solution-phase cyclization step. The synthetic portion is carried out on an automatic synthesizer and provides relatively high yields for most of the peptide analogs tested. The method described in Example 2 is best suited to shorter peptides, e.g., less than 10–12 residues.

Briefly, according to both methods described herein, peptides are synthesized by solid-phase peptide synthesis using standard t-butyloxycarbonyl (t-Boc) chemistry (Erickson and Merrifield, 1976) as reported (Wishart, et al., 1996, incorporated herein by reference). According to the method detailed in Example 1, the peptides are synthesized on Boc-Pro-phenylacetamidomethyl resin in an automated peptide synthesizer. Side-chain protecting groups were as described in Example 1. Side-chain formylation was carried out by the procedure of Kitagawa, et al. (1994) using Nα-Boc-amino acids. Peptides were cleaved from the resin using anhydrous hydrogen fluoride in the presence of 10% anisole. Peptides were extracted from the resin with glacial acetic acid and lyophilized. Crude linear peptides were purified by reversed-phase HPLC. Purity of peptides was verified by analytical reversed-phase HPLC. Identity of peptides was confirmed by mass spectrometry fitted with an electrospray ionization source operating in positive ion mode.

Pure linear formylated peptides were cyclized at a concentration of 2 mg/mL in N,N-dimethylformamide using 3 equivalents of each of benzotriazolyl N-oxytridimethylamino-phosphonium hexafluorophosphate, 1-hydroxybenzotriazole and diisopropylethylamine. The progress of the cyclization reaction was monitored by analytical reversed-phase HPLC and was typically complete after 1 h. Cyclic peptides were then deformylated by exposure to acidic methanol and were purified by preparative reversed-phase HPLC.

According to an alternate method (Example 2) linear analog peptides were synthesized on Boc-Lys(2ClZ)-PAM or Boc-Orn(Z)-PAM resin using an Applied Biosystems 430A automated peptide synthesizer. Standard deprotection, wash and coupling steps were performed for each round of the synthesis. The blocked peptides were cleaved from the resin using anhydrous HF in the presence of 10% anisole and 2% 1,2-ethanedithiol. The crude linear peptides were purified using a reversed-phase C8 semi-preparative Synchropak column with a linear gradient of TFA/$H_2O$ and TFA/acetonitrile. Purity of the peptides was verified by analytical reversed-phase HPLC. Identity of the peptides was confirmed by time-of-flight mass spectrometry.

For cyclization after purification, the unprotected linear peptide was placed in a small flask containing DCM with DCC, HOBt and DIEA and stirred vigorously with a magnetic stirrer at room temperature for up to 24 hours. The progress of the cyclization reaction was monitored by both analytical reversed phase HPLC and plasma desorption time-of-flight mass spectrometry. Cyclizations were typically complete after six hours with final overall yields often approaching 80%. Final purification of the cyclic peptides was achieved with reversed phase HPLC using identical conditions for the linear peptides.

B. Design of Peptide Analogs

Based on cyclodimerization studies with 3 and 5 residue peptides, Schwyzer (1958) proposed that cyclic peptides containing 2(2n+1) residues, where n=1, 2, 3 . . . could form β-sheet structures, and later presented structural evidence that this rule held true for cyclic hexapeptides (Schwyzer, et al., 1964; Schwyzer and Ludescher, 1969). These findings have implications for design of cyclic β-sheet antibiotics, since the β-sheet backbone structure (or lack of) will determine the relative positioning of the side chains.

It is the discovery of the present invention, as described below, that the characteristic anti-parallel β-pleated sheet conformation and attendant amphipathic nature of GS (n=2, peptide length=10) and the novel GS14 peptide (n=3) exemplified herein confer certain of the therapeutically undesirable characteristics of these peptides, such as hemolytic activity.

In studies carried out in support of the present invention, GS14, GS12 and analogs thereof were initially designed to incorporate an alternating hydrophobic-hydrophilic residue pattern, where Val and Leu residues make up the hydrophobic face of the molecule and ornithine or lysine residues constitute the hydrophilic face (FIG. 1). This was accomplished by increasing the length of the ring by successively incorporating either hydrophobic (Val and Leu) or hydrophilic (Lys or Orn) residues. Peptide analogs used for preliminary screening also incorporated additional substitutions, as described in further detail below.

Based on the studies described in conjunction with the exemplary peptides described herein, it is the discovery of the present invention that cyclic peptides that either lack the anti-parallel β-pleated sheet conformation of GS or have a perturbed structure thereof are desirable therapeutics. Thus, in one aspect, the invention includes peptides that do not conform to the length requirements for forming an anti-parallel β-pleated sheet (e.g., peptide length not conforming to an integer value of n in the equation 2(2n+1), such as 12-mers, 13-mers, 15-mers, 16-mers and the like) or peptides designed with β-pleated sheet-destroying substituents, as discussed below. Such disrupted amphipathic β-pleated sheet structure can be observed by comparing a circular dichroism spectrum of the test compound with that of a known β-pleated sheet forming compound, such as GS14. Compounds exhibiting a CD spectrum that is shifted relative to a spectrum measured from such a reference peptide are candidates for therapeutic peptides in the present invention.

In the sections that follow, guidance is provided to the practitioner for designing and testing such peptides. Briefly, based on the principles provided herein, the practitioner can design candidate cyclic peptides and test them for physical (e.g., CD spectra) and biological (e.g., antimicrobial, hemolytic) properties that are consistent with useful therapeutic agents as exemplified below.

While the invention is described using an exemplary anti-parallel β-pleated sheet-forming 14-mer (GS14), it is appreciated that the principles and results are applicable to peptides of varying length.

1. GS14 Peptide Analogs

The present invention is exemplified by a 14-mer cyclic peptide having the amino acid sequence V1-K2-L3-K4-V5-<u>Y</u>6-P7-L8-K9-V10-K11-L12-<u>Y</u>13-P14 also identified by SEQ ID NO: 2, where <u>Y</u> represents D-tyrosine, numerals represent relative positions in the peptide analog. As noted above, the position designators are relative, since the peptide is cyclized, with P14 linked to V1. In view of experiments carried out in support of the present invention, it is now recognized that there are several ways that the native anti-parallel β-pleated sheet conformation of this peptide can be perturbed, in order to achieve desired biological characteristics. Analogs formed in accordance with the present invention categorized as follows:

a. Diastereomers

Diastereomeric molecules are formed in accordance with the present invention by introducing additional D-amino acids into the non-turn regions of the molecule, or substituting an L-amino acid for the D-amino acid usually present in the β-turn region. More specifically, such molecules can be formed by substituting a D-amino acid into at least one of positions 1–5, 7–12 and 14 or a L-amino acid in position 6 or 13.

Table 1 lists various GS14 analogs and their structures formed in accordance with this aspect of the invention. In the table, as elsewhere in this document, the convention of underlining an amino acid designator is used to signify the presence of a D-amino acid in the sequence. Thus, in the native GS14 sequence (SEQ ID NO: 1), tyrosines present in the turn regions as positions 6 and 13 are D-tyrosines. Additional analogs are named to indicate the residue that has been changed. For example, as illustrated, GS14K2SEQ ID NO:3 is a peptide having a D-lysine at position 2. Further discussion of the physical and biological characteristics of these analogs are provided in Part 2, below.

b. Same Class Substitution Analogs

Another class of GS14 analog is formed by analogs in which residues at certain positions are substituted by amino acids having similar physicochemical characteristics. For example, positions 1, 3, 5, 8, 10 or 12, which in GS14, contain amino acids having hydrophobic sidechains can be replaced with residues possessing similar hydrophobic properties, referred to herein as "Class I" or "hydrophobic" amino acids. Class I amino acids include, for example, alanine, valine, leucine, norvaline, isoleucine, norleucine, methionine, phenylalanine, tyrosine and tryptophan. Basic sidechain-containing amino acids such as are found at positions 2, 4, 9 or 11 can be substituted by any of the "Group II" amino acids, such as lysine, arginine, ornithine, histidine, 2,4-diaminobutyric acid and 2,3-diaminopropionic acid. Similarly, D-tyrosine turn positions 6 and 13, can be substituted by D-isomers of hydrophobic, class I amino acids.

In the context of the present invention, it is noted that such same class substitutions generally do not alter the physical properties (e.g., anti-parallel β-pleated sheet conformation) of the resulting cyclic peptides relative to the parent peptide; however, they may result in slightly different biological properties. Moreover, it is appreciated that the availability of same class substitutions significantly broadens the diversity of primary sequences that are considered GS14 analogs herein.

c. Transposed Analogs

Transposed analogs of GS14 are those analogs in which two adjacent positions in the non-turn regions of the peptide are interchanged. That is, GS14 positions 1–4 are VKLK; transposition of adjacent residues in this region yields KVLK, VLKK or VKKL. With reference to FIG. 1, it is apparent that such a transposition results in a difference in the amphipathic nature of the resulting molecule, due to a redistribution of a basic residue with respect to the plane of the molecule. An example of a transposition analog of GS14 is referred to as GS14na SEQ ID NO:24, herein.

d. Polarized Analogs

Polarized analogs are analogs of GS14 in which a class I hydrophobic sidechains at one end of the molecule (i.e., in the vicinity of one of the turns) have been switched to class II basic side chains. This forms a polarized cyclic peptide having basic residues at one end of the cyclic peptide and hydrophobic residues at the opposite end of the structure. The molecule is not amphipathic as described herein (i.e., with respect to the plane of the cyclic peptide backbone). An example of a polarized analog is provided by GS14napol (SEQ ID NO:25.

e. Inverted Analogs

More extensive transposition of adjacent residues is found, for example in the GS14 analog referred to as GS14inv, herein, where each adjacent pair of residues has been interchanged. It is further noted that GS14inv exemplifies a combination peptide, since the "odd" fifth residues in the non-turn regions are also switched from a hydrophobic residue to a basic residue.

In accordance with the invention, it is also possible to combine the foregoing types of alterations in a single molecule. More specific examples of the above-listed analog categories are provided in conjunction with a discussion of the formation and testing of such molecules in the section that follows.

C. Physical and Biological Characterization of GS14 Analogs

This section describes physical and biological characteristics of the GS14 analog types outlined in the previous section. In accordance with a more general aspect of the present invention, it is appreciated that test compounds formed along the lines of the invention can be conveniently assessed in one or more of the assays discussed below, in order to determine whether the test molecule provides the desired characteristics. For example, as described herein, perturbation of anti-parallel β-pleated sheet conformation and/or amphipathicity is desirable, in order to decrease hemolytic activity. Accordingly, a peptide analog designed with the idea of disrupting β-pleated sheet properties should be tested to determine structural characteristics with reference to the reference compound; such a molecule may alternatively or in addition be tested directly in the relevant biological assay (e.g., hemolysis assay).

1. Diastereomer Analogs of GS14

In studies carried out in support of the present invention, residues of GS14 were systematically replaced with enantiomers (Table 1), in order to effect disruption of β-sheet structure and amphipathicity. These substitutions were made to test the initial hypothesis that GS14 could be transformed into a peptide possessing a high therapeutic index by virtue of disrupting the β-sheet character, and hence the amphipathicity, of the molecule.

Figure 2:
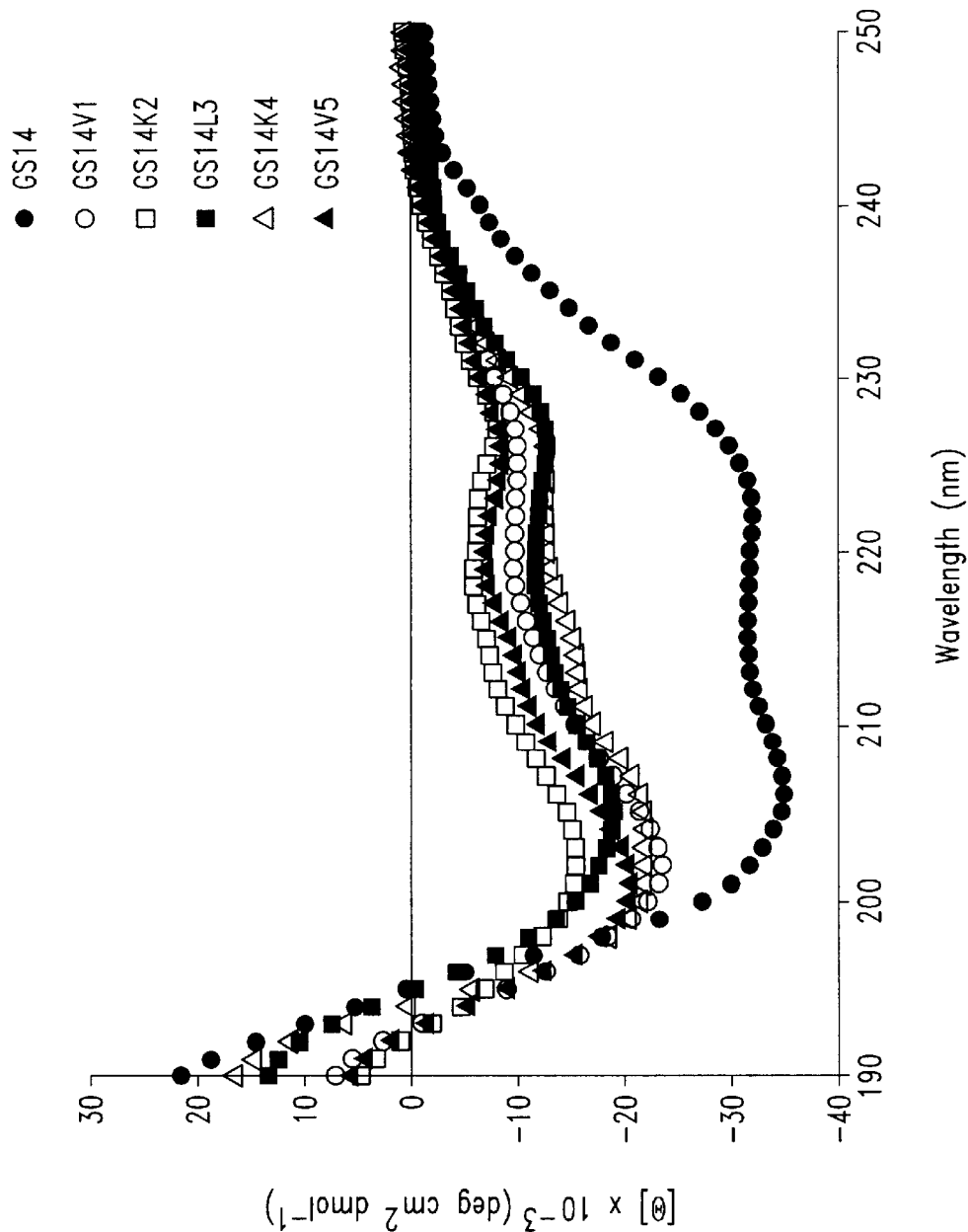
FIG. 2 shows CD spectra of GS14 and GS 14 diastereomers recorded in 5 mM sodium acetate buffer, pH 5.5, at 20° C. Samples were GS14, closed circles; GS14V1, open circles; GS14K2, open squares; GS14L3, closed squares; GS14K4, open triangles; GS14V5, closed triangles.

The fourteen test diastereomers of GS14 are shown in Table 1. Each diastereomeric analog has a different single amino acid enantiomeric substitution. In addition, two diastereomers were formed to have either two or four entantiomeric substitutions. These latter substitution variants are illustrated as GS14K2K4 (SEQ ID NO:16), in which lysines at positions 2 and 4 were substituted with D-lysines, and GS14K2K4K9K11 (SEQ ID NO:17), in which all lysines in the molecule were replaced with D-lysines. All peptides were synthesized with Pro as the carboxyl terminus to prevent any racemization of the C-terminus during the cyclization reaction. The peptides were characterized with respect to their structural and biological properties.

a. Physicochemical Characterization of GS14 Diastereomeric Analogs (i) Circular Dichroism Spectroscopy Circular dichroism measurements provides an indication of the absence or presence of anti-parallel β-pleated sheet conformation in a cyclic peptide. Shown in FIG. 2 are the CD spectra of GS14 and representative single residue substitution diastereomers.

From initial studies carried out in support of the present invention, it was known that both GS and GS14 have a similar β-sheet conformation and exhibit similar CD spectra, the latter possessing two large negative ellipticities 206 nm and 223 nm. CD spectra were measured as detailed in Example 3 herein. All the single replacement diastereomers of GS14 exhibit CD spectra more typical of disordered structures (i.e., reduced negative ellipticities in this region, indicating that each enantiomeric substitution within the framework of GS14 resulted in the disruption of β-sheet structure. All single residue substitution diastereomers as well as those containing either two or four entantiomeric substitutions (see Table 1) also exhibited disordered-like, or non β-sheet-like CD spectra. In additional experiments, CD spectra of GS14 and representative diastereomers were measured in the presence of the hydrophobic, structure-inducing solvent, trifluoroethanol (TFE). TFE is generally thought of as a helix-inducing solvent (Sonnichsen, et al.); however recent studies have shown that aqueous solutions containing TFE can also stabilize β-hairpin and β-turn structures. The β-sheet structure of GS14 is greatly enhanced in 50% TFE, as evidenced by larger negative ellipticities at both 206 nm and 223 nm. The β-sheet structure of representative GS14 diastereomers was also enhanced in the presence of 50% TFE, with CD spectra approximating that of GS14 under aqueous conditions. More importantly however, the β-sheet structure, and therefore also the amphipathic nature, of the diastereomers is inducible to varying degrees, depending on the position of the enantiomeric substitution. All diastereomers exhibited some enhancement of β-sheet structure in the presence of TFE.

(ii) NMR Spectroscopy

Figure 3A:
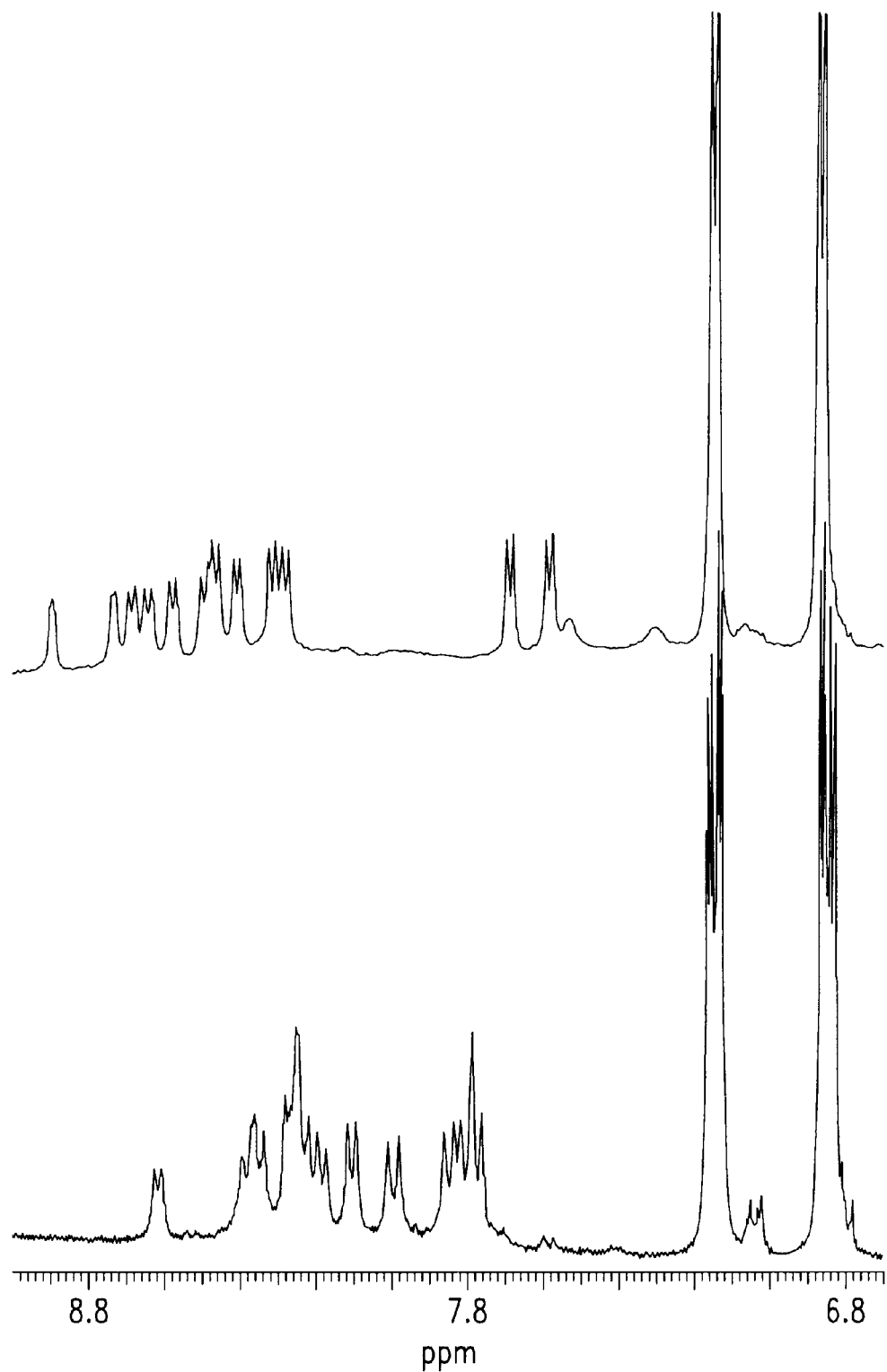
FIGS. 3A and 3B show one dimensional $^1$H-NMR spectra of GS14 and GS14K2. Spectra shown are of the amide regions (A) and Hα regions (B) for GS14 (upper panels) and GS14K2 (lower panels). Spectra were recorded in 20% $D_2O$, in $H_2O$, pH 5.5, at 25° C.

The disruption of β-sheet structure in GS14 diastereomers was verified by NMR spectroscopy, carried out according to standard methods known in the art. The HN and Hα regions of $^1$H-NMR spectra are shown for GS14 in FIG. 3A (top panel) and one diastereomer, GS14K2 (bottom panel). From the spectra of the HN region, GS14 (top) shows well separated doublets of all amide protons indicating a high degree of symmetry and ordered structure. The same region for GS14K2 (bottom) shows much more overlap indicating a less ordered and less symmetrical structure. Tyrosine γ and δ resonances are located between 6.8 and 7.2 ppm. Comparison of the two compounds shows that the tyrosine resonances are equivalent (doublets) in GS14 (upper) indicating two well defined turns, whereas GS14K2 shows multiplets in this region indicative of non-equivalent turns in the structure.

Figure 3B:
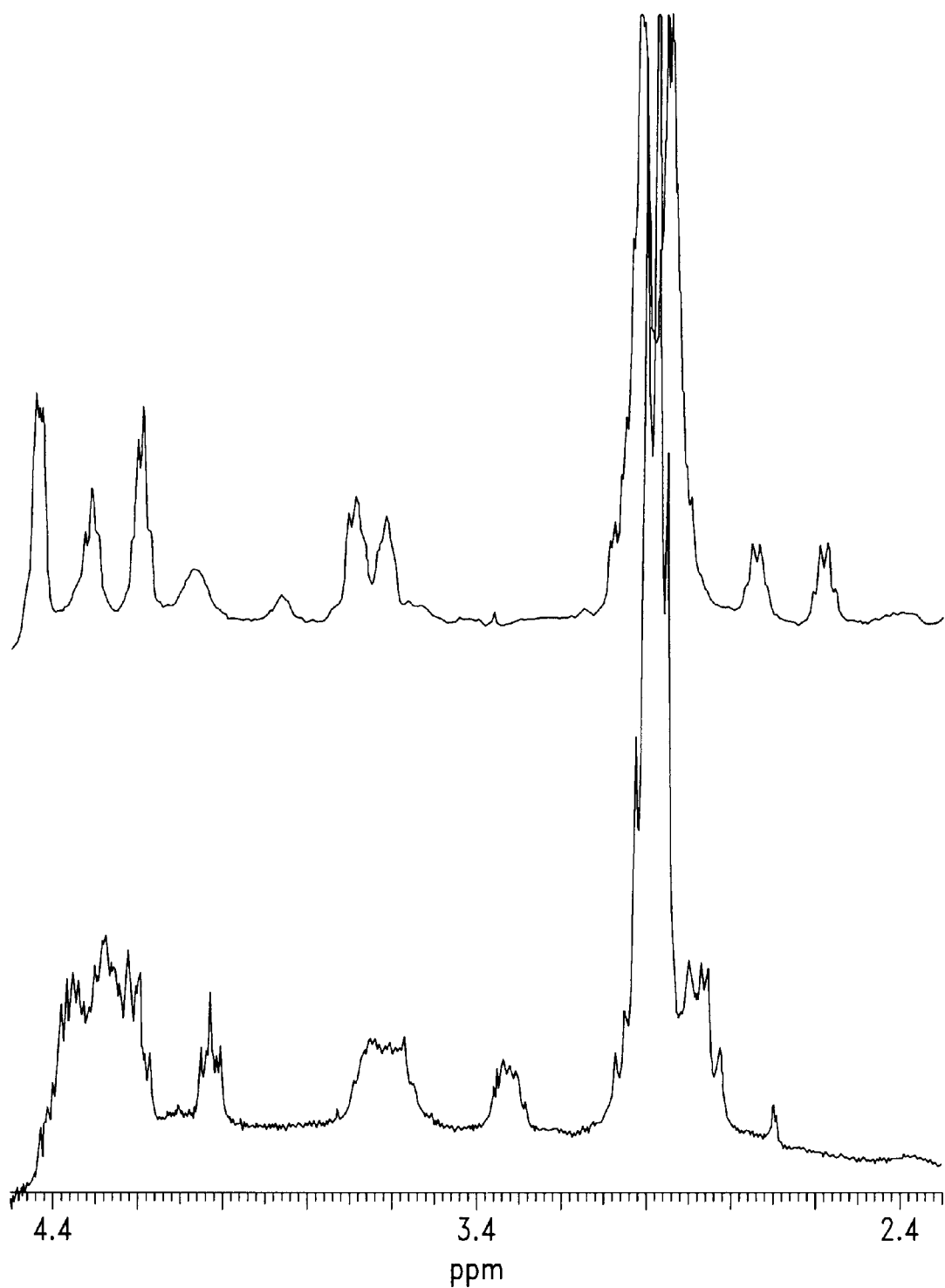
Figure 4A:
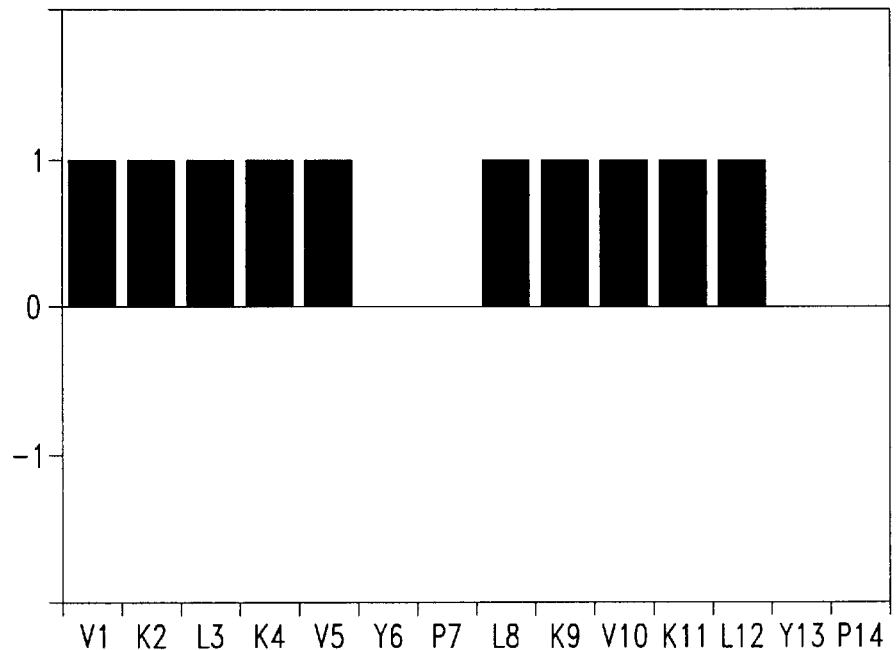
FIGS. 4(A–D) show chemical shift index analysis of GS14 and representative GS14 diastereomers. The chemical shift index was calculated as described by Wishart et al. (1992) for GS14 and selected diastereomers, and plotted as a function of sequence. Plots are for GS14 (A), GS14V1 (B), GS14K2 (C) and GS14V10 (D).
Figure 4B:
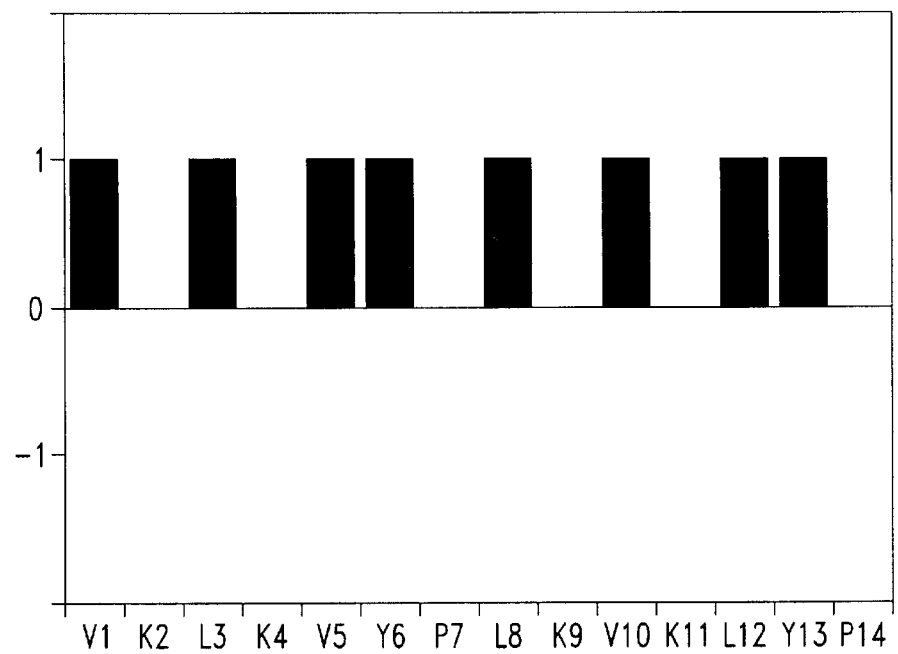
Figure 4C:
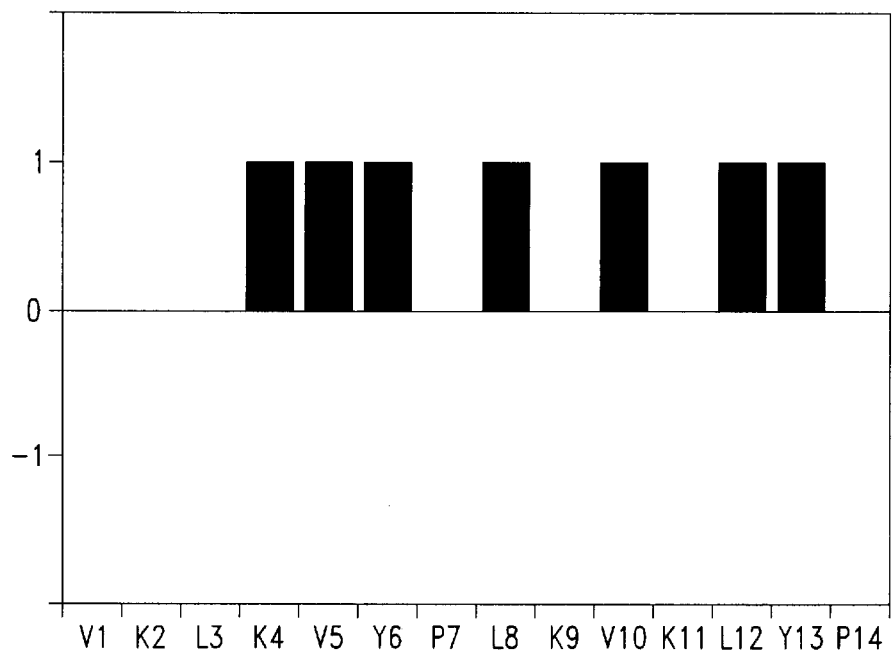
Figure 4D:
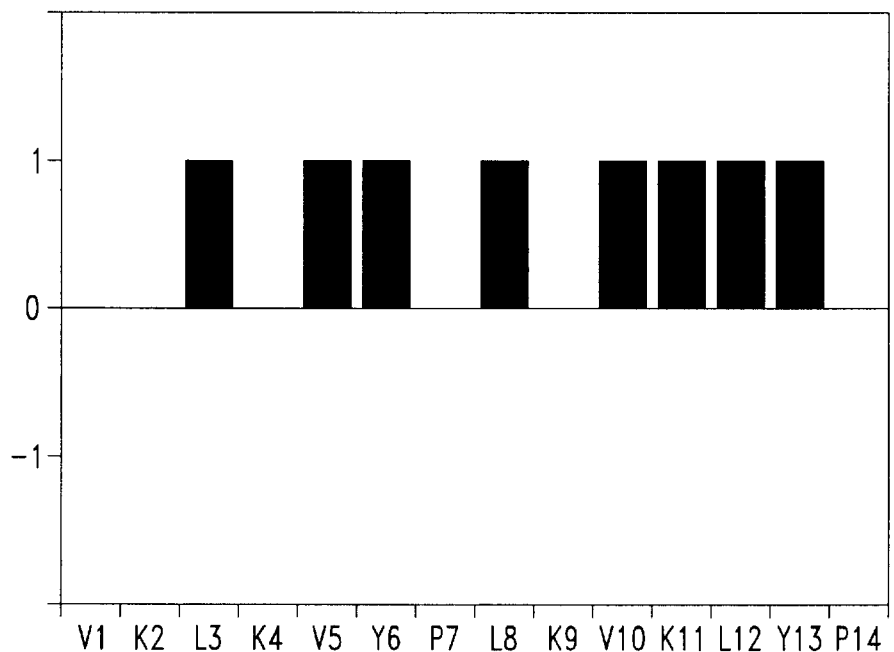

Comparison of the Hα regions (FIG. 3B) again shows the symmetry in GS14, where like residues give well separated and like chemical shifts, unlike GS14K2. Hα chemical shift indicies were calculated for GS14 and a number of representative diastereomers, according known methods (Wishart, et al., 1992). Results are shown in FIGS. 4(A–D). Positive chemical shift values indicate downfield shifted resonances relative to random coil values, and a cluster of three or more continuous positive chemical shifts is indicative of β-sheet structure. It is apparent that the Hα chemical shifts for GS14 are all β-sheet-like within the predicted strands of the molecule and non-β-sheet chemical shifts in the predicted turns defined by the D-Tyr-Pro sequence.

It is clear from the chemical shift analysis of the diastereomers (FIGS. 3B, 3C and 3D) that the strands contain less β-sheet structure and the turns become more disrupted compared to GS14. All diastereomers exhibit this disrupted β-structure behaviour, however, it is noteworthy that the diastereomers differ in both the extent and location of disruption, indicating that all are different structurally.

(iii) Molecular Modelling of GS14

Figure 5:
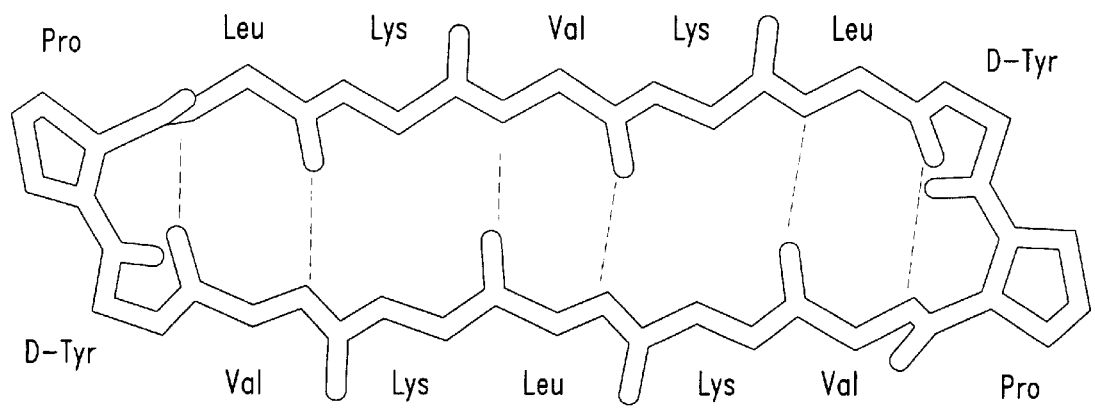
FIG. 5 shows a molecular model of GS14. The model was constructed to contain β-sheet dihedral angles for residues in the strands and two type II' β-turns defined by the Xaa-D-Tyr-Pro-Xaa sequence. An amide bond was formed between the N- and C-terminii, and energy minimization of the structure carried out. Shown is a top view of the backbone of GS14 indicating the positions of potential interstrand hydrogen bonds.

Both CD and NMR spectroscopies indicate that GS14 possesses a β-sheet structure similar to GS. A model of GS14 was constructed to contain the essential features as present in GS, namely, an antiparallel β-sheet structure with two type II' β-turns defined by the D-Tyr-Pro sequence. As shown in FIGS. 1 and 5, the incorporation of both the cyclic constraint (due to backbone cyclization of the peptide) as well as secondary structural constraints (β-sheet and turns) results in a highly amphipathic molecule where Val and Leu residues make up the hydrophobic face and Lys residues make up the basic face of the molecule. There are potentially six hydrogen bonds which can be formed to stabilize the β-sheet structure of GS14 located between all Val and Leu residues. The non-H-bonded sites are all occupied by Lys residues (FIG. 5).

(iv) Reversed-Phase HPLC Analysis

Figure 6:
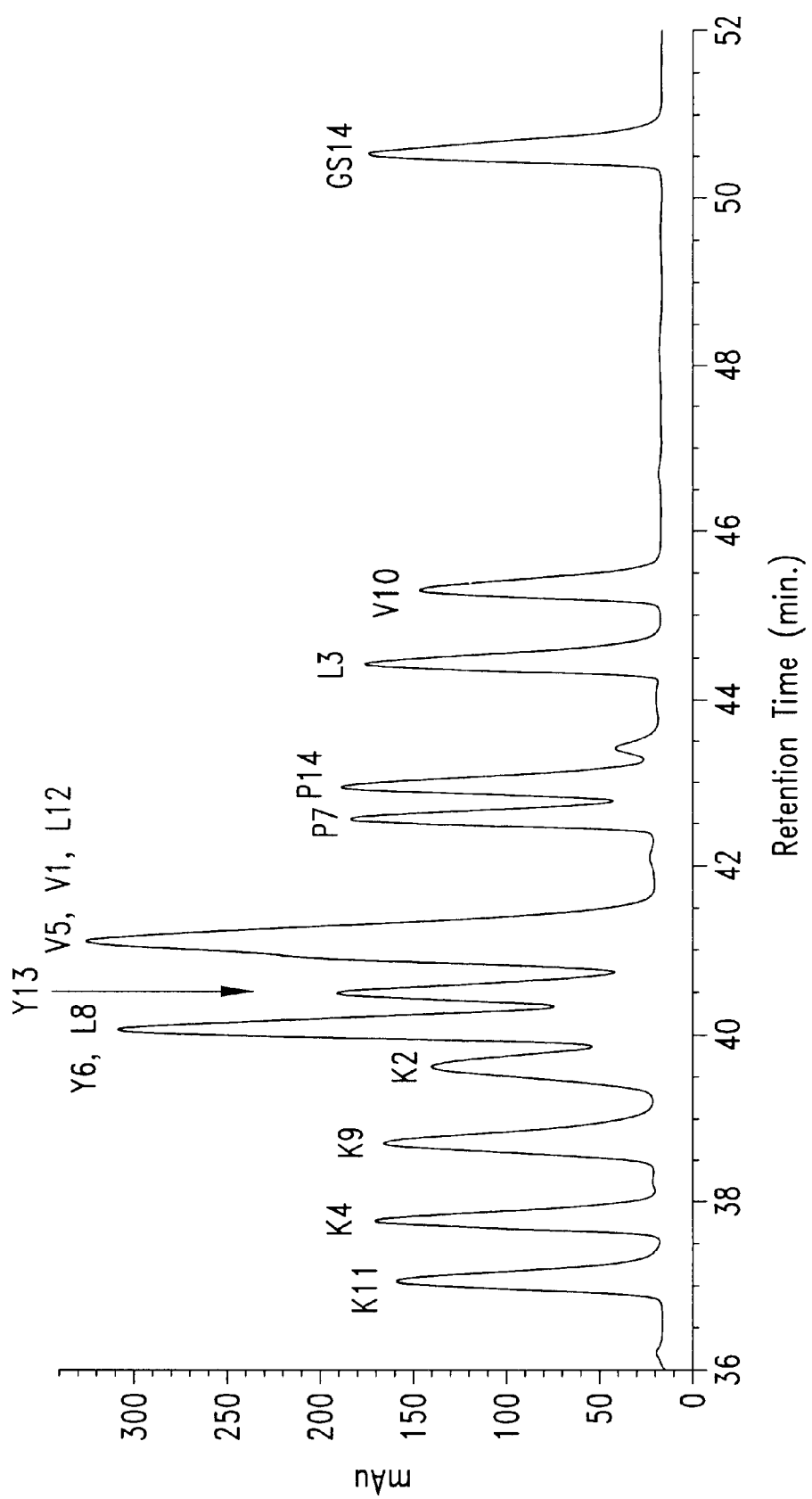
FIG. 6 shows reverse-phase HPLC separation of GS14 and single residue substitution diastereomers.

Retention time on reversed-phase HPLC can be used as a measure of peptide hydrophobicity (Parker, et al., 1986; Guo, et al., 1986). It is well known however that the formation of a hydrophobic binding domain due to peptide structure can affect peptide interactions with reversed-phase matrices; this effect has been observed both with α-helical peptides and β-sheet peptides (Zhou, et al., 1990; Rothemund, et al., 1996; Krause, et al., 1996; Wishart, et al., 1996). GS14 and the GS14 diastereomers have exactly the same composition and sequences, and therefore all have the same intrinsic hydrophobicity. Any differences in retention time are due to their effective hydrophobicity, or in other words, the ability of the peptide to form a hydrophobic binding domain, and present this hydrophobic face to the HPLC matrix. Shown in FIG. 6 is the reversed-phase HPLC separation of a mixture of GS14 and fourteen exemplary single residue substitution diastereomers tested. There is a wide range of retention times observed for the analogs and all have a lower retention time than GS14.

As seen from the model of GS14, the parent molecule which exists in a β-sheet conformation has a large hydrophobic face with six hydrophobic residues on one face of the molecule. Those diastereomers which have a higher retention time by HPLC analysis can present a greater hydrophobic face to the reversed-phase matrix, which is dependent on their ability to achieve an amphipathic structure and hence a β-sheet conformation. Analogs with a lower retention time cannot present as great a hydrophobic face due to the greater disruption of β-sheet structure, and hence greater disruption of amphipathicity. The extent of β-sheet disruption is dependent on the position of the substitution, with substitutions in sites comprising the non-H-bonded sites (Lys residues in this case) having a greater effect of β-sheet disruption compared to substitutions in sites comprising the H-bonded sites (Val and Leu) as can be seen from the retention profile shown. Reversed-phase analysis of the diastereomers as performed here is a measure of the ability to induce an amphipathic nature and β-sheet structure in the present analogs, and is therefore a measure of effective hydrophobicity.

b. Biological Properties of GS14 Enantiomeric Analogs (i) Interaction Between GS14 Distereomers and Bacterial Outer Membranes In studies carried out in support of the present invention, interaction between GS14 diastereomers and the bacterial outer membranes was assessed by monitoring the displacement of lipopolysaccharide-bound dansyl-polymyxin B by the peptides (Moore, et al., 1986). The lipopolysaccharide (LPS) binding affinity of GS14 is extremely strong, approaching that of polymyxin B itself whereas all the diastereomers have lower affinity (Table 1). Further, a good correlation was observed between binding affinity and retention time on reversed-phase HPLC (FIG. 7), with those peptides having a longer retention time exhibiting higher affinity for LPS. This indicates that those peptides which have the ability to present a greater hydrophobic face also bind more tightly to LPS, suggesting that binding to LPS in the present analogs is driven by hydrophobicity.

The binding affinity of GS is lower than all the diastereomers although GS has the greatest retention time on reversed-phase HPLC, showing that the increased relative number of basic residues (compared to GS) may also play a role in binding the outer membranes. Thus, both the number of hydrophobic residues as well as the number of positive charges were important in LPS binding.

(ii) Hemolytic Activity

Figure 8:
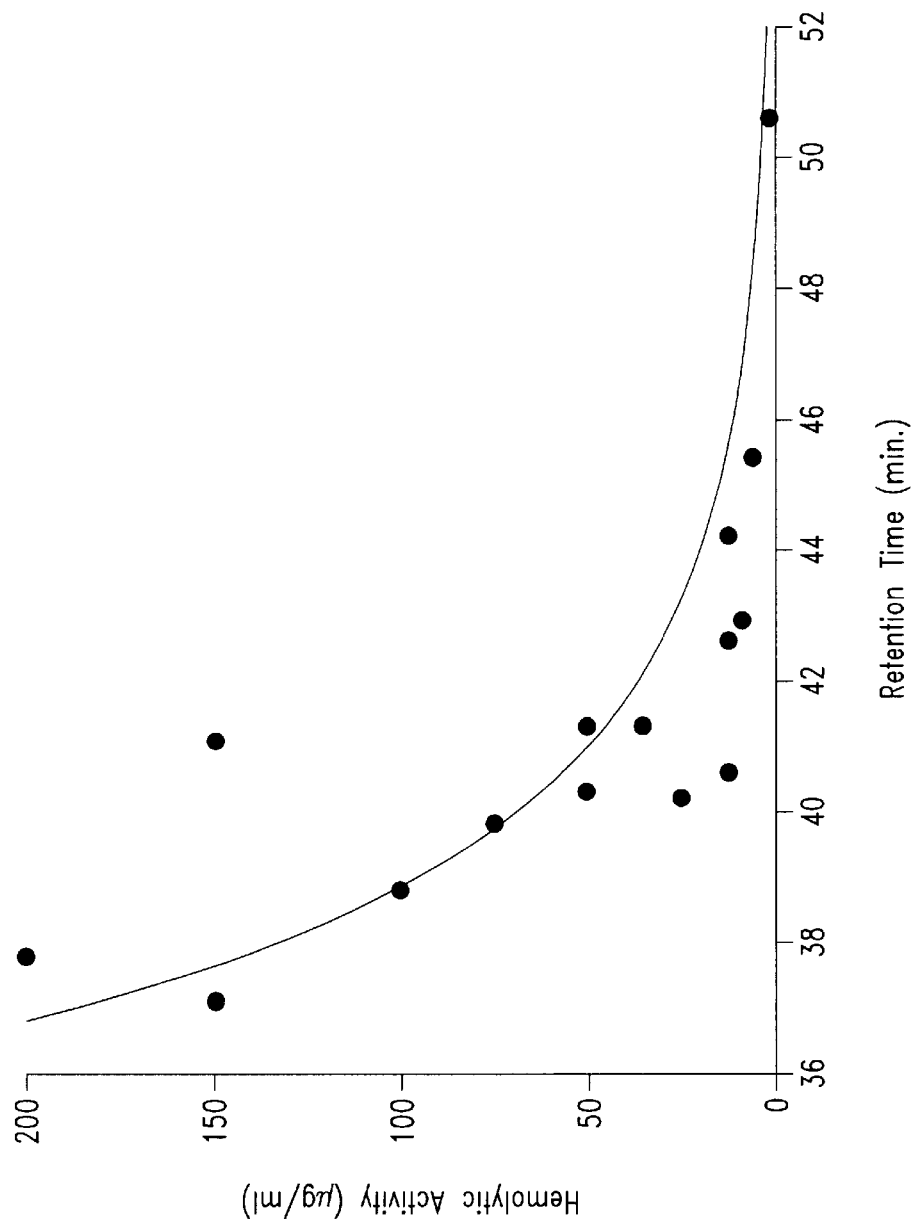
FIG. 8 shows a plot of hemolytic activity of GS14 diastereomers as a function of effective hydrophobicity (HPLC retention time).

It is demonstrated above that enantiomeric substitutions within the framework of GS14 affect structure as well as the interaction with the outer membrane of bacteria. As mentioned previously, GS14 exhibits extremely high hemolytic activity against human erythrocytes. Shown in Table 1 is the hemolytic activity of the diastereomers. As shown, there is a wide range of activities, ranging from activity similar to GS14, to greatly reduced hemolytic activity. As shown in FIG. 8, there is a relationship between hemolytic activity and effective hydrophobicity. Those analogs which are able to present a greater hydrophobic face are also more hemolytic, suggesting that high hydrophobicity is responsible for high hemolytic activity in GS14. Most significantly however, in the least hemolytic single substitution diastereomer, GS14K4, hemolytic activity was reduced more than 130-fold compared to the parent GS14. Hemolytic activity was even further reduced in those diastereomers containing either two or four enantiomeric substitutions (see Table 1).

(iii) Gram Negative Activity

Table 2 shows antimicrobial activity of the diastereomers against a range of gram negative microorganisms. Antibacterial activity was measured according to methods well known in the art, as described in Example 5.

Figure 7:
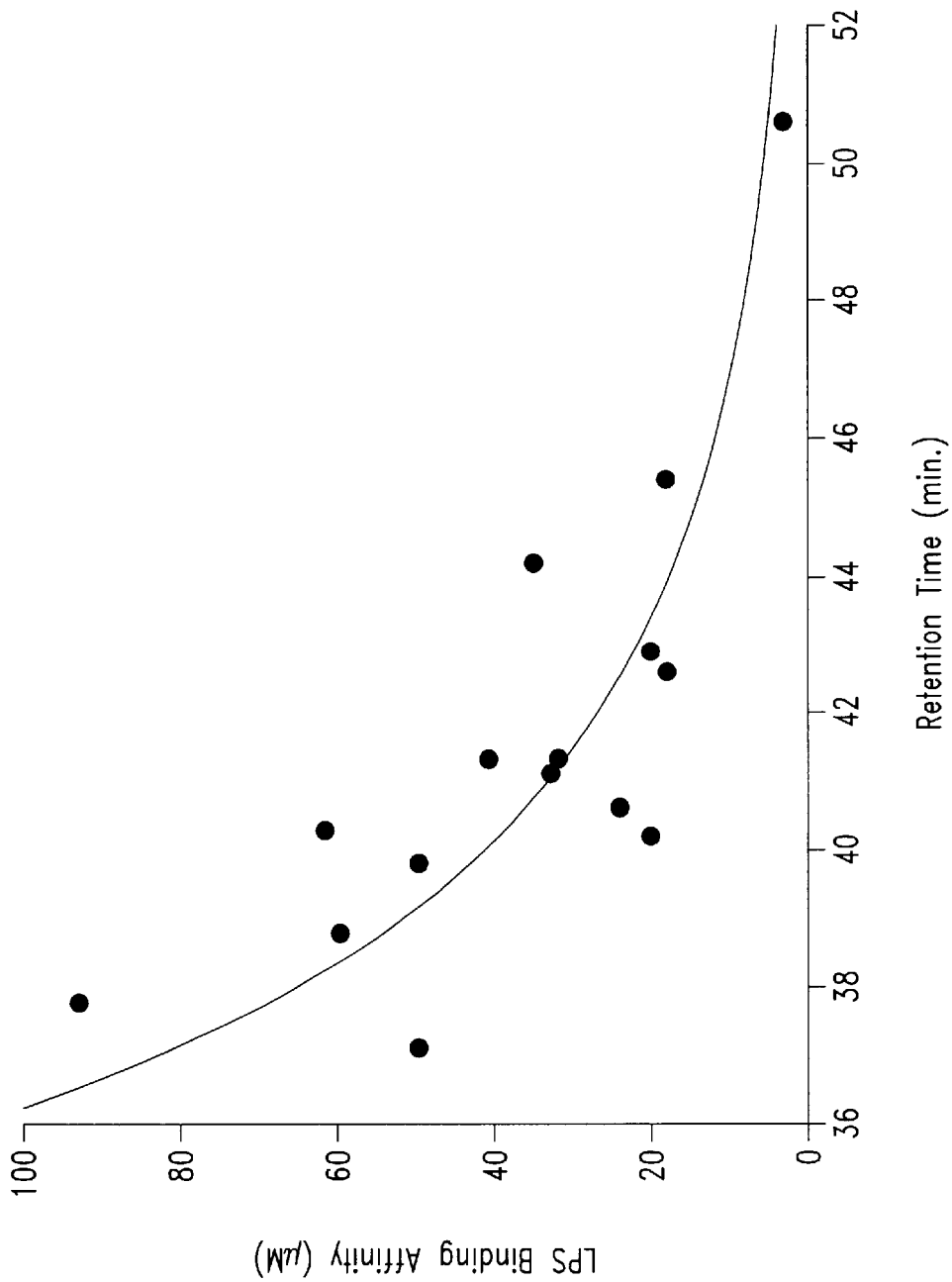
FIG. 7 shows a plot of LPS binding affinity of GS14 diastereomers as a function of effective hydrophobicity (HPLC retention time).

While GS14 showed little if any significant anti-microbial activity against the gram negative microorganisms tested, the majority of diastereomers exhibit at least some activity against most of these microorganisms, with some analogs displaying very strong activity. Shown also in Table 2 is the therapeutic index of the diastereomers, a measure of specificity of the peptide for the microorganism over human erythrocytes. It is apparent that GS14 has an extremely low therapeutic index, a value of less than 0.01, indicating that it has much greater activity against erythrocytes than gram negative microorganisms. Most of the diastereomers tested in support of the present invention exhibit an increase in therapeutic index, with a number of these showing a substantial improvement in specificity (e.g., indicies such as 50 and 65). This increase in therapeutic indicies represents a substantial increase in specificity compared to GS14, an increase greater than 6,500-fold for GS14K4 with two separate microorganisms (*P. aeruginosa* H188 and *E. coli* DC2). This increase in specificity is due to both enhanced antimicrobial activity coupled with decreased hemolytic activity of the diastereomers. The activity and specificity of GS is also shown in Table 2 for comparison. The best GS14 diastereomer, GS14K4, exhibits not only greater activity but also greater specificity than GS for the majority of gram negative microorganisms. For GS14K4 the therapeutic indicies for all microorganisms tested are in the range of 16- to 32-fold greater than GS itself. There is a relationship between both activity and bacterial specificity with effective hydrophobicity. For all microorganisms tested, the antimicrobial activity increases with decreasing retention time on RP-HPLC. Without committing to any particular theory, this may be a reflection of the tighter binding to the outer membrane by analogs with higher retention times, as illustrated in FIG. 7, which may decrease their ability to penetrate to, and accumulate at, their site of action on the inner membrane. The increased antimicrobial activity coupled with decreased hemolytic activity (FIG. 8) with lower retention time results in substantial increases in the therapeutic index compared to GS14. Diastereomers containing either two or four enantiomeric substitutions were generally less active against gram negative microorganisms than the best single substitution analogs, and they also exhibited lower hemolytic activity. This may indicate the existence of a minimum requirement of inducibility of a hydrophobic face for both hemolytic and antimicrobial activities.

(vi) Gram Positive and Antifungal Activity

The activity of the diastereomers against gram positive microorganisms and yeast is shown in Table 3. GS14 has low potency or is inactive (MIC>200 μg/ml) against four of the gram positive microorganisms tested but exhibits strong activity against both *E. faecalis* and *Corynebacterium xerosis*. All of the single residue substitution diastereomers also exhibit strong activity against both *E. faecalis* and *C. xerosis*. They also display strong activity against *S. epidermidis* and moderate activity against the remainder of the gram positive microorganisms tested. While GS14 has very low potency or is inactive against *C. albicans*, all the diastereomeric exhibit antifungal activity ranging from strong to moderate. Coupled with the decreased hemolytic activity of the diastereomers, there is again a large increase in therapeutic index relative to GS14 for all the microorganisms. Increases in specificity are in the order of 100-fold with *E. faecalis*, 1,000-fold for *C. xeroses*, 3,000-fold for *C. albicans* and 10,000-fold for *S. epidermidis* for the best diastereomers (GS14K4 and GS14K11).

Figure 9:
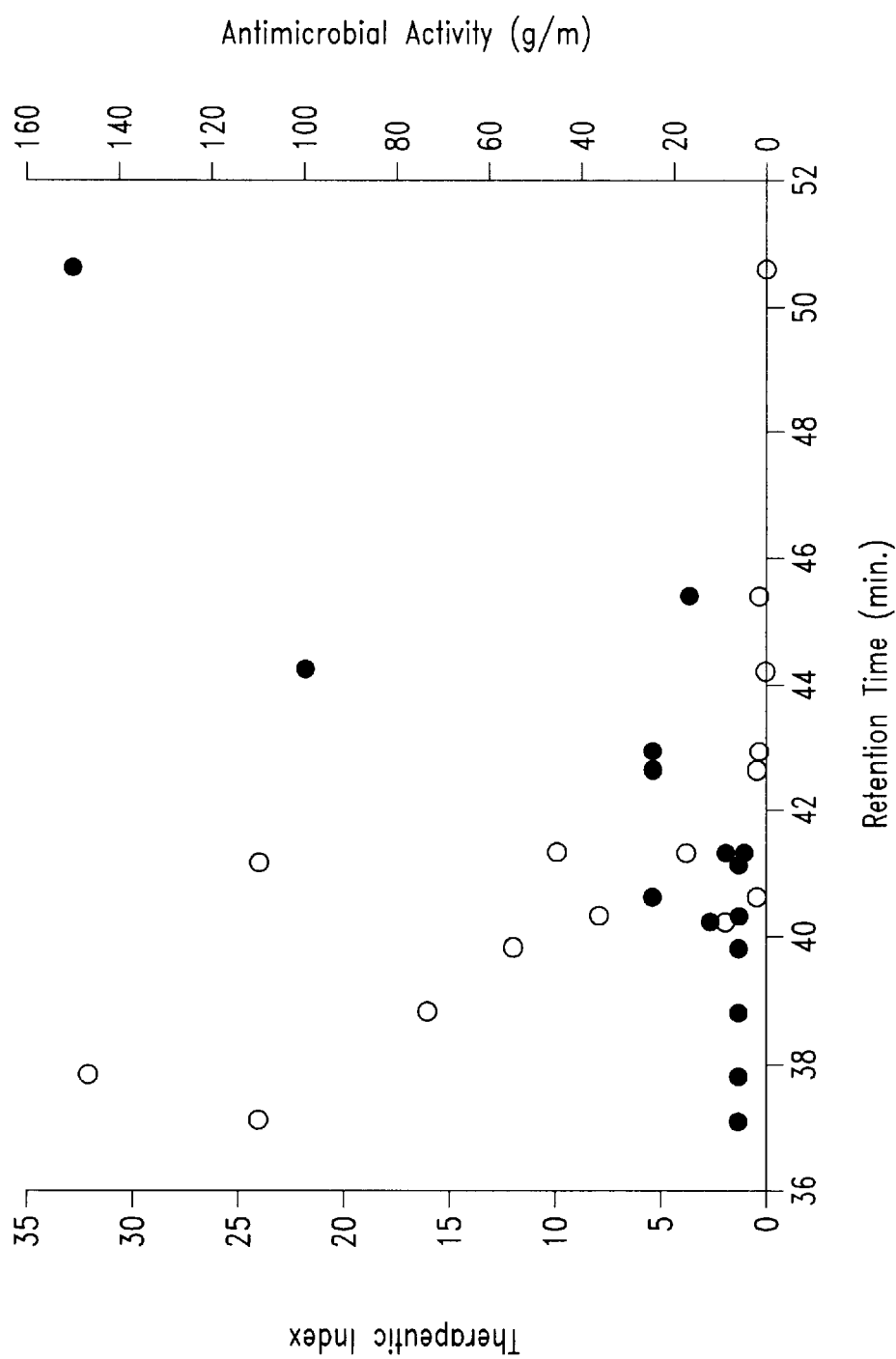
FIG. 9 shows antifungal activity and specificity of GS14 diastereomers. The antifungal activity (closed circles) and the therapeutic index (open circles) of the single residue enantiomeric GS14 substitution analogs described herein are plotted as a function of retention time on reversed-phase HPLC.

There is a relationship between activity and specificity with effective hydrophobicity, as shown in FIG. 9. For those microorganisms against which GS14 exhibited antimicrobial activity (*E. faecalis* and *C. xeroses*) the activity remains constant in all the analogs, but the therapeutic index is increased due to reduction in hemolytic activity. GS14 diastereomers exhibited an increase in both activity and therapeutic index with decreasing retention time on RP-HPLC with respect to GS14-insensitive organisms. The most active diastereomers display activities which are essentially equal to GS itself for three of the gram positive microorganisms and yeast, but with therapeutic indicies in the order of 10-fold higher than GS due to reduced hemolytic activity.

From the foregoing studies, with respect to activity against gram negative organisms, diastereomers at single positions 1, 2, 4, 5, 8, 9, and 11 showed markedly enhanced properties with respect to GS14 and, generally enhanced spectrum of activity compared to GS. With respect to activity against gram positive organisms, diastereomers at positions 1, 2, 4, 5, 7, 8, 9, 10 11, and 12 showed enhanced activity with in comparison to GS14 and activity that is comparable or only slightly less than the activity shown for GS. It is therefore an important discovery of the present invention that such GS14 diastereomers exhibit antimicrobial activity not observed in the parent compound having the same conformational properties as GS, and a wider spectrum than GS. For certain individual organisms, as shown, diastereomers exhibited improved activity compared to GS.

The implications of the activity profiles are discussed further in the Utility section, below.

2. Same Class Substitutions

According to another important feature of the invention, it is recognized that antimicrobial peptides may be formed by substituting same class residues for the residues shown in the prototype peptides, such as the diastereomeric GS14 peptides discussed above. Further, according to another feature of the invention, it is appreciated that such substitution may result in further optimization of antimicrobial and/or therapeutic potential of such peptides. This section discusses how such substitution/optimization is achieved.

a. Petide Design

Specifically, by "same class" substitution is meant that, within the structure of a known active compound, substitution for any particular residue can be made with a residue having similar physicochemical parameters. Since peptides of the present invention are made up primarily of hydrophobic (class I) and basic (class II) residues, this means that substitution at sites containing a class I residue (such as a valine or a leucine) can be made using other members of class I family, which include, but are not limited to the hydrophobic amino acids alanine, valine, leucine, norvaline, isoleucine, norleucine, methionine, phenylalanine, tyrosine and tryptophan. Similarly, substitution at class II sites can be made by any member of the basic group of amino acids which include, but are not limited to lysine, arginine, ornithine, histidine, 2,4-diaminobutyric acid and 2,3-diaminoproprionic acid.

b. Hydrophobic Same Class Substitution Analogs

Examples of peptides having such substitutions are shown in Table 4 where active diastereomeric composition GS14K4 was used as a parent compound. In this context, the compound designated L3/A3 represents substitution of alanine residues for all the leucine residues of GS14K4. Other examples are also shown in the table.

Figure 10:
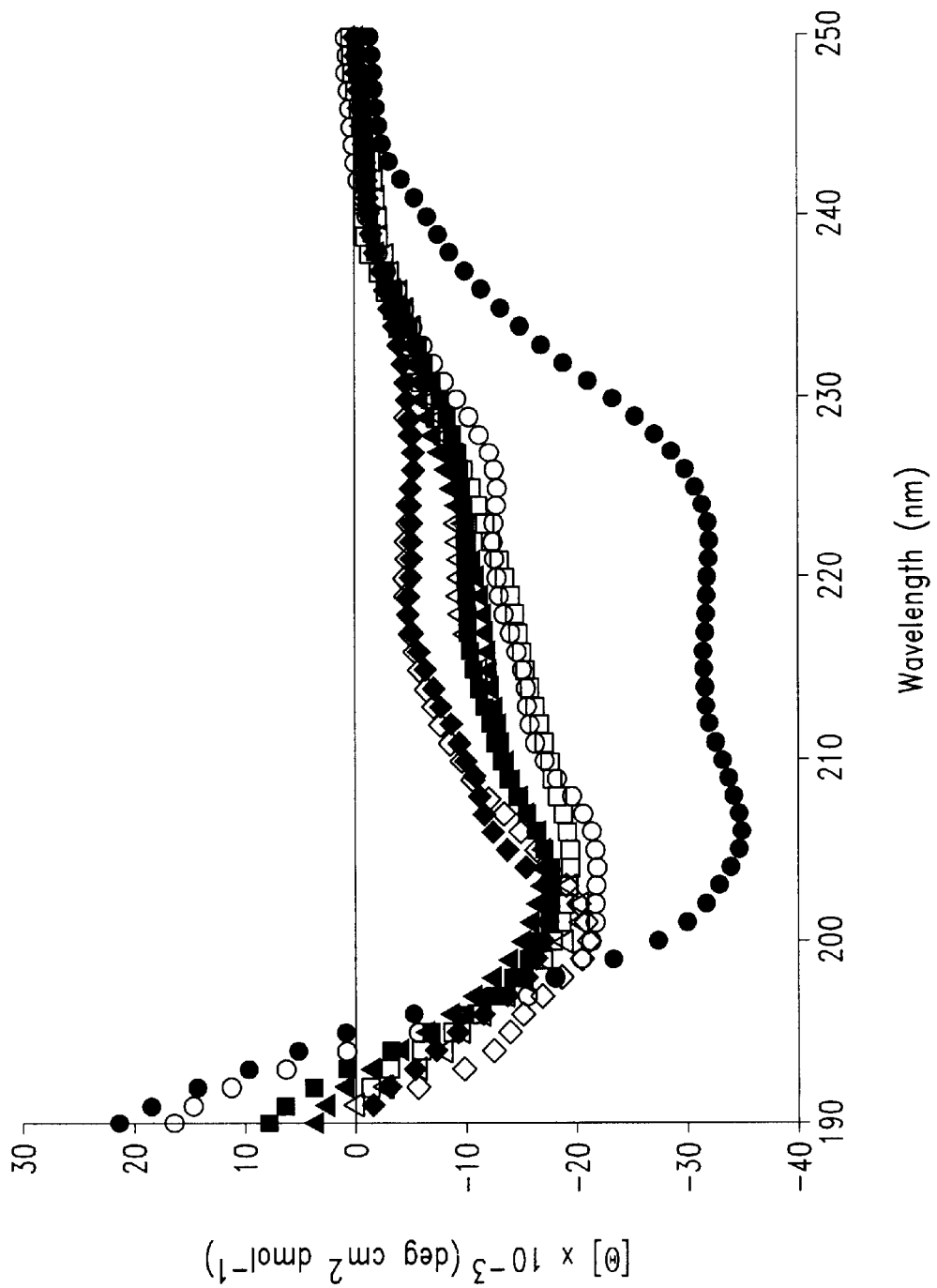
FIG. 10 shows CD spectra of GS14K4 and GS14K4 hydrophobicity analogs recorded in 5 mM sodium acetate buffer, pH 5.5, at 20° C. Samples were GS14, closed circles; GS14K4, open circles; Y2/F2, open squares; V3/L3, closed squares; L3/A3, open triangles; Y2/F2, V3/L3, closed triangles; V3L3/A6. open diamonds; V3/A3, closed diamonds.

In experiments carried out in support of the present invention, physicochemical and biological evaluations of these compounds were carried out essentially as described above, with reference to diastereomeric compositions. Circular dichroism studies on the compounds showed that the hydrophobic same class substitution analogs of GS14K4, whether more or less hydrophobic, exhibited CD spectra similar to GS14K4 indicating that all possess a similar disordered structure (FIG. 10).

As mentioned above, retention time on reversed-phase HPLC can be used as a measure of peptide hydrophobicity. As shown in Table 4, there is approximately a 10 min. difference in retention times between GS14 and GS14K4. These peptides have exactly the same composition and sequence, and therefore the same intrinsic or calculated hydrophobicity. The difference in retention times in this case is due to structural differences between the molecules and is a measure of the effective hydrophobicity, in other words, the ability of the peptide to present a hydrophobic face to the HPLC matrix.

Figure 11:
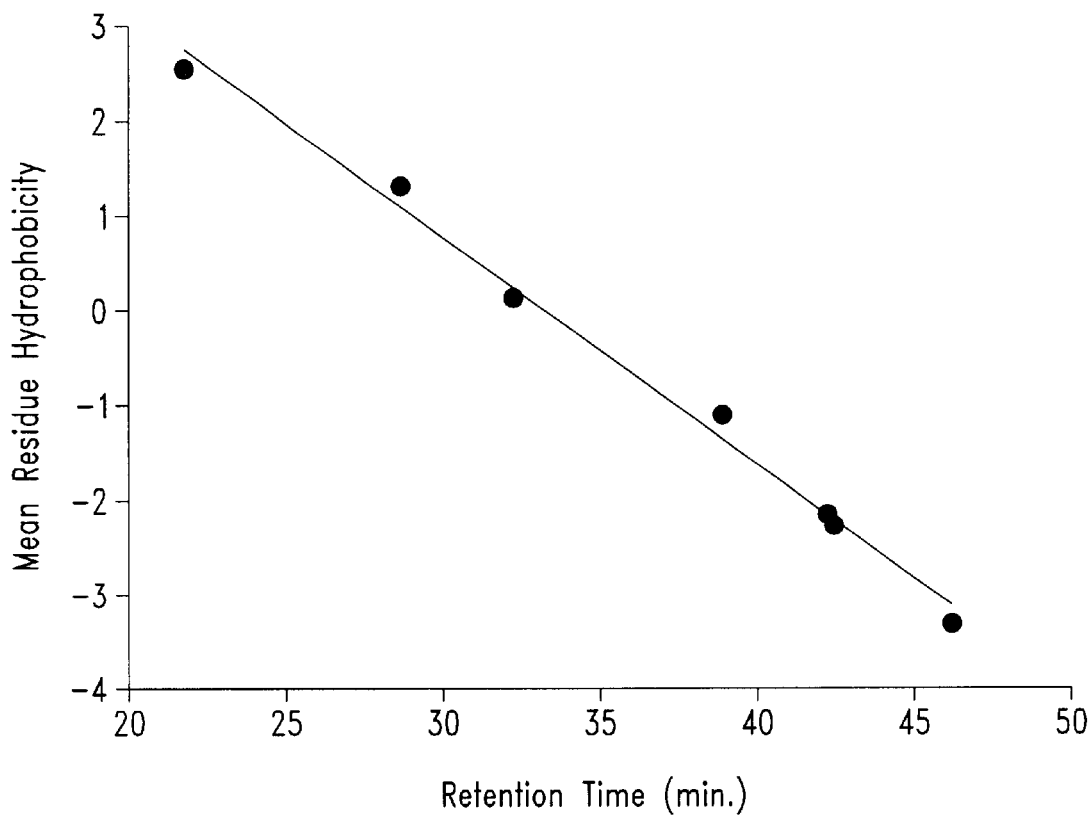
FIG. 11 shows a correlation between calculated and measured hydrophobicity of GS14K4 hydrophobicity analogs. The mean residue hydrophobicity was calculated using the HPLC-derived hydrophobicity scale of Parker et al. and the measured hydrophobicity was determined by retention time on RP-HPLC, as described herein.

Modulation of effective hydrophobicity in the same class hydrophobic analogs through residue substitutions in the framework of GS14K4 was carried out. A plot of the retention times of the hydrophobicity analogs against their calculated mean residue hydrophobicities (Table 4 and FIG. 11 yields a linear relationship (R=1.0) indicating that the analogs possess essentially similar structures and therefore only differ in intrinsic hydrophobicity. The changes in the intrinsic hydrophobicities of the analogs in a similar structural framework therefore result in changes in the effective hydrophobicity of the analogs.

The interaction of the peptides with the outer membranes of bacteria was investigated by monitoring the displacement of lipopolysaccharide-bound dansyl-polymyxin B by the peptides, as described above.

Figure 12:
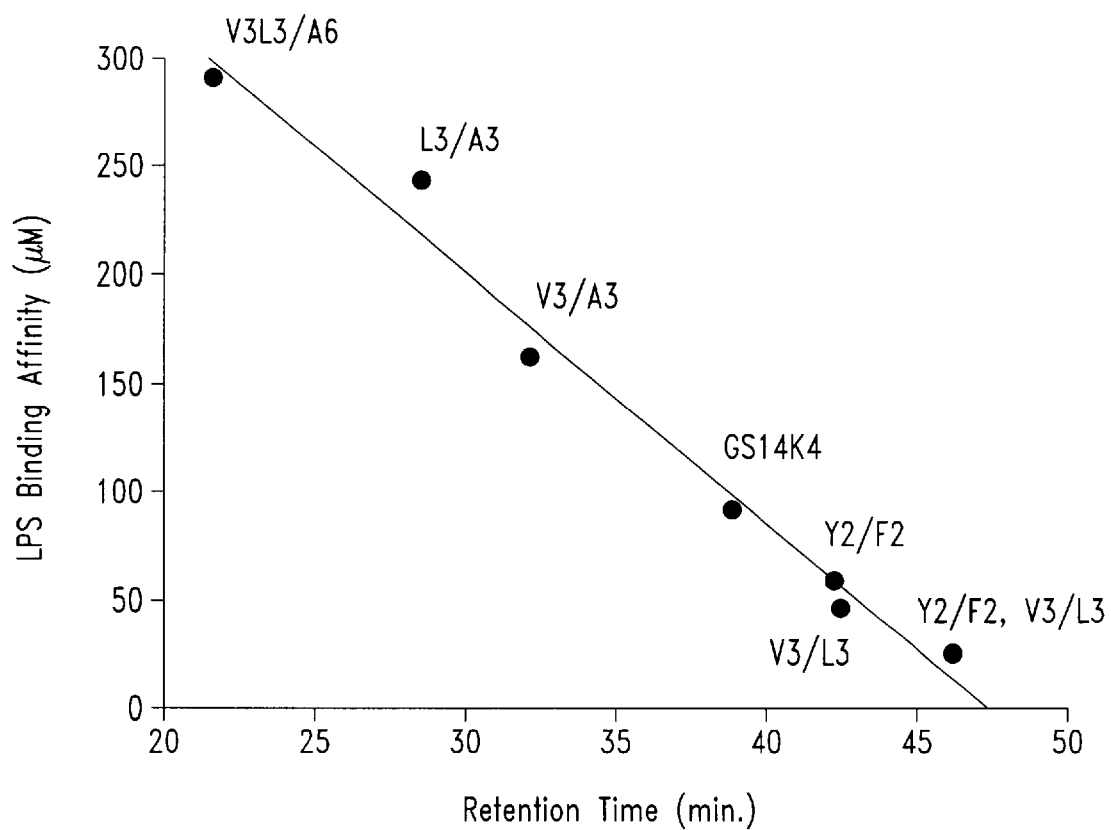
FIG. 12 shows a correlation between effective hydrophobicity and LPS-binding affinity in GS14K4 hydrophobicity analogs.
Figure 13A:
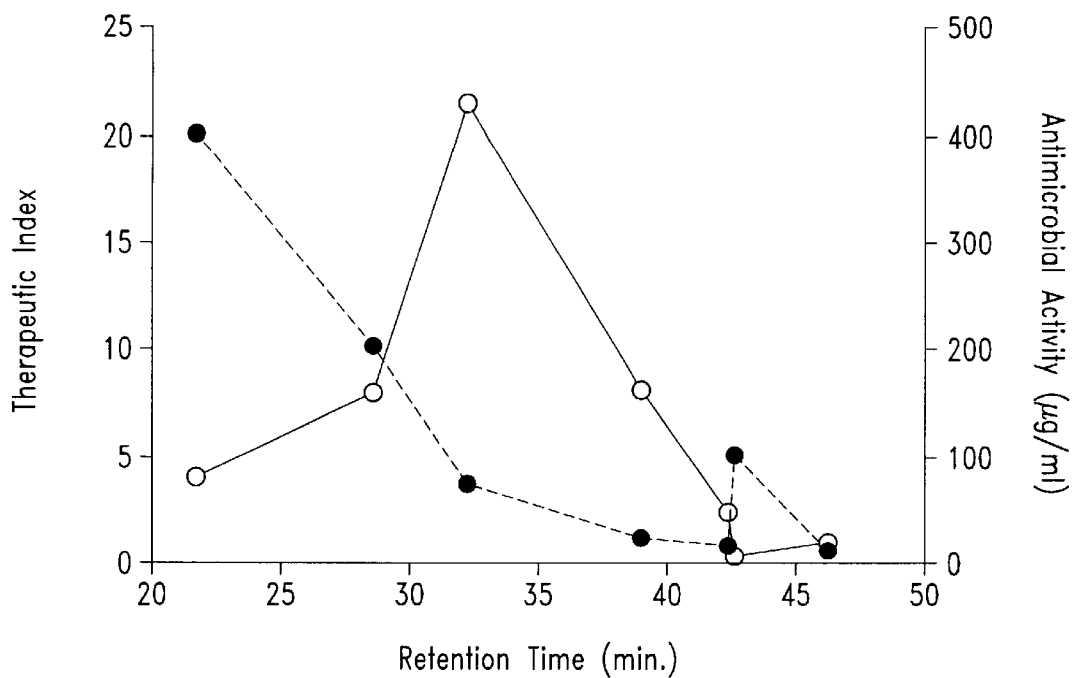
FIGS. 13 (A–F) show antimicrobial activity and microbial specificity of GS14K4 hydrophobicity analogs against gram negative microorganisms. The antimicrobial activity (closed circles) and the therapeutic index (open circles) of the GS14K4 analogs shown in Table 5 are plotted as a function of retention time on RP-HPLC. Plots are (A) *P. aeruginosa* H187; (B) *P. aeruginosa* H188; (C) *E. coli* UB1005; (D) *E. coli* DC2; (E) *S. typhinurium* C587; (F) *S. typhinurium* C610. A value of 400 µg/ml was used for values of >200 µg/ml in Table 5 for the plot as well as for calculation of the therapeutic index. For hemolytic activity values >800 µg/ml (Table 4) a value of 1600 µg/ml was used for calculation of the therapeutic index.
Figure 13B:
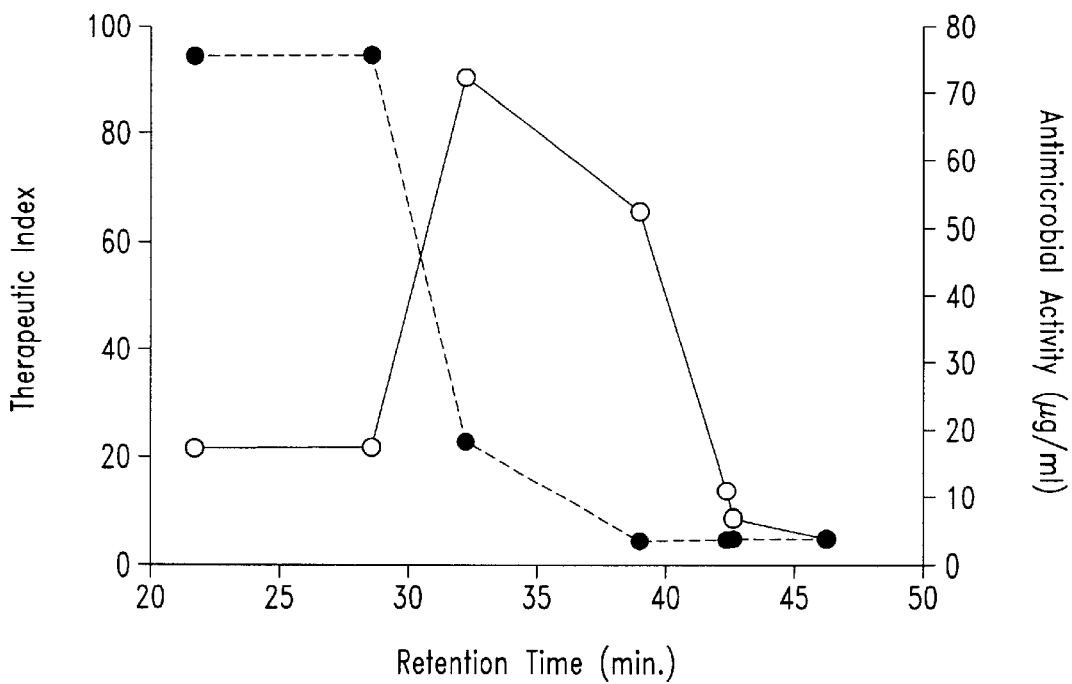
Figure 13C:
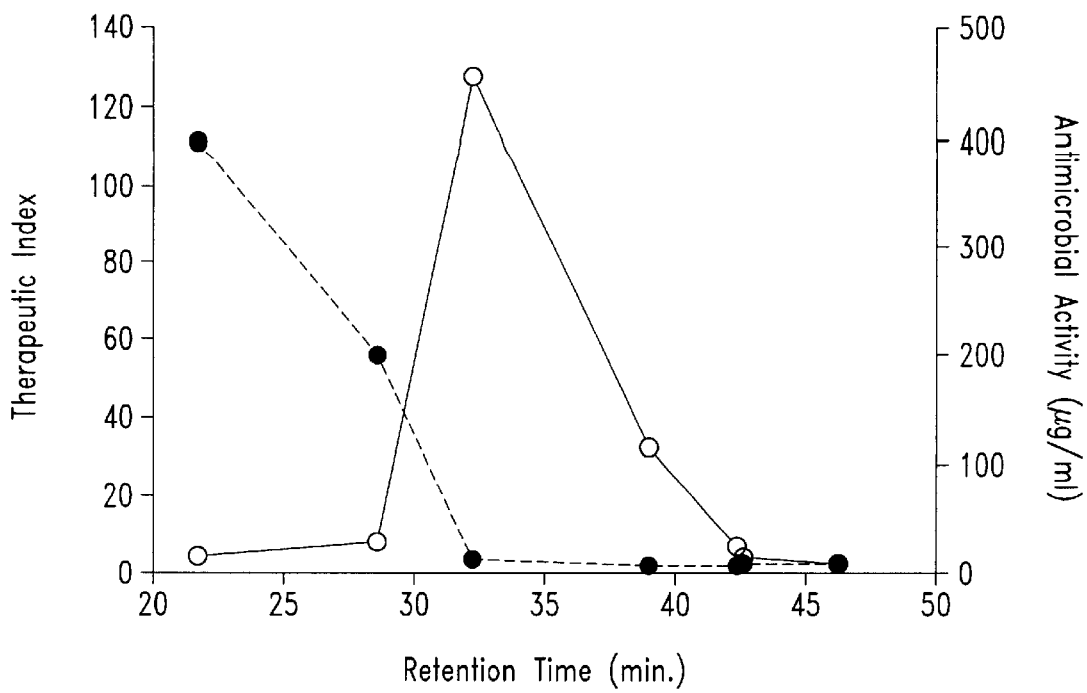
Figure 13D:
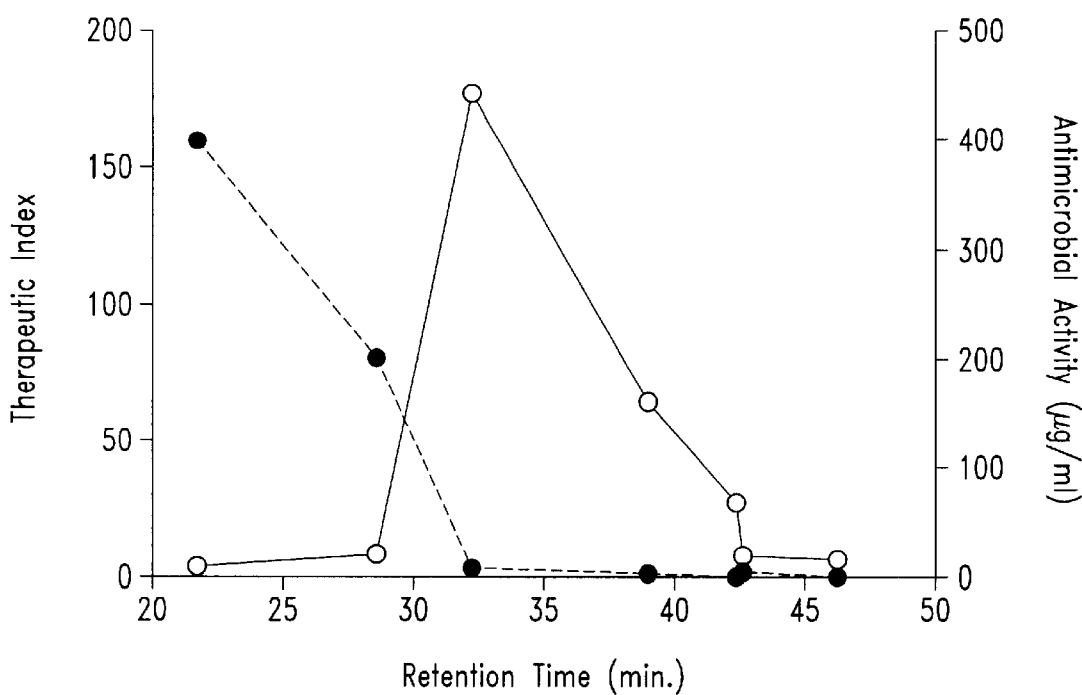
Figure 13E:
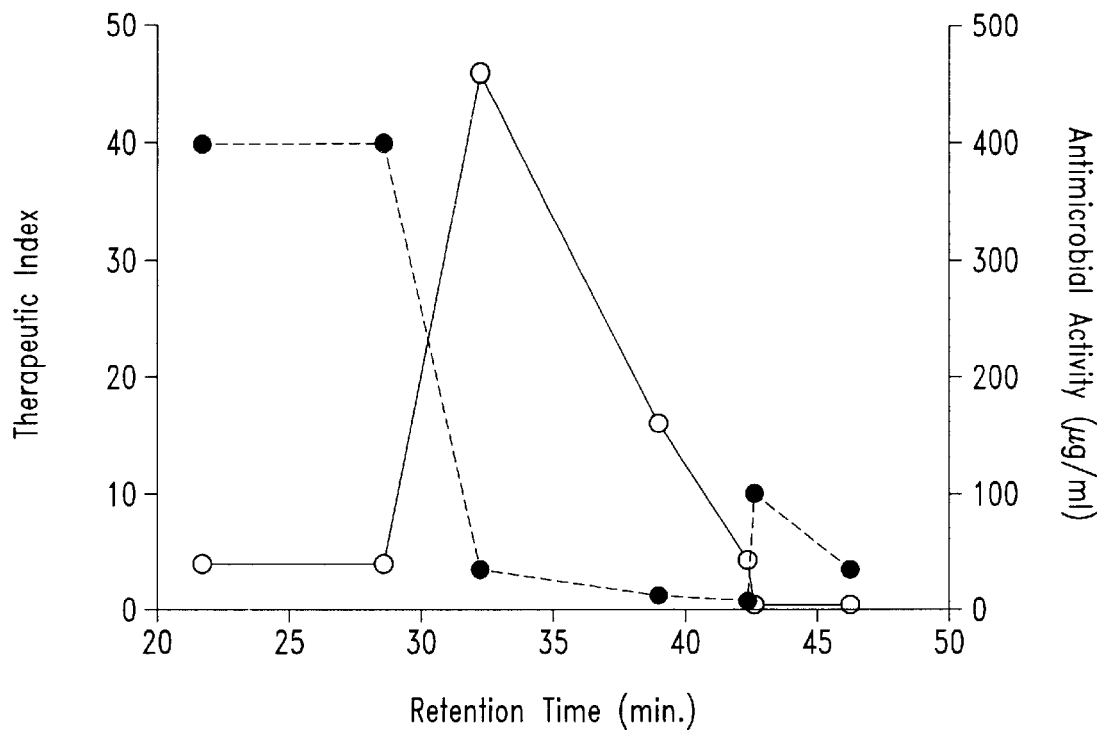
Figure 13F:
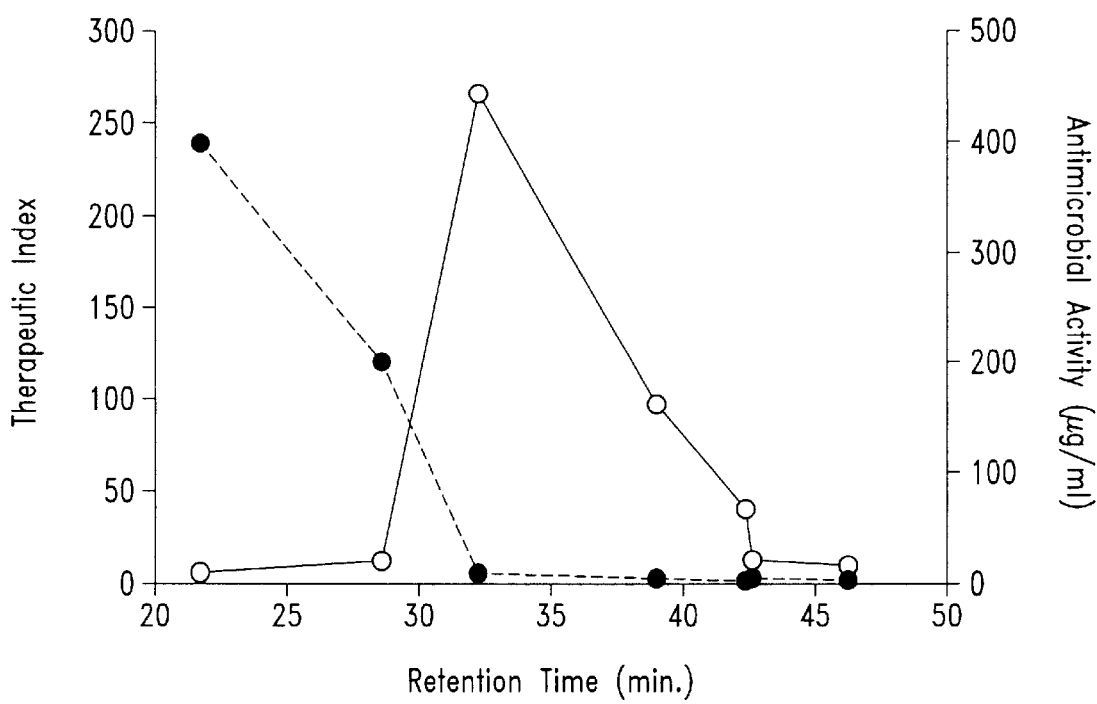
Figure 14A:
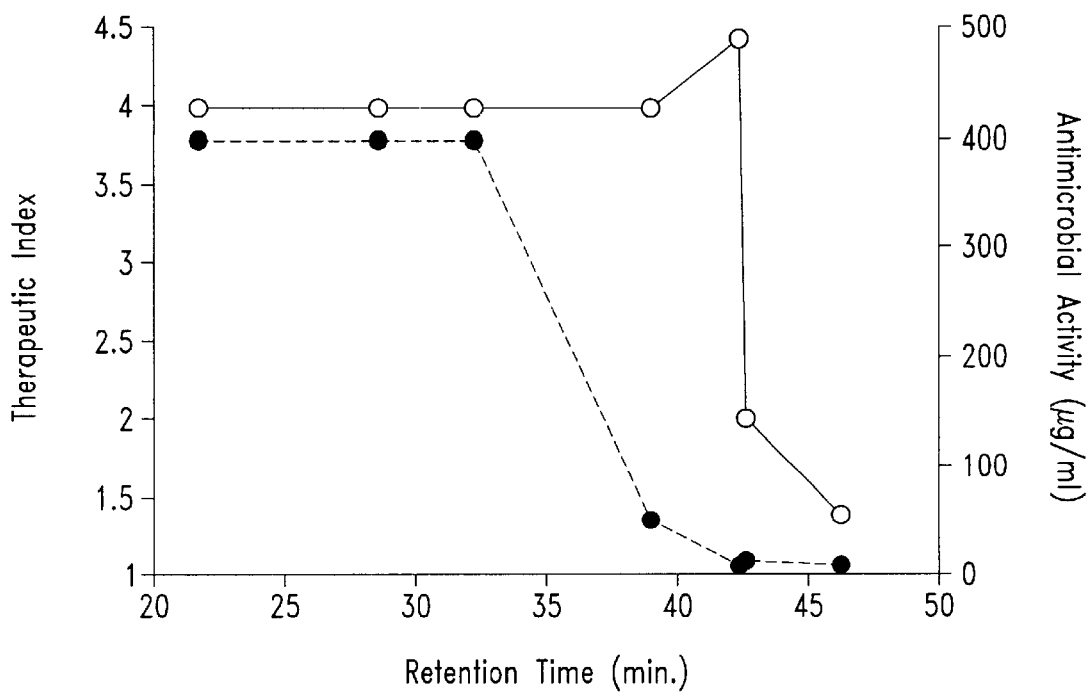
FIGS. 14 (A–F) show antimicrobial activity and microbial specificity of GS14K4 hydrophobicity analogs against gram positive microorganisms. The antimicrobial activity (closed circles) and the therapeutic index (open circles) of the GS14K4 analogs shown in Table 6 are plotted as a function of retention time on RP-HPLC. Plots are (A) *S. aureus* SAP0017; (B) *S. aureus* K147; (C) *S. epidermidis*; (D) *B.* subtilis; (E) *E. faecalis*; (F) *C. xeroses*. A value of 400 μg/ml was used for values of >200 μg/ml in Table 6 for the plot as well as for calculation of the therapeutic index. For hemolytic activity values >800 μg/ml (Table 4) a value of 1600 μg/ml was used for calculation of the therapeutic index.
Figure 14B:
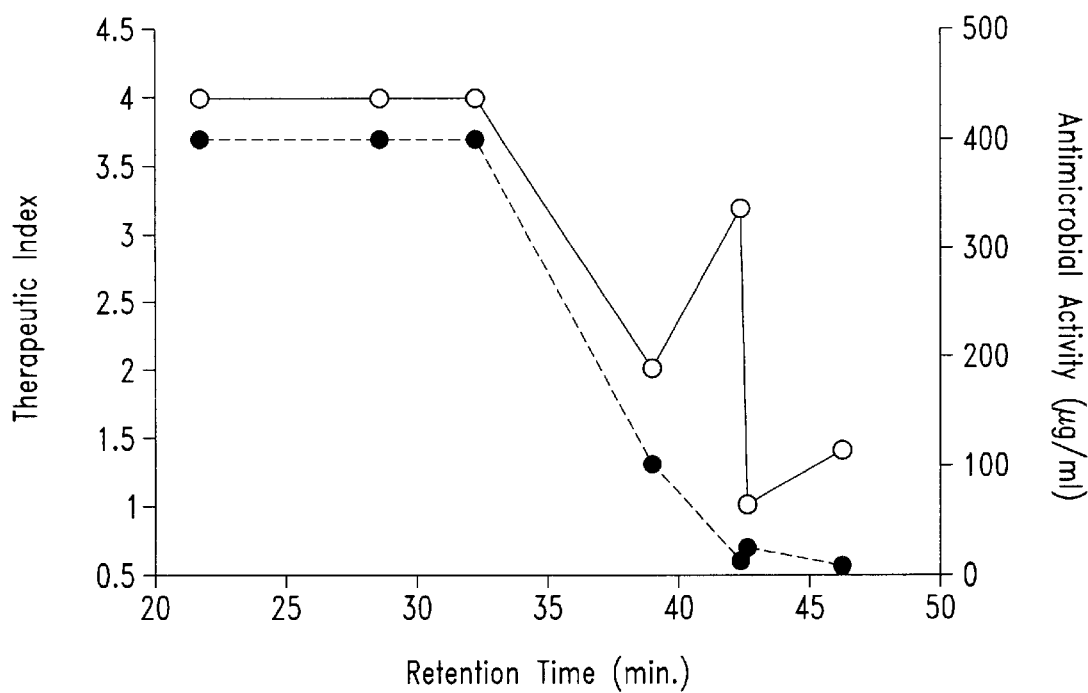
Figure 14C:
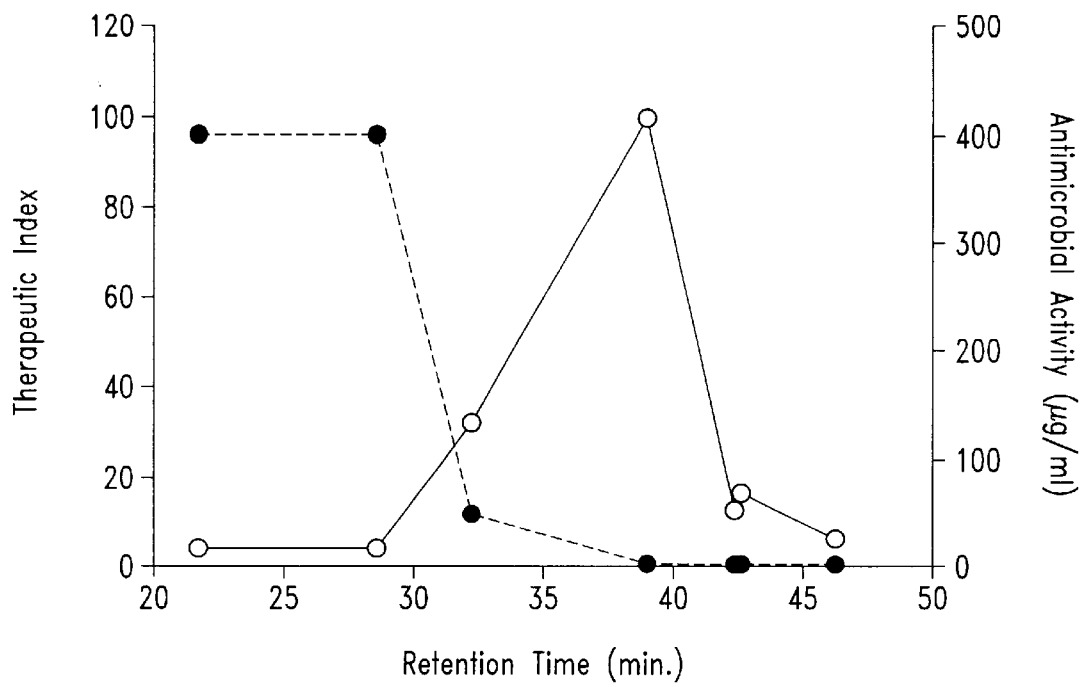
Figure 14D:
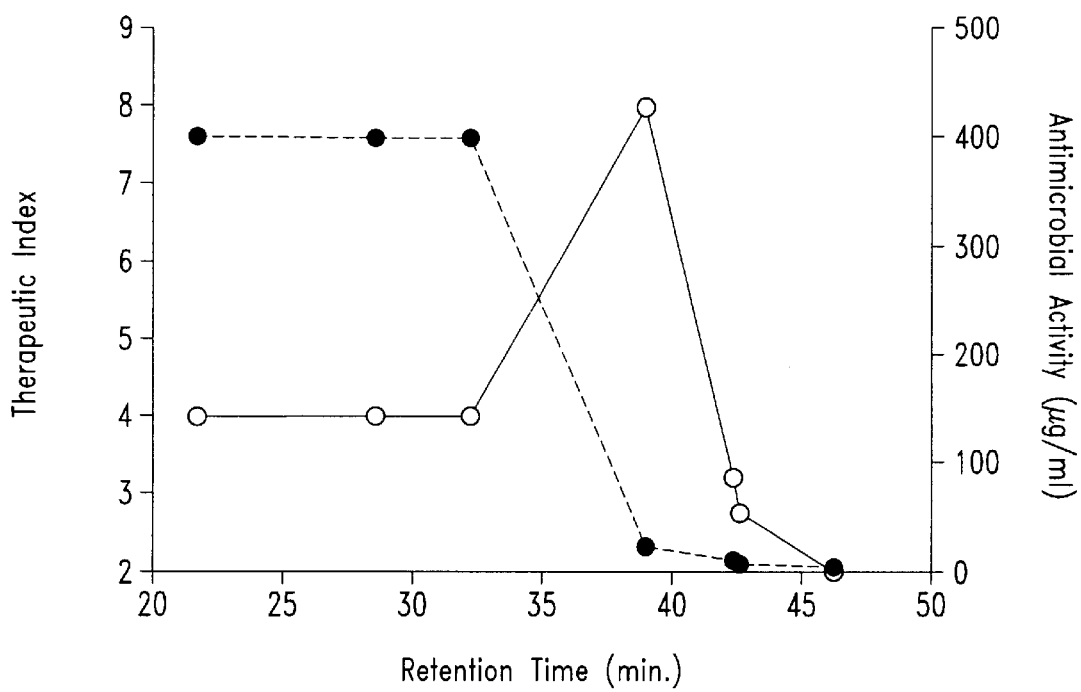
Figure 14E:
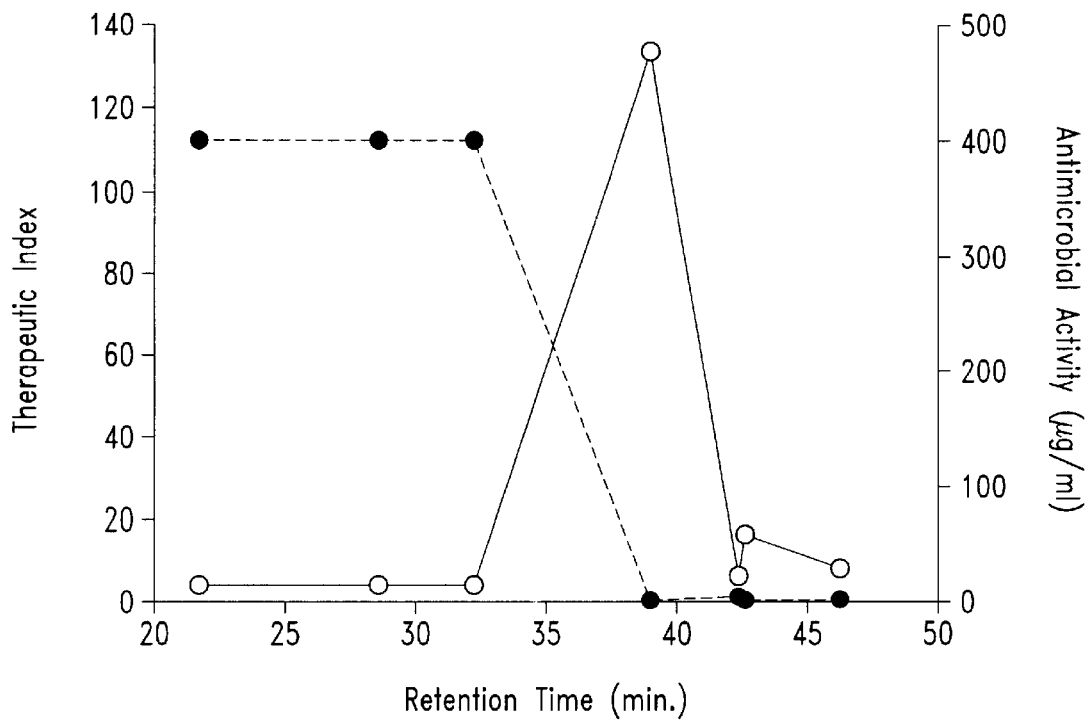
Figure 14F:
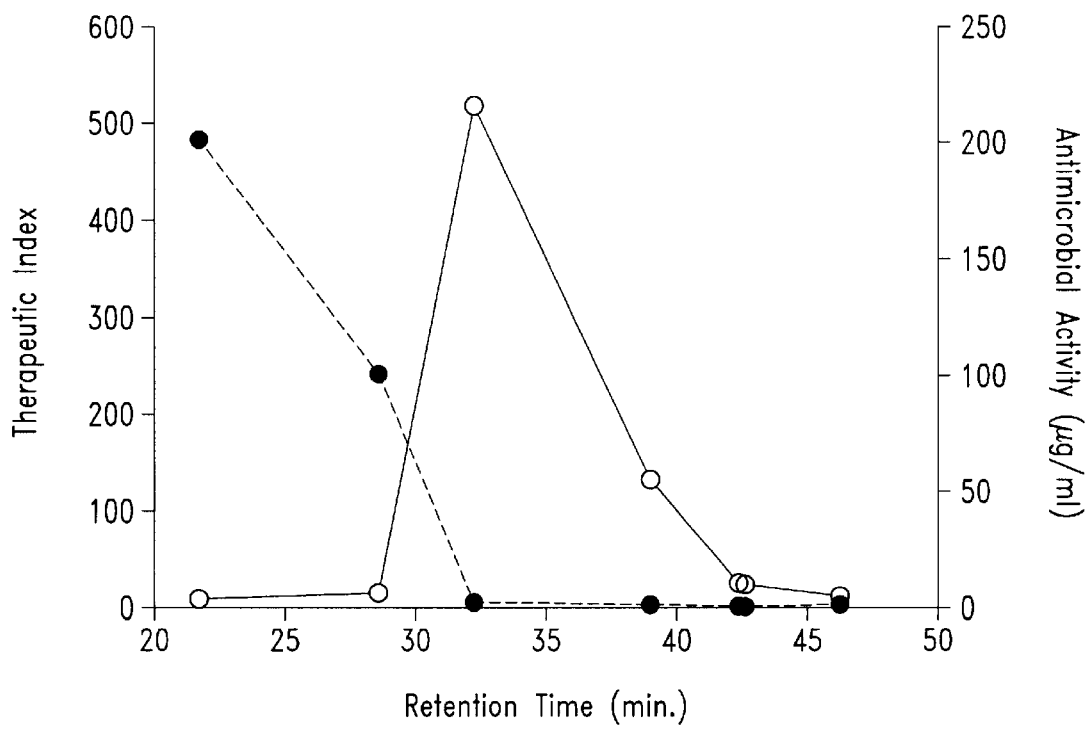

As with the diastereomers, studies carried out in support of the present invention revealed that the LPS-binding affinity of GS14 diastereomers showed a correlation with retention time. That is, those diastereomers with higher retention times (greater effective hydrophobicity) also exhibited higher affinity for bacterial outer membranes. This relationship is illustrated in FIG. 12. for the hydrophobic (class I) substitution analogs. As above, those analogs possessing the highest retention times (greatest effective hydrophobicity) also exhibited increased LPS-binding affinity.

Table 4 also includes a summary of the hemolytic activities of the hydrophobic substitution peptides. By way of reference, it is apparent that hemolytic activity of GS14K4 is considerably lower than that of the parent compound, GS14. While not wishing to be constrained to a particular mechanism of action, it appears that the reduced hemolytic activity is due to the lower effective hydrophobicity of GS14K4 caused by structural changes induced by the incorporation of a single enantiomeric substitution within the framework of GS14. The GS14K4 hydrophobicity analogs show a range of hemolytic activities, from that approaching GS14 (e.g., Y2/F2-V3/L3), to greatly decreased hemolytic activity. There is an apparent correlation between retention time (effective hydrophobicity) and hemolytic activity in the present analogs, indicating that the hemolytic activity of the peptides is related to effective hydrophobicity. These studies show that it is possible to further modulate the effective hydrophobicity of the analog peptides by specific residue replacements to either increase or further decrease the effective hydrophobicity. Such changes can be used to modulate hemolytic activity, as well.

The antimicrobial activities of the hydrophobic substitution peptides against a range of gram negative microorganisms is shown in Table 5. Compared to GS14K4, some of the hydrophobicity analogs exhibit either the same or slightly weaker antimicrobial activity, while others exhibit greatly reduced activity. These studies support a further discovery of the present invention, that there is a direct correlation between effective hydrophobicity and antimicrobial activity for all the analogs as shown in FIG. 13.

It is apparent from these data that for all the microorganisms there is a dramatic loss of activity below a certain effective hydrophobicity value (approximately 32 min. retention time, analog V3/A3); for most of the microorganisms, this analog represents the hydrophobicity cutoff value for the peptides studied. Interestingly, for the majority of microorganisms, there is a plateau in the activity level with no further increase in activity with increasing hydrophobicity.

Also shown in Table 5 and FIG. 13 are the therapeutic indicies (a measure of specificity for bacteria over human erythrocytes) of the analogs for the gram negative microorganisms. Due to the greatly decreased hemolytic activity of some of the analogs (see Table 5) some of these possess greater therapeutic indicies than GS14K4 itself. It is clear from FIG. 13 that there is an optimum effective hydrophobicity for all the microorganisms. of the analogs studied, analog V3/A3 possesses the greatest therapeutic indicies and marks an improvement over the biological properties of GS14K4. Although the antimicrobial activity of this peptide is slightly reduced compared to GS14K4, the greatly reduced hemolytic activity is the overiding term in the therapeutic index, resulting in indicies which are in the range of 2- to 5-fold greater than GS14K4. The optimum in therapeutic indicies for all the gram negative microorganisms evaluated is centred at approximately 32 min. The analogs on either side of this optimum (peptides L3/A3 and GS14K4, with retention times of 28.6 min. and 38.9 min., respectively) therefore mark the boundaries of a "therapeutic window", inside which lies the optimum effective hydrophobicity. Therefore, according to an important feature of the present invention, it is recognized that peptides can be designed to fall within this window, and that refinements of activity can be effected by providing for relatively small increments of hydrophobicity changes. This method provides guidance to selection of optimum peptides for the particular microbe and therapeutic.

Activity of the hydrophobicity analogs against a number of gram positive microorganisms and yeast is shown in Table 6. GS14 exhibits extremely limited antimicrobial activity and an extremely low therapeutic index whereas GS14K4 exhibits activity against most of the microorganisms coupled with a high therapeutic index. Unlike the case for gram negative microorganisms where maximum activity plateaued at the level of GS14K4, a number of the hydrophobicity analogs which are more hydrophobic than GS14K4 exhibit greater activity than the parent compound against some of the gram positive microorganisms, as well as in yeast (e.g., Candida albicans).

While GS14K4 generally exhibits the highest therapeutic index, this is due to increased hemolytic activity of the more hydrophobic analogs. One peptide however shows an increase in therapeutic index for C. xeroses. Peptide V3/A3, a slightly less hydrophobic peptide than GS14K4, has a therapeutic index of 520, an increase of approximately 4-fold over GS14K4. As with gram negative microorganisms above, a similar trend of antimicrobial activity with effective hydrophobicity is seen against gram positive microorganisms and yeast (FIGS. 14 and 15).

While there is some variability, overall the hydrophobicity cutoff appears to be shifted to slightly higher hydrophobicity values, indicating a higher hydrophobicity threshold is required for gram positive microorganisms than for gram negative microorganisms. As with the gram negative microorganisms, a therapeutic window can be defined, but centred at somewhat higher hydrophobicity values. For the majority of gram positive microorganisms and yeast, this optimum hydrophobicity is centred at 39 min. (GS14K4) and the analogs on either side (peptides V3/A3 and V3/L3, with retention times of 32.2 min. and 42.5 min., respectively) mark the boundaries of the optimum effective hydrophobicity. Again, it is appreciated that by designing peptides with smaller increments of hydrophobicity within this therapeutic window, optimum peptides for any given microorganism may be identified. The fact that some of the more hydrophobic analogs exhibited significantly greater antimicrobial activity than GS14K4 against gram positve microorganisms and yeast suggests that improvements in activity and specificity may be possible by smaller incremental changes in effective hydrophobicity.

c. Basic Same Class Substitution Analogs

In studies carried out in support of the present invention 10-mer peptides were used as model peptides to investigate the role of and nature of basic residues in the context of a well defined structural framework to define their role in both antimicrobial and hemolytic activities. The peptides are based on the general structure and sequence of the cyclic decapeptide (GS), cyclo(VOL$\underline{F}$P)$_2$, where O is ornithine (Orn). GS is known to exist in an antiparallel β-sheet structure with hydrophobic Val and Leu residues on one face of the molecule and basic Orn residues on the other face. In these studies, peptides were constructed having the general sequence cyclo(VXL$\underline{Y}$P)$_2$, where X denotes the basic residues which were investigated including arginine (Arg), lysine (Lys), ornithine (Orn), 2,4-diaminobutyric acid (Dab), 2,3-diaminoproprionic acid (Dap) and histidine (His). Accordingly, these peptides have been characterized structurally, and their antimicrobial and hemolytic activities were further compared, to determine whether the exact nature of the basic residues results in dissociation of the two activities.

The secondary structures of X-substituted 10-mer peptides were evaluated under aqueous conditions, and it was found that all 6 substitution peptides exhibited essentially similar CD patterns, the major features of which are two large negative ellipticities in the regions of 205 nm and 225 nm. Although the wavelengths of the negative maxima are slightly different from GS, the spectra are very similar to that of GS overall indicating a similar β-sheet structure in all the analogs.

Similarly, the retention times of all the peptides on reversed-phase HPLC are quite similar, ranging from 86.9–89.1 minutes, implying that the peptides also have a similar β-sheet structure.

Toxicity of the peptides to human erythrocytes was measured, and essentially no differences were observed among the various substitution analogs. The activity of GS10 peptides against gram negative microorganisms was tested, and while very similar potencies were observed, incorporation of histidine in GS10 resulted in significantly decreased activity against the majority of gram negative microorganisms tested, indicating that there is a certain basicity required for activity for these microorganisms. The remainder of the basic residue substitutions are similar for a number of microorganisms although for some microorganisms the presence of the shorter positively charged residues (Orn, Dab and Dap) appears to increase antimicrobial activity to some degree compared to Lys- and Arg-containing peptides. All analogs showed identical activities against all gram positive microorganisms except for the His-containing peptide which is weaker for the majority of microorganisms.

Thus, it is a general feature of the invention that in peptides with equivalent structures, the exact nature of the basic residues is not important for hemolytic activity. Generally, the same holds true for antimicrobial activity, although the replacement of basic residues by histidine tends to decrease antimicrobial activity. This decrease in activity tends to be more severe against gram negative microorganisms. This finding indicates that for any class of antimicrobial peptide that any basic residue (with the possible exception of histidine) can be substituted for any other basic residue without significant changes in antimicrobial activity or hemolytic activity. Accordingly, same class (basic) amino acid substitutions are permissible in antimicrobial peptides of the present invention.

3. Non-amphipathic, Non-amphipathic Polarized and Inverse-Sequence (Transposed) Cyclized Peptides According to another feature of the present invention, it is recognized that alterations of the general amphipathic character of the cyclic peptide molecule can result in altered biological activities of the peptides.

Thus, in studies carried out in support of the invention, peptides possessing the same residue composition and β-sheet structure as GS14 but with reduced effective hydrophobicities were tested along the lines described in the previous sections.

Sequences of peptides GS14na (where "na" is non-amphipathic) and GS14napol (where "napol" is polarized non-amphipathic) are shown in Table 7. Also tested were GS14 analog peptides in which hydrophobic and basic residues were reversed. Peptide GS14inv (where "inv" is inverse) switches the hydrophobic residues of GS14 with basic residues and the basic residues with hydrophobic residues (Table 7). Additionally, two diastereomers of GS14inv were synthesized to disrupt any β-sheet structure of GS14inv.

The secondary structure of GS14 analogs was evaluated by CD spectroscopy. Shown in FIG. 16 is a comparison of the CD spectra of GS14, GS14na, GS14napol and GSinv. As shown, GS14na and GS14napol exhibit similar CD spectra as GS14 and therefore also exist in a β-sheet conformation.

The CD spectrum of GS14inv on the other hand is typical of a disordered structure. The incorporation of both enantiomeric substitutions in GS14inv had no effect on the CD spectra indicating that no further disruption of β-sheet structure occurred.

The HPLC retention times of the peptides are also listed in Table 7. While GS14 has a high retention time due to its large hydrophobic face, both GS14na and GS14napol have much lower retention times. As discussed above, the retention time of GS14 analogs can be decreased by structural perturbations leading to a reduced effective hydrophobicity. In this case however, both GS14na and GS14napol have the same β-sheet structure as GS14, and the differences in retention times is likely due to a reduced hydrophobic face, and therefore reduced amphipathicity. The GS14inv analogs show reduced retention times, as is expected, since they possess fewer hydrophobic residues than GS14. Interestingly, of the three GS14inv analogs, GS14inv has the greatest retention time. This indicates that a hydrophobic face can be induced on GS14inv by the reversed-phase matrix since the incorporation of enantiomers in the framework of GS14inv reduces the retention times.

Shown in Table 7 is the measured hemolytic activity of the peptides. GS14 possesses very high hemolytic activity, whereas both nonamphipathic peptides, GS14na and GS14napol, have greatly reduced hemolytic activity. Since both these peptides maintain their β-sheet conformation (CD spectral data, above), it is proposed as a further aspect of the present invention that the reduced hemolytic activity is due to reduced amphipathicity, and hence reduced effective hydrophobicity compared to GS14.

The GS14inv peptides also exhibit greatly decreased hemolytic activity and this is likely due to their low intrinsic hydrophobicity.

The activity of the peptides against gram negative microorganisms is shown in Table 8. While GS14 exhibits no activity against any of the microorganisms tested, all the analogs exhibit activity ranging from strong to moderate for most microorganisms, and weak for Salmonella strain (C587). The decreased hemolytic activty of the GS14 non-amphipathic analogs is greatly reduced compared to GS14 resulting in large increases in therapeutic index compared to GS14. The greatest increase in therapeutic index was seen with GS14inv against *E. coli* DC2, an increase of greater than 200,000 compared to GS14.

The binding affinity of the peptides to bacterial membranes (lipopolysaccharide, LPS) is shown in Table 7. All peptides exhibit weaker binding compared to GS14, suggesting that the reason GS14 is not particularly active against gram negative microorganisms is due to its high affinity for the outer membrane. Without committing to any particular mechanistic theory underlying the present invention, this tight binding to the outer membrane may preclude GS14 from diffusing to its site of action on the inner membrane.

Table 9 shows the antifungal and gram positive activity of the peptides described above. These peptides showed no antimicrobial activity against *S. aureus* strains and *B. subtilis* at the concentrations tested. Some of the peptides exhibited moderate activity against the remainder of the microorganisms listed. However, due to their greatly reduced hemolytic activity, relative to GS14, the analogs still show large increases in therapeutic indicies. One exception is the gram negative microorganism *C. xeroses;* all peptides discussed in this section exhibit very strong activity against this microorganism. Peptide GS14inv shows the greatest increase in therapeutic index with this microorganism, a 10,000-fold compared to GS14.

Based on the foregoing data, it is apparent that a high therapeutic index can be obtained in cyclic antimicrobial peptides by reducing the effective hydrophobicity of the peptide. According to this aspect of the invention, a β-sheet structure was maintained, and reduced effective hydrophobicity was achieved by altering the placement of hydrophobic and basic residues in the β-sheet structural framework of GS14. Similar increases in therapeutic indicies can also be realized by the combination of changing the ratio of basic to hydrophobic residues. In this case however, the reduced effective hydrophobicity is due to a combination of reduced number of hydrophobic residues as well as the disruption of β-sheet structure caused by the presence of six basic residues.

2. 12-mer and Related Chain-length Modified Antimicrobial Peptides

Antimicrobial peptides in accordance with the present invention may also be cyclic peptides that do not conform to the β-pleated sheet structure, such as peptides whose lengths are not 2(2n+1) where n is an integer. Thus, according to this feature of the invention, peptides having lengths of 11, 12, 13, 15, 16, 17, 19 or 20 amino acids, for example, would not be expected to adopt a β-pleated sheet conformation under aqueous conditions. Generally, such peptides will include cyclic peptides having the sequence $(X1X2)_n$-X3-P-$(X2X1)_n$-X3-P, where n is an integer greater than or equal to 2. According to this formula, each X1 is independently selected from the group consisting of alanine, valine, leucine, norvaline, isoleucine, norleucine, methionine, phenylalanine, tyrosine and tryptophan; each X2 is independently selected from the group consisting of lysine, arginine, histidine, ornithine, 2,4-diaminobutyric acid, and 2,3-diamino propionic acid; and each X3 is a D-amino acid independently selected from the group consisting of alanine, valine, leucine, norvaline, isoleucine, norleucine, methionine, phenylalanine, tyrosine and tryptophan Such peptides may be odd numbers of of amino acids in length, by deleting one or more of X1 or X2 residues. Such peptides are further characterized lacking a β-pleated sheet structure, as evidenced by circular dichroism spectrum lacking peaks characteristic of β-pleated sheet structure. Exemplified herein are 12-mer peptides, of which GS12 is the prototype (Table 10).

Table 10 shows the activity profiles of several 12-mer peptides formed and substituted in accordance with the present invention. GS12 peptide analogs were made by systematically incorporating native residues into the parent structure, in order to determine the importance of each in antibiotic and hemolytic activity (e.g., GS12LV, GS12F, GS12FO, GS12FO/LL).

In experiments carried out in support of the present invention, it was found that cyclic peptides containing 12 residues exhibit completely different spectra than GS or GS14, the most noticeable difference being a substantially reduced ellipticity in the range 210 to 225 nm, indicating a largely disordered structure. All 12 residue peptides exhibited similar disordered CD spectra. In further studies, this periodicity of β-structure as a function of ring size was confirmed by $^1$H-NMR spectroscopy using the chemical shift index (Wishart, et al., 1992) and detailed analysis of coupling constants.

As mentioned above, GS12 cannot form the beta-sheet conformation, due to the number of residues in the cyclic structure; its CD curve is typical of that of a disordered structure. When the 12-mer structure was subjected to molecular modelling analysis, including incorporation of two type II' β turns (Example 4), the amino and carboxyl termini are located far apart, in contrast to modelling of, for example, GS14, which predicts a cyclic structure. Although it is possible to chemically link the termini of the 12-mer during cyclization of the peptides, this will lead to severe distortion of the β-sheet structure. Furthermore, no combination of β-turn types could bring the termini together in the 12 residue peptide. These models show that the basis of the periodicity in β-structure seen by CD spectroscopy lies in the number of residues contained within the strands of these cyclic peptides. There is an absolute requirement for an odd number of residues between residues i+2 and i+1 of the two turns to maintain β-strand character in cyclic peptides.

Antimicrobial activity of GS12 and representative analogs thereof is presented in Table 10. GS12 was slightly less active against gram negative microorganisms and yeast than GS, and it exhibited substantially reduced activity against gram positive microorganisms. However, the GS12 analogs exhibited superior therapeutic index values relative to GS10 or GS14. Results for individual isolates are summarized in Tables 11 and 12, below.

TABLE 11

ANTIBIOTIC ACTIVITY[A] OF CYCLIC GS RING ANALOGS

| Peptide[b] | Gram-Negative | | | | | |
|---|---|---|---|---|---|---|
| | E. coli UB1005 | E. coli DC2 | E. coli SC9251 | E. coli SC9252 | P. aerugi- nosa H187 | P. aerugi- nosa H188 |
| GS | 19 | 9 | 13 | 5 | 25 | 16 |
| GS10 | 25 | 14 | 21 | 8 | 19 | 13 |
| GS12 | 25 | 11 | 42 | 30 | 75 | 10 |
| GS14 | 400 | 190 | 400 | 190 | 400 | 400 |
| GS12F | 17 | 9 | 11 | 14 | 38 | 8 |
| GS12LV | 21 | 14 | 22 | 25 | 58 | 10 |
| GS12FO | 22 | 5 | 6 | 9 | 50 | 5 |
| GS12FO/ LL | 16 | 5 | 8 | 9 | 63 | 8 |

TABLE 12

| Peptide[b] | Gram-Positive | | | | | |
|---|---|---|---|---|---|---|
| | S. aureus SAP0017 | S. aureus K147 | S. epi- dermidis | E. faecalis | B. subtilis | Fungus C. albicans |
| GS | 5 | 5 | 3 | 6 | 6 | 9 |
| GS10 | 9 | 6 | 6 | 14 | 6 | 13 |
| GS12 | 230 | 300 | 50 | 300 | 300 | 42 |
| GS14 | 400 | 400 | 110 | 29 | 400 | 230 |
| GS12F | 130 | 150 | 38 | 100 | 150 | 13 |
| GS12LV | 300 | 330 | 25 | 150 | 400 | 50 |
| GS12FO | 88 | 130 | 34 | 260 | 75 | 16 |
| GS12FO/ LL | 44 | 66 | 22 | 41 | 38 | 16 |

[a]Minimum inhibitory concentration (ng/ml).
[b]GS4, GS6, GS8 showed no antibiotic activity.

Additional substitutions were made in the 12 residue peptides in an attempt to increase antibiotic activity because of the promising activities displayed by GS12, i.e., reasonable antibiotic activity coupled with low hemolytic activity (see below). The placement of hydrophobic residues Val and Leu (GS12LV) had no effect on antibiotic activity. Replacement of D-Tyr by D-Phe (GS12F) resulted in an increase in activity against gram negative microorganisms and yeast comparable to that of GS itself, as well as an increase in activity against gram positive microorganisms, although the latter activity was still low. The increased activity of GS12F compared to GS12 is likely related to increased hydrophobicity. Further substitutions in the D-Phe containing peptide, namely Orn for Lys (GS12FO) and Leu for Val (GS12FO/LL) had no further effect on activity against gram negative microorganisms and yeast with these activities reaching a plateau at the level of GS itself. An increase in gram positive activity was seen in GS12FO/LL, however, indicating that hydrophobicity may be related to activity against gram positive microorganisms in the 12 residue peptides. This observation may also be extended to other cyclic peptides having longer or shorter chain lengths, as described herein. This conclusion is supported by the finding that activity of the 12 residue peptide series against gram positive microorganisms is correlated with overall hydrophobicity as measured by retention time on HPLC.

From the foregoing results it can be concluded that for 12 residue GS analogs: i) the presence of D-Phe enhances both gram positive and gram negative activity; ii) replacement of Orn by Lys has no effect on either activity; iii) increased hydrophobicity results in greater antimicrobial activity against gram positive bacteria; and iv) gram positive activity is much more sensitive to hydrophobicity than either antifungal or gram negative activity. These discoveries form part of the present invention.

In an attempt to further optimize the therapeutic index of GS12, i.e. to further increase antibiotic activity while decreasing hemolytic activity, a number of substitutions were made in GS12. It can be seen that the placement of Val and Leu residues in the D-Tyr containing peptide (GS12LV) increased hemolytic activity, resulting in a decrease in the therapeutic index compared to GS12. Replacement of D-Tyr by D-Phe in GS12F resulted in decreased hemolytic activity coupled with increased antibiotic activity giving a very high therapeutic index for this analog, an improvement of approximately 10-fold for gram negative microorganisms and a 7-fold improvement for yeast compared to GS (Table 10). Substitution of Orn for Lys in GS12F caused an increase in hemolytic activity in GS12FO and GS12FO/LL, resulting in a poorer therapeutic index for these analogs compared to GS12F. However, the therapeutic indices of these analogs were still better than that of GS, with a 4-fold and 2-fold improvement in therapeutic index against gram negative bacteria and yeast, respectively. These results indicate that apart from the number of residues in the ring, it is the nature of the basic residues and D-amino acids, and the combination of D-amino acid and the placement of hydrophobic residues which are responsible for modulating hemolytic activity. These findings show that it is possible to substantially increase the specificity of GS analogs for microorganisms over normal eukaryotic cells, primarily by choice of the appropriate ring size, and secondly by incorporation of appropriate substitutions in the chosen ring size.

In order to determine whether ring size affects the interaction between the peptide and bacterial membranes, we studied the interaction between the GS ring analogs and bacterial lipopolysaccharide (LPS). It has been shown previously that dansyl-polymixin (DPX) is a good probe for cationic binding sites on both purified LPS as well as whole bacterial cells (Example 8; Moore, et al., 1986; Sawyer, et al., 1988; Hancock, 1981). This probe fluoresces strongly when bound to LPS and only weakly in solution, and hence, any compound which displaces dansyl-polymixin from LPS results in a decrease in observed fluorescence. The LPS binding activity of various GS analogs was investigated, as discussed above. Peptides containing eight or more residues showed a progressively increased ability to displace dansyl-polymixin. Results for the 12-mer analogs are presented in Table 10.

In comparison to shorter peptides, it was found that addition of two positive charges to form GS12 increased LPS binding activity by approximately 6-fold. The differences in LPS binding by the analogs appears to be due to the number of basic residues as well as the presence or absence of β-sheet structure. The β-sheet structure may be important in this context, as this will either place the basic residues on the same face of the molecule with a specific distance between the positive charges in the case of a peptide in a β-sheet conformation, or in some undefined position in the case where the peptide assumes a disordered conformation. Therefore, for two peptides with the same number of basic residues, the one in the β-sheet conformation binds stronger than a peptide in a disordered conformation.

Permeabilization of *E. coli* outer membranes by GS analogs was monitored using the hydrophobic fluorescent probe N-phenyl-1-naphthylamine (NPN; Example 7). NPN fluorescence is substantially increased when it is incorporated into the hydrophobic bacterial cell membrane (after permeabilization) compared to its fluorescence in the presence of bacterial cells under non permeabilizing conditions (Loh, et al., 1984). In experiments carried out in support of the present invention, 4- and 6-mer peptides caused no outer membrane destabilization at the concentrations tested. GS10, GS12 and GS14 all showed a similar capacity to disrupt the *E. coli* membrane as GS itself, whereas GS8 showed a diminished capacity to disrupt membranes.

From the foregoing, it is apparent that there is a periodicity in β-sheet content as a function of ring size. Here, 6, 10 and 14 residue peptides exhibit β-sheet structure as found in GS, while 8 and 12 residue peptides display a disordered structure. These results have also been confirmed using NMR spectroscopy. These findings indicate a preference for an odd number of residues between the two turns of the cyclic peptide (made up by the D-Xxx-Pro sequence). Furthermore, only those peptides with an odd number of residues between the two corner residues can form an alternating hydrogen bonding pattern as found in antiparallel β-sheets (i.e. a hydrogen bonded pair of residues followed by a non-hydrogen bonded pair etc.). Molecular modelling studies have also confirmed that it is not possible for the 8 and 12 residue peptides to form β-sheet structures. In further studies in support of the present invention, it has also been observed that the 12 residue peptides take on a somewhat circular structure similar to that of valinomycin in aqueous medium.

These results indicate that the 12 residue cyclic peptides are disordered in solution. Therefore, it is likely that the effective hydrophobicity of these peptides will be lower in such a structure compared to a β-sheet structure containing alternating hydrophobic and hydrophilic residues. Modelling studies showed that the 12 residue peptide cannot achieve a perfect β-sheet structure with all potential hydrogen bonds formed (where residues i and i+3 of a turn are H-bonded) due to the number of residues per strand.

In other studies in support of the present invention, it was discovered that cyclic GS analogs containing 8 or fewer residues were completely inactive against both bacteria as well as eukaryotic cells. Without committing to any particular mechanistic theory, it is likely that this indicates a minimum requirement for the proportion of hydrophobic to hydrophilic residues as well as a minimum requirement for overall effective hydrophobicity of the cyclic analogs. Both binding to LPS and destabilization of *E. coli* membranes were greatly reduced in analogs containing 8 or fewer residues.

Activity against gram positive microorganisms was much more sensitive to changes in ring size than other activities measured. There was a fifty-fold difference in activity between GS and the least active 12 residue analog against gram positive bacteria. In contrast, only a two-fold difference for gram negative bacteria, when these two were compared. These results indicate that gram positive antibacterial activity and hemolytic activity are much more sensitive to ring size, and hence structure, than gram negative antibacterial activity.

The lack of hemolytic activity displayed by the 12 residue peptides may be a result of either a lack of binding to erythrocytes or the inability to carry out GS-like membrane disruption once bound to erythrocytes. Both these possibilities are likely due to decreased effective hydrophobicity owing to the lack of β-structure in these peptides.

III. Method of Selecting Peptides

From the data discussed in the sections above, it is apparent that head-to-tail cyclic peptides, such as 12-and 14-residue peptides exemplified herein, exhibit superior antimicrobial activity in comparison, for example to GS. In accordance with the present invention, it is possible to design peptides that have the properties desired. Thus, for example, using the 14-mer GS14 analog peptides as an example, addition of a single D-amino acid substitutions within the non-turn residues will produce useful antibiotic peptides, by virtue of their high antibiotic properties and their low hemolytic activities. Additional modifications may be made by transposition of residues, inversion of residue sequences, substitution of same class (hydrophobic or basic) residues, and the like, according to the teachings provided herein. Accordingly, the invention encompasses peptide antimicrobial agents that include and/or combine any one or more of the foregoing peptide manipulations.

With the guidance of the present invention, the practitioner, upon selecting a peptide design and making the peptide, can then test the peptide in the various physicochemical and biological assays described herein, according to the preferred biological endpoint. For example, where decreased hemolytic activity is desirable, a peptide having a CD profile indicating lack of or disrupted β-pleated sheet structure may be sought. Peptides can be screened in this assay, and/or may also be placed in selected biological screens, such as the hemolytic assays and various antimicrobial assays discussed herein and known in the art.

That is, without relying on a particular operant mechanism of action, it is a discovery of the present invention that lack of β-sheet structure and/or amphipathicity in such analogs contributes significantly to their heightened activity profiles. Therefore, in one aspect, preferred antimicrobial peptides in accordance with the present invention will include the characteristics of lack of, or at least significantly reduced percentage of β-sheet structure and/or amphipathicity, relative to the parent structure; here, GS14, or relative to GS.

A further advantage of peptides of the present invention is the possibility that there may be lowered development of resistance against them, since, again without relying on any particular theory of mechanism, the apparent target site of antimicrobial compositions of the invention is the microbial membrane.

IV. Utility

The present peptide compositions can be used as antimicrobial agents, particularly in human and veterinary therapeutics. The compositions may also be used as antimicrobial food additives, to prevent or reduce the risk of infection from food products. As discussed above, the various peptides exhibit differential microbial specificity which will dictate their use. Antimicrobial activity, as defined herein, includes but is not limited to activity against gram positive and negative bacteria, mycoplasma, microscopic fungi, and the like. It is most desirable that the antimicrobial peptides possess relatively high antimicrobial activity, either broad or selected spectrum, and relatively low hemolytic activity, since it is the hemolytic activity of GS that limits its usefulness.

For use in therapeutics, peptides may be given by any of a number of conventional routes, in accordance with the particular site of infection to be treated. For example, the peptides may be given topically to the skin or epithelial linings of body cavities, for infections in such regions. Examples of treatable body cavities include the vagina, the rectum and the urethra. Conveniently, the peptides would be formulated into suppository form for administration to these areas.

The peptides can be given via intravenous or intraperitoneal injection. Intravenous injection will be particularly appropriate for blood-borne infections; intraperitoneal administration may be more appropriate for infections localized to the abdominal region. Similarly, the peptides may be injected to localized regions of the body, to combat localized, needle accessible infections.

The antimicrobial peptides may also be administered via nasal insufflation. This route is particularly appropriate for treating infections of the lungs or respiratory passages, such as infections of *Pseudomonas aeruginosa*.

Enteral administration is also possible, in view of the apparent resistance of the peptides to common proteases. For such administration, the peptides should be formulated into an appropriate capsule or elixir for oral administration, or into a suppository for rectal administration.

The foregoing exemplary administration modes will likely require that the peptides be formulated into an appropriate carrier, including ointments, gels, suppositories. Appropriate formulations for peptides are well known to persons skilled in the art.

Dosage of the peptides will vary, depending upon the antimicrobial potency and Therapeutic index of the particular peptide selected. These parameters are easily determinable by the skilled practitioner, particularly in view of the exemplary test methods described herein. Persons skilled in the art will appreciate that other test assays may be substituted, in accordance with the particular therapeutic target and route of administration required.

As an example, an exemplary peptide that has activity against *Staphylococcus epidermidis* at an MIC of 1 μg/ml and exhibits hemolytic activity at 75 μg/ml, resulting in a therapeutic index of 75. The practitioner will know that the final desired therapeutic concentration will be somewhat greater than 1, but substantially less than 75 μg/ml. An appropriate target concentration might therefore be 10 μg/ml. The practitioner will then choose a mode of administration and dosage that will provide this target concentration at the site of infection. In addition to the route of administration, the dosage will depend on the size of the individual to be treated and the volume of distribution of the compound, as well as its half-life, all of which can be determined empirically by persons skilled in the art of pharmaceutics.

The compositions described herein can be used in various methods of treatment—as in human and veterinary therapeutics or food preservation, as discussed above. The present invention includes the discovery that, contrary to what was previously thought, GS and analogs thereof have significant antibiotic activity against gram-negative bacteria and fungi. For example, GS is effective against gram-negative organisms, particularly *E. coli* and *P. aeruginosa*, at MIC's ranging from 3–12.5 μg/ml. GS also exhibits antifungal activity, exemplified by inhibition of growth and/or killing of *Candida albicans* at an MIC of 6.2 μg/ml (measured in liquid culture, as described herein).

Particularly useful in the context of the present invention are the GS12 and GS14 analogs, as discussed above.

The invention also includes a method of inhibiting and/or killing gram-positive bacteria using the peptide analogs described herein. The methods, when employed in a therapeutic setting, rely on the same pharmacological and pharmaceutical principles discussed above.

According to another feature of the invention, GS14, which is apparently an unlikely antibacterial agent, is useful against mycoplasma infection. In particular, it has been found, in studies carried out in support of the present invention to show substantial activity against the mycoplasma *Acholeplasma laidlawii*, as evidenced by a MIC of less than about 30 μg/ml. One use of such a compound is inclusion in tissue culture media, where mycoplasma contamination can pose serious problems in industrial applications of cell culture. Here, the GS14 peptide, or its analogs, is added at a concentration that is effective to inhibit or prevent growth of mycoplasma. Such concentrations can be determined according to standard methods known in the art.

TABLE 1

Sequences and biological and physical properties of GS14 diastereomers

| Peptide Name | Linear Sequence[a] | Retention Time (min)[b] | LPS binding affinity ($\mu$M)[c] | Hemolytic activity ($\mu$g/ml)[d] |
|---|---|---|---|---|
| GS | VOL<u>F</u>PVOL<u>F</u>P | 54.9 | 295 | 12.5 |
| GS14 | VKLKV<u>Y</u>PLKVKL<u>Y</u>P | 50.6 | 3 | 1.5 |
| GS14V1 | <u>V</u>KLKV<u>Y</u>PLKVKL<u>Y</u>P | 41.3 | 41 | 50 |
| GS14K2 | V<u>K</u>LKV<u>Y</u>PLKVKL<u>Y</u>P | 39.8 | 50 | 75 |
| GS14L3 | VK<u>L</u>KV<u>Y</u>PLKVKL<u>Y</u>P | 44.2 | 35 | 12.5 |
| GS14K4 | VKL<u>K</u>V<u>Y</u>PLKVKL<u>Y</u>P | 37.8 | 93 | 200 |
| GS14V5 | VKLK<u>V</u>YPLKVKL<u>Y</u>P | 41.1 | 33 | 150 |
| GS14Y6 | VKLKV<u>Y</u>PLKVKL<u>Y</u>P | 40.2 | 20 | 25 |
| GS14P7 | VKLKV<u>Y</u>PLKVKL<u>Y</u>P | 42.6 | 18 | 12.5 |
| GS14L8 | VKLKV<u>Y</u>P<u>L</u>KVKL<u>Y</u>P | 40.3 | 62 | 50 |
| GS14K9 | VKLKV<u>Y</u>PL<u>K</u>VKL<u>Y</u>P | 38.8 | 60 | 100 |
| GS14V10 | VKLKV<u>Y</u>PLK<u>V</u>KL<u>Y</u>P | 45.4 | 18 | 6.2 |
| GS14K11 | VKLKV<u>Y</u>PLKV<u>K</u>L<u>Y</u>P | 37.1 | 50 | 150 |
| GS14L12 | VKLKV<u>Y</u>PLKVK<u>L</u><u>Y</u>P | 41.3 | 32 | 35 |
| GS14Y13 | VKLKV<u>Y</u>PLKVKL<u>Y</u>P | 40.6 | 24 | 12.5 |
| GS14P1A | VKLKV<u>Y</u>PLKVKL<u>Y</u>P | 42.9 | 20 | 9 |
| GS14K2K4 | V<u>K</u>LKV<u>Y</u>PLKVKL<u>Y</u>P | 33.1 | 120 | 400 |
| GS14K2K4K9K11 | V<u>K</u>LKV<u>Y</u>PLKVKL<u>Y</u>P | 28.5 | 200 | >800 |

[a]Linear sequences of cyclic peptides. Underlined residues represent D-amino acids. O is ornithine.
[b]Retention time on RP-HPLC as determined from FIG. 3.
[c]Peptide concentration to displace 50% of dansyl-polymyxin B from LPS as described under Materials and Methods.
[d]Peptide concentration for 100% lysis of human erythrocytes.

TABLE 2

Activity of GS14 diastereomers against gram negative microorganisms

Minimum Inhibitory Concentration ($\mu$g/mL) and Therapeutic Index[1]

| Peptide | P. aeruginosa H187 activity | index | P. aeruginosa H188 activity | index | E. coli UB1005 activity | index | E. coli DC2 activity | index | S. typhinurium C587 activity | index | S. typhinurium C610 activity | index |
|---|---|---|---|---|---|---|---|---|---|---|---|---|
| GS | 25 | 0.5 | 6.2 | 2 | 9 | 1.4 | 3.1 | 4 | 18 | 0.7 | 9 | 1.4 |
| GS14 | >200 | <0.01 | >200 | <0.01 | >200 | <0.01 | >200 | <0.01 | >200 | <0.01 | >200 | <0.01 |
| GS14V1 | 60 | 0.8 | 3.1 | 16 | 6.2 | 8.1 | 3.1 | 16 | 50 | 1 | 6.2 | 8.1 |
| GS14K2 | 75 | 1 | 62 | 12 | 12.5 | 6 | 3.1 | 24 | 25 | 3 | 3 | 25 |
| GS14L3 | >200 | <0.1 | 200 | 0.1 | 200 | 0.1 | 50 | 0.25 | >200 | <0.1 | >200 | <0.1 |
| GS14K4 | 25 | 8 | 3.1 | 65 | 6.2 | 32 | 3.1 | 65 | 12.5 | 16 | 4 | 50 |
| GS14V5 | 100 | 1.5 | 62 | 24 | 15 | 10 | 3.1 | 48 | 100 | 1.5 | 12.5 | 12 |
| GS14Y6 | 200 | 0.1 | 50 | 0.5 | 50 | 0.5 | 3.1 | 8.1 | >200 | <0.1 | 100 | 025 |
| GS14P7 | 200 | 0.06 | 100 | 0.1 | 200 | 0.06 | 6.2 | 2 | >200 | 0.06 | 200 | 0.06 |
| GS14L8 | 37 | 1.4 | 3.1 | 16 | 6.2 | 8.1 | 3.1 | 16 | 12.5 | 4 | 6.2 | 8.1 |
| GS14K9 | 50 | 2 | 62 | 16 | 12.5 | 8 | 3.1 | 32 | 17 | 5.9 | 6.2 | 16.1 |
| GS14V10 | >200 | <0.03 | 200 | 0.03 | 200 | 0.03 | 3.1 | 2 | >200 | <0.03 | 200 | 0.03 |
| GS14K11 | 37 | 4.1 | 5 | 30 | 6.2 | 24 | 3.1 | 48 | 12.5 | 12 | 6.2 | 24 |
| GS14L12 | 200 | 0.2 | 12.5 | 2.8 | 17 | 2.1 | 3.1 | 11 | 150 | 0.2 | 50 | 0.7 |
| GS14Y13 | >200 | <0.06 | 100 | 0.1 | 100 | 0.1 | 3.1 | 4 | >200 | <0.06 | >200 | <0.06 |
| GS14P14 | >200 | <0.05 | 100 | 0.1 | 100 | 0.1 | 4 | 2.3 | >200 | <0.05 | >200 | <0.05 |
| GS14K2K4 | 150 | 2.7 | 12.5 | 32 | 50 | 8 | 6.2 | 65 | 200 | 2 | 25 | 16 |
| GS14K2K4K9K11 | >200 | — | 12.5 | >64 | 100 | >8 | 50 | >16 | >200 | — | 25 | >32 |

[1]Therapeutic index = hemolytic activity/antibacterial activity

TABLE 3

Antifungal and gram positive activity of GS14 diastereomers

Minimum Inhibitory Concentration ($\mu$g/mL) and Therapeutic Index[1]

| Peptide | S. aureus SAP0017 activity | index | S. aureus K147 activity | index | S. epidermidis activity | index | B. subtilis activity | index | E. faecalis activity | index | C. xeroses activity | index | C. Albicans activity | index |
|---|---|---|---|---|---|---|---|---|---|---|---|---|---|---|
| GS | 1.5 | 8.3 | 1.5 | 8.3 | 1.5 | 8.3 | 3.1 | 4 | 3.1 | 4 | 0.8 | 16 | 4 | 3.1 |
| GS14 | >200 | <0.01 | >200 | <0.01 | 200 | 0.01 | >200 | <0.01 | 1.5 | 1 | 9 | 0.2 | 150 | 0.01 |
| GS14V1 | 50 | 1 | 100 | 0.5 | 3.1 | 16 | 50 | 1 | 1.5 | 33 | 1.5 | 33 | 5 | 10 |
| GS14K2 | 50 | 1.5 | 100 | 0.8 | 6.2 | 12 | 50 | 1.5 | 1.5 | 50 | 0.8 | 94 | 6.2 | 12 |

TABLE 3-continued

Antifungal and gram positive activity of GS14 diastereomers

Minimum Inhibitory Concentration (μg/mL) and Therapeutic Index[1]

| Peptide | S. aureus SAP0017 activity | index | S. aureus K147 activity | index | S. epidermidis activity | index | B. subtilis activity | index | E. faecalis activity | index | C. xeroses activity | index | C. Albicans activity | index |
|---|---|---|---|---|---|---|---|---|---|---|---|---|---|---|
| GS14L3 | 200 | 0.06 | >200 | <0.06 | 50 | 0.25 | >200 | <0.06 | 0.8 | 16 | 0.8 | 16 | 100 | 0.1 |
| GS14K4 | 50 | 4 | 100 | 2 | 2 | 100 | 25 | 8 | 1.5 | 133 | 1.5 | 133 | 6.2 | 32 |
| GS14V5 | 50 | 3 | 100 | 1.5 | 3.1 | 48 | 200 | 0.8 | 1.5 | 100 | 1.5 | 100 | 6.2 | 24 |
| GS14Y6 | >200 | <0.1 | >200 | <0.1 | 6.2 | 4 | >200 | <0.1 | 3.1 | 8.1 | 1 | 25 | 12.5 | 2 |
| GS14P7 | >200 | <0.06 | >200 | <0.06 | 6.2 | 2 | >200 | <0.06 | 6.2 | 2 | 1 | 12.5 | 25 | 0.5 |
| GS14L8 | 25 | 2 | 50 | 1 | 3.1 | 16 | 12.5 | 4 | 1.5 | 33 | 0.8 | 63 | 6.2 | 8 |
| GS14K9 | 25 | 4 | 50 | 2 | 6.2 | 16 | 25 | 4 | 1.5 | 67 | 1.5 | 67 | 6.2 | 16 |
| GS14V10 | 50 | 0.1 | 200 | 0.03 | 3.1 | 2 | 200 | 0.03 | 1.5 | 4 | 0.8 | 8 | 17 | 0.4 |
| GS14K11 | 25 | 6 | 25 | 6 | 3.1 | 48 | 25 | 6 | 1.5 | 100 | 0.8 | 188 | 6.2 | 24 |
| GS14L12 | 50 | 0.7 | 100 | 0.4 | 3.1 | 11 | 200 | 0.2 | 0.8 | 44 | 3.1 | 11 | 9 | 3.9 |
| GS14Y13 | >200 | <0.06 | >200 | <0.06 | 9 | 1.4 | >200 | <0.06 | 3.1 | 4 | 1 | 12.5 | 25 | 0.5 |
| GS14P14 | >200 | <0.1 | >200 | <0.1 | 6.2 | 1.5 | >200 | <0.01 | 6.2 | 1.5 | 1 | 9 | 25 | 0.4 |
| GS14K2K4 | >200 | <2 | >200 | <2 | 100 | 4 | >200 | <2 | >200 | <2 | 9 | 44 | 200 | 2 |
| GS14K2K4K9K11 | >200 | — | >200 | — | >200 | — | >200 | — | >200 | — | 25 | >32 | >200 | — |

[1]Therapeutic index = hemolytic activity/antibacterial activity

TABLE 4

Sequences and biological and physical properties pf GS14K4 diastereomers

| Peptide | Linear Sequence[a] | Retention Time (min)[b] | Mean Residue Hydrophobicity[c] | LPS binding affinity (μM)[d] | Hemolytic activity (μg/ml)[e] |
|---|---|---|---|---|---|
| GS14 | VKLKVYPLKVKLYP | 49.5 | −1.11 | 3 | 1.5 |
| GS14K4 | VKLKVYPLKVKLYP | 38.9 | −1.11 | 93 | 200 |
| L3/A3 | VKAKVYPAKVKAYP | 28.6 | 1.31 | 243 | >800 |
| V3/A3 | AKLKAYPLKAKLYP | 32.2 | 0.14 | 163 | >800 |
| V3L3/A6 | AKAKAYPAKAKAYP | 21.7 | 2.557 | 291 | >800 |
| V3/L3 | LKLKLYPLKLKLYP | 42.5 | −2.29 | 46 | 25 |
| Y2/F2 | VKLKVFPLKVKLFP | 42.3 | −2.15 | 59 | 40 |
| Y2/F2 V3/L3 | LKLKLFPLKLKLFP | 46.2 | −3.33 | 25 | 12.5 |

[a]Linear sequences of cyclic peptides. Underlined residues represent D-amino acids.
[b]Retention time on RP-HPLC at 25° C.
[c]Calculated using the HPLC hydrophobicity scale of Parker et al.
[d]Peptide concentration to displace 50% of dansyl-polymyxin B from LPS.
[e]Peptide concentration for 100% lysis of human erythrocytes.

TABLE 5

Activity of GS14K4 hydrophobicity analogs against gram negative microorganisms

Minimum Inhibitory Concentration (μg/mL) and Therapeutic Index[1]

| Peptide | P. aeruginosa H187 activity | index | P. aeruginosa H188 activity | index | E. coli UB1005 activity | index | E. coli DC2 activity | index | S. typhinurium C587 activity | index | S. typhinurium C610 activity | index |
|---|---|---|---|---|---|---|---|---|---|---|---|---|
| GS14 | >200 | <0.01 | >200 | <0.01 | >200 | <0.01 | >200 | <0.01 | >200 | <0.01 | >200 | <0.01 |
| GS14K4 | 25 | 8 | 3.1 | 65 | 6.2 | 32 | 3.1 | 65 | 12.5 | 16 | 4 | 50 |
| L3/A3 | 200 | 8 | 75 | 21 | 200 | 8 | 200 | 8 | >200 | 4 | 100 | 16 |
| V3/A3 | 75 | 21 | 18 | 89 | 12.5 | 130 | 9 | 180 | 35 | 46 | 62 | 260 |
| V3L3/A6 | >200 | 4 | 75 | 21 | >200 | 4 | >200 | 4 | >200 | 4 | >200 | 4 |
| V3/L3 | 100 | 0.25 | 3.1 | 8 | 6.2 | 4 | 3.1 | 8 | 100 | 0.25 | 15 | 1.7 |
| Y2/F2 | 17 | 2.4 | 3.1 | 13 | 6.2 | 6.5 | 1.5 | 27 | 9 | 4.4 | 3.1 | 13 |
| Y2/F2 V3/L3 | 12.5 | 1 | 3.1 | 4 | 9 | 1.4 | 2 | 6.3 | 35 | 0.4 | 12.5 | 1 |

[1]Therapeutic index = hemolytic activity/antibacterial activity. For the calculation of the therapeutic index, values of 400 μg/ml were used for MIC values of >200 μg/ml and values of 1600 μg/ml were used for hemolytic activity values of >800 μg/ml.

TABLE 6

Antifungal and gram positive activity of GS14K4 hydrophobicity analogs

Minimum Inhibitory Concentration (μg/mL) and Therapeutic Index[1]

| Peptide | S. aureus SAP0017 activity | index | S. aureus K147 activity | index | S. epidermidis activity | index | B. subtilis activity | index | E. faecalis activity | index | C. xeroses activity | index | C. Albicans activity | index |
|---|---|---|---|---|---|---|---|---|---|---|---|---|---|---|
| GS14 | >200 | <0.01 | >200 | <0.01 | 200 | 0.01 | >200 | <0.01 | 1.5 | 1 | 9 | 0.2 | 150 | 0.01 |
| GS14K4 | 50 | 4 | 100 | 2 | 2 | 100 | 25 | 8 | 1.5 | 133 | 1.5 | 133 | 62 | 32 |
| L3/A3 | >200 | 4 | >200 | 4 | >200 | 4 | >200 | 4 | >200 | 4 | 100 | 16 | >200 | 4 |
| V3/A3 | >200 | 4 | >200 | 4 | 50 | 32 | >200 | 4 | >200 | 4 | 3.1 | 520 | 50 | 32 |
| V3L3/A6 | >200 | 4 | >200 | 4 | >200 | 4 | >200 | 4 | >200 | 4 | 200 | 8 | 400 | 4 |
| V3/L3 | 12.5 | 2 | 25 | 1 | 1.5 | 17 | 9 | 2.8 | 1.5 | 17 | 1 | 25 | 4 | 6.3 |
| Y2/F2 | 9 | 4.4 | 12.5 | 3.2 | 3.1 | 13 | 12.5 | 3.2 | 6.2 | 6.5 | 1.5 | 27 | 3.1 | 13 |
| Y2/F2 V3/L3 | 9 | 1.4 | 9 | 1.4 | 2 | 6.3 | 6.2 | 2 | 1.5 | 8.3 | 1 | 12.5 | 3.1 | 4 |

[1]Therapeutic index = hemolytic activity/antibacterial activity. For the calculation of the therapeutic index, values of 400 μg/ml were used for MIC values of >200 μg/ml and values of 1600 μg/ml were used for hemolytic activity values of >800 μg/ml.

TABLE 7

Sequences and properties of GS14 nonamphipathic analogs

| Peptide | Linear Sequence[a] | LPS binding affinity (μM)[b] | Hemolytic activity (μg/ml)[c] | Retention Time (min.)[d] |
|---|---|---|---|---|
| GS14 | VKLKV$\underline{Y}$PLKVKL$\underline{Y}$P | 3 | 1.5 | 49.5 |
| GS14na | VKL$\underline{V}$K$\underline{Y}$PLKVL$\underline{K}$YP | ND | >800 | 32.8 |
| GS14napol | LVLKK$\underline{Y}$PKKVLV$\underline{Y}$P | 98 | 800 | 35.4 |
| GS14inv | KVKLK$\underline{Y}$PKVKLK$\underline{Y}$P | 14 | >800 | 28.0 |
| GS14invK1 | $\underline{K}$VKLK$\underline{Y}$PKVKLK$\underline{Y}$P | 43 | >800 | 25.9 |
| GS14invV2 | K$\underline{V}$KLK$\underline{Y}$PKVKLK$\underline{Y}$P | 71 | 800 | 25.1 |

[a]Linear sequences of cyclic peptides. Underlined residues represent D-amino acids.
[b]Peptide concentration to displace 50% of dansyl-polymyxin B from LPS. ND not determined
[c]Peptide concentration for 100% lysis of human erythrocytes.
[d]Retention time on reversed-phase HPLC.

TABLE 8

Activity of GS14 non-amphipathic analogs against gram negative microorganisms

Minimum Inhibitory Concentration (μg/mL) and Therapeutic Index[1]

| Peptide | P. aeruginosa H187 activity | index | P. aeruginosa H188 activity | index | E. coli UB1005 activity | index | E. coli DC2 activity | index | S. typhinurium C587 activity | index | S. typhinurium C610 activity | index |
|---|---|---|---|---|---|---|---|---|---|---|---|---|
| GS14 | >200 | <0.01 | >200 | <0.01 | >200 | <0.01 | >200 | <0.01 | >200 | <0.01 | >200 | <0.01 |
| GS14na | 75 | 21 | 18 | 90 | 37 | 43 | 62 | 260 | 100 | 16 | 12.5 | 130 |
| GS14napol | 50 | 16 | 9 | 90 | 18 | 45 | 4 | 200 | 50 | 16 | 25 | 32 |
| GS14inv | 12.5 | 130 | 6.2 | 260 | 12.5 | 130 | 0.8 | 2000 | 50 | 32 | 3.1 | 520 |
| GS14invK1 | 12.5 | 130 | 9 | 180 | 25 | 65 | 25 | 65 | 150 | 11 | 62 | 260 |
| GS14invV2 | 9 | 90 | 9 | 90 | 25 | 32 | 50 | 16 | 200 | 4 | 37 | 22 |

[1]Therapeutic index = hemolytic activity/antibacterial activity. For the calculation of the therapeutic index, values of 400 μg/ml were used for MIC values of >200 μg/ml and values of 1600 μg/ml were used for hemolytic activity values of >800 μg/ml.

TABLE 9

Antifungal and gram positive activity of GS14 non-amphipathic analogs

Minimum Inhibitory Concentration (μg/mL) and Therapeutic Index[1]

| Peptide | S. aureus SAP0017 activity | index | S. aureus K147 activity | index | S. epidermidis activity | index | B. subtilis activity | index | E. faecalis activity | index | C. xeroses activity | index | C. Albicans activity | index |
|---|---|---|---|---|---|---|---|---|---|---|---|---|---|---|
| GS | >200 | <0.01 | >200 | <0.01 | 200 | 0.01 | >200 | <0.01 | 1.5 | 1 | 9 | 0.2 | 150 | 0.01 |
| GS14na | 200 | 8 | >200 | <8 | 50 | 32 | >200 | <8 | 200 | 8 | 1.5 | 1100 | 100 | 16 |
| GS14napol | 200 | 4 | >200 | <5 | 25 | 32 | >200 | <4 | 75 | 11 | 1.2 | 1300 | 37 | 22 |
| GS14inv | 200 | 8 | >200 | <8 | 25 | 64 | >200 | <8 | 200 | 8 | 0.8 | 2000 | 25 | 64 |

TABLE 9-continued

Antifungal and gram positive activity of GS14 non-amphipathic analogs

Minimum Inhibitory Concentration (μg/mL) and Therapeutic Index[1]

| Peptide | S. aureus SAP0017 activity | index | S. aureus K147 activity | index | S. epidermidis activity | index | B. subtilis activity | index | E. faecalis activity | index | C. xeroses activity | index | C. Albicans activity | index |
|---|---|---|---|---|---|---|---|---|---|---|---|---|---|---|
| GS14invK1 | >200 | <8 | >200 | <8 | 100 | 16 | >200 | <8 | >200 | <8 | 6.2 | 260 | 200 | 8 |
| GS14invV2 | >200 | <4 | >200 | <4 | 100 | 8 | >200 | <4 | >200 | <4 | 6.2 | 130 | 200 | 4 |

[1]Therapeutic index = hemolytic activity/antibacterial activity. For the calculation of the the index, values of 400 μg/ml were used for MIC values of >200 μg/ml and values of 1600 μg/ml were used for hemolytic activity values of >800 μg/ml.

TABLE 10

SEQUENCES AND BIOLOGICAL AND PHYSICAL PROPERTIES OF CYCLIC GS RING ANALOGS

| PEPTIDE | LINEAR SEQUENCE[a] | RETENTION TIME MIN[b] | ANTIBIOTIC ACTIVITY (μG/ML)[c] AND THERAPEUTIC INDEX[d] | | | | | |
|---|---|---|---|---|---|---|---|---|
| | | | GRAM-POSITIVE ACTIVITY | INDEX | GRAM-NEGATIVE ACTIVITY | INDEX | YEAST ACTIVITY | INDEX |
| GS12 | YPVKLKYPKVKL | 22.3 | 240 | 1.0 | 32 | 7.8 | 42 | 6.0 |
| GS12LV | YPLKVKYPKLKV | 22.2 | 240 | 0.4 | 25 | 3.7 | 50 | 1.8 |
| GS12F | FPVKLKFPKVKL | 24.3 | 110 | 3.6 | 16 | 25 | 13 | 30 |
| GS12FO | FPVOLOFPOVOL | 24.8 | 120 | 1.3 | 16 | 10 | 16 | 10 |
| GS12FO/LL | FPLOLOFPOLOL | 26.1 | 42 | 4.0 | 18 | 9.4 | 16 | 11 |

| PEPTIDE | LINEAR SEQUENCE[a] | HEMOLYTIC ACTIVITY μG/ML[e] | LPS BINDING ACTIVITY μM[f] | B-SHEET CONTENT[g] |
|---|---|---|---|---|
| GS12 | YPVKLKYPKVKL | 250 | 46 | — |
| GS12LV | YPLKVKYPKLKV | 92 | 33 | — |
| GS12F | FPVKLKFPKVKL | 400 | 127 | — |
| GS12FO | FPVOLOFPOVOL | 160 | 105 | — |
| GS12FO/LL | FPLOLOFPOLOL | 170 | 44 | — |

[a]Linear sequences of cyclic peptides. Underlined residues represent D-amino acids. O is ornithine.
[b]Retention time on reversed-phase HPLC.
[c]Average activity calculated from Table II.
[d]Therapeutic index = hemolytic activity/antibiotic activity.
[e]Hemolytic activity determined using human erythrocytes.
[f]Peptide concentration to displace 50% of dansyl-polymyxin from LPS as calculated from FIG. 3.
[g]Determined by CD spectroscopy as shown in FIG. 1.

The following examples illustrate, but in no way are intended to limit the present invention.

Materials and Methods

A. Bacterial Strains

The following bacterial strains were utilized: *Escherichia coli* UB1005 (wt) and its antibiotic supersusceptible derivative DC2 (Clark, 1984); *Excherichia coli* SC9251 and its polymixin B rasistant mutant pmrASC9252 (Peterson, et al., 1987) *Pseudomonas aeruginosa* H187 (wt) (Angus, et al., 1987) and its antibiotic-sensitive derivative H188 (Zimmerman, W, Antimicrob. Agents Chemother. 18: 94–100, 1980); methicillin sensitive *Staphylococcus aureus* K147 (Kreiswirth, et al., 1983); *Staphylococcus aureus* SAP0017, a methicillin resistant clinical isolate from Dr. A. Chow (University of British Columia); *Bacillus subtilis*, an environmental wt lab strain. *Enterococcus faecalis* are ATCC 29212 cells and *Staphylococcus epidermidis* was a clinical isolate from Dr. D. Speert (University of British Columbia). Antifungal activity was tested using a clinical lab isolate of *Candida albicans*. *Salmonella typhinurium* C57 and C610 (Fields, P.I., et al., Science 243: 1059–1062 (1989) *Corynebacterium xerosis* was an environmental isolate (University of British Columbia).

Abbreviations used in the following sections are as listed below:
Boc: tert-butyloxycarbonyl
BOP: benzotriazoyl N-oxytris(dimethylamino) phosphonium hexafluorophosphate
DCC: N,N-dicyclohexylcarbodiimide
DCM: dichlormethane
DIEA: N,N-diisopropylethylamine
DMF: N,N-dimethylformamide
DQF-COSY: double quantum filtered correlation spectroscopy
DSS: 2,2-dimethyl-2-silapentane-5-sulfonate, sodium salt
EDAC: 1-ethyl-3-(3-dimethylaminopropyl)carbodiimide
HBTU 2-(1H-benzotriazol-1-yl)-1,1,3,3-tetramethyl uronium hexafluorophosphate
HPLC: high performance liquid chromatography
HOBt: 1-hydroxybenzotriazole
NHS: N-hydroxysuccinimide
NMR: nuclear magnetic resonance
NOESY: nuclear overhauser effect spectroscopy PAM: Phenylacetamidomethyl (resin)
TOCSY: total correlation spectroscopy
Troc: 2,2,2-trichloroethylcarbamate
RPHPLC: Reversed-phase high performance liquid chromatography Sources of Materials: Unless otherwise indicated, Tert-butyloxycarbonyl (t-Boc) amino acids including Boc-His (Tos), Boc-Cys(4-MeBzl), Boc-Lys(2-ClZ), Boc-Tyr(Bzl), N-hydroxybenzotriazole (HOBt) and N,N'-dicyclohexyl-carbodiimide (DCC) were purchased from Advanced Chemtech (Louisville, Ky.). Precoupled Phenylacetamidomethyl (PAM) resins (Boc-Lys(2ClZ)-PAM or Boc-Orn(Z)-PAM) were obtained from Novabiochem (San Diego, Calif.). Dichloromethane (DCM), N,N-dimethylformamide (DMF), HPLC-grade acetonitrile, N,N'-diisopropylethylamine (DIEA) and trifluoroacetic acid (TFA) were obtained from General Intermediates of Canada (Edmonton, AB). TFA was distilled, DCM re-distilled over calcium carbonate and DIEA over ninhydrin.

EXAMPLE 1

Peptide Synthesis and Purification

Standard t-BOC Method

Peptides were synthesized by solid-phase peptide synthesis using precoupled Boc-Pro-phenylacetamidomethyl resin (Novabiochem, San Diego, Calif.) on an Applied Biosystems model 430A peptide synthesizer (Foster City, Calif.) using standard t-butyloxycarbonyl chemistry (Erickson and Merrifield, 1976) as reported (Wishart, et al., 1996; Example 1). Side-chain protecting groups were 2-bromobenzyloxycarbonyl (2-BrZ) for tyrosine and formyl for lysine, ornithine, 2,4-diaminobutyric acid and 2,3-diaminopropionic acid; tosyl for arginine; trityl for histidine. Side-chain formylation was carried out by the procedure of Kitagawa, et al. (1994) using either Nα-Boc-lysine, Nα-Boc-ornithine, Nα-Boc-2,4-diaminobutyric acid or Nα-Boc-2,3-diaminoproprionic acid as starting materials. Peptides were cleaved from the resin using anhydrous hydrogen fluoride (20 mL/g resin) in the presence of 10% anisole for 1 h at −5° C. Peptides were extracted from the resin with glacial acetic acid and lyophilized. Crude linear peptides were purified by reversed-phase HPLC on a Synchropak RP-4 preparative C8 column (250×21.2 mm I.D., 6.5 μm particle size, 300 Å pore size) (Synchrom, Lafayette, Ind.) using a Beckman System Gold HPLC system (San Ramon, Calif.). The flow rate was 5 mL/min with a linear AB gradient of 0.25% B/min where solvent A was 0.05% TFA/$H_2O$ and solvent B was 0.05% TFA/acetonitrile. Typical yields of linear peptides were in the range of 65%. Purity of peptides was verified by analytical reversed-phase HPLC on a Zorbax SB-C8 column (250×4.6 mm I.D., 5 μm particle size, 300 Å pore size) (Rockland Technologies, Wilmington, Del.) using a Hewlett Packard 1090 chromatograph with a linear AB gradient of 2% B/min and a 1 mL/min flow rate. Identity of peptides was confirmed by mass spectrometry on a Fisons VG Quattro triple quadrupole mass spectrometer (Manchester, England) fitted with an electrospray ionization source operating in positive ion mode.

Pure linear formylated peptides were cyclized at a concentration of 2 mg/mL in N,N-dimethylformamide using 3 equivalents of each of benzotriazolyl N-oxytridimethylamino-phosphonium hexafluorophosphate, 1-hydroxybenzotriazole and diisopropylethylamine. The progress of the cyclization reaction was monitored by analytical reversed-phase HPLC and was typically complete after 1 h. Cyclic peptides were deformylated (10% HCl in methanol, 37° C. for 24 hr.) and purified by preparative reversed-phase HPLC. Yields of cyclic product were typically in the range of 60–70%. Purified cyclic peptides were homogeneous by analytical reversed-phase HPLC and gave correct primary ion molecular weights by mass spectrometry as well as appropriate amino acid analysis ratios. Peptide concentration used for some assays was based on weight and may underestimate the actual amount of peptide. For the majority of assays, solutions were made in water and accurate concentrations were determined by amino acid analysis.

EXAMPLE 2

Solid Phase Synthesis of Cyclic Peptides

Beginning with either Boc-Lys(2ClZ)-PAM or Boc-Orn(Z)-PAM (substitution of 0.4 to 0.65 mmol/g of resin), linear GS analog peptides (such as: peptide 1, C at position 4; peptide 2, K at positions 5 and 10; peptide 3, K at positions 5 and 10 and Y at positions 2 and 7) were synthesized using an Applied Biosystems 430A automated peptide synthesizer. Standard deprotection (TFA/DCM 1:1), wash (DCM 3×, DMF 2×) and coupling steps (using preformed symmetric anhydrides in DCM, coupling in DMF/DCM) were performed for each round of the synthesis. The blocked peptides were cleaved from the resin using anhydrous HF (20 mL/g resin) in the presence of 10% anisole and 2% 1,2-ethanedithiol for 1 h at −5° C. The crude linear peptides were purified using a reversed-phase C8 semi-preparative Synchropak column (Synchrom, Lafayette, Ind.) with a linear AB gradient of 0.25% B/min, where A=0.05% TFA/$H_2O$ and B=0.05% TFA/acetonitrile, at a flow rate of 2 mL/min. Purity of the peptides was verified by analytical reversed-phase HPLC on a Zorbax SB-C8 column (Rockland Technologies, Wilmington, Del.) using a Hewlett Packard 1090 chromatogram with a linear AB gradient of 2% B/min and a 1 mL/min flow rate. Identity of the peptides was confirmed by time-of-flight mass spectrometry (BIOION-2 Nordic, Uppsala, Sweden).

For cyclization after purification, the unprotected linear peptide (concentration ~2 mg/mL) was placed in a small flask (25 mL) containing DCM with 1.2 equivalents each of DCC, HOBt and DIEA and stirred vigorously with a magnetic stirrer at room temperature for up to 24 hours. The progress of the cyclization reaction was monitored by both analytical reversed phase HPLC (see above) and plasma desorption time-of-flight mass spectrometry (BIOION-20 Nordic, Uppsala). For GS, cyclizations were typically complete after six hours with final overall yields often approaching 80%. One of the analogs (GS with D-His at positions 2 and 7, K at positions 5 and 10) took longer to cyclize (~24 hours) and the overall yield was much lower (15%). Final purification of the cyclic peptides was achieved with reversed phase HPLC using identical conditions for the linear peptides.

EXAMPLE 3

Circular Dichroism Measurements

Circular dichroism spectra were recorded on a Jasco J-500C spectropolarimeter (Jasco, Easton, Md.) equipped with a Jasco DP-500N data processor The instrument was routinely calibrated with an aqueous solution of d-10-(+)-camphorsulfonic acid at 290.5 nm. Ellipticity is reported as mean residue ellipticity ([θ]) in deg*$cm^2$/dmol calculated from the following equation: $[\theta]=[\theta]_{obs}(mrw)/10lc$ where [θ] in the ellipticity measured in degrees, mrw is the mean residue weight, c is the peptide concentration in grams/mL and l is the optical path length of the cell in cm. Spectra were recorded in 10mM sodium acetate buffer, pH 5.5, and were the average of four scans obtained by collecting data at 0.1 nm intervals between 255 and 190 nm.

EXAMPLE 4

Molecular Modelling

Models of ring size analogs were built using insight II (Biosym Technologies Inc., San Diego, Calif.) on a Silicon Graphics workstation. Models of the 10, 12 and 14 residue peptides were constructed by specifying standard antiparallel β-sheet (ϕ,ψ) value of −139° and 135°, respectively (Creighton, 1984). Two type II β-turns were incorporated into each structure designation D-Tyr and Pro residues as residues i+1 and i+2 of the turns. Dihedral angels (ϕ, ψ) used for the turns were 60°, −120° and −80°, 0° for i+1 and i+2 residues, respectively (Creighton, 1984). The N-termini of the analogs was arbitrarily chosen as a residue contained within the strands for the models only; chemically synthesized peptides used Pro as the carboxyl terminus in all cases.

EXAMPLE 5

Measurement of Antibacterial and Antifungal Activity

It is now apparent that agar-based assays severely underestimate antifungal activity as well as activity against gram negative microorganisms (Kondejewski, et al., 1996). Consequently, in the studies reported herein, a liquid-broth method was used to measure the antibiotic properties of the peptides. Minimum Inhibitory Concentration (MIC) was determined using a standard microtitre dilution method in LB no salt medium (10 g tryptone and 5 g of yeast extract per L). Briefly, cells were grown overnight at 37° C. in LB and diluted in the same medium. Serial dilutions of antibiotics were added to the microtitre plates in a volume of 100 μL followed by 10 μL of bacteria to give a final inoculum of 5×10$^5$ CFU/mL. Plates were incubated at 37° C. overnight and MICs determined as the lowest antibiotic concentration that inhibited growth.

EXAMPLE 6

Measurement of Hemolytic Activity

Freshly collected human blood with heparin was centrifuged to remove the buffy coat, and the erythrocytes obtained were washed three times in 0.85% saline and stored at 4° C. Serial dilutions of the peptides in saline were prepared in round bottom microtitre plates using 100 μL volumes. Red blood cells were diluted with saline to 1/25 packed volume of cells and 50 μL added to each well. Plates were incubated with rocking at 37° C., and the concentration required for complete lysis determined visually after 4 h.

EXAMPLE 7

Permeabilization of Outer Membranes to NPN

Permeabilization studies were carried out as follows: Briefly, *Escherichia coli* SC9251 cells were suspended in 5 mM sodium HEPES buffer, pH 7.0, containing 5 mM glucose and 5 mM carbonyl cyanide m-chlorophenylhydrazone. NPN was added to 1 mL of cells in a quartz cuvette to give a final concentration of 10 mM and the background fluorescence recorded. Aliquots of peptide were added to the cuvette and fluorescence recorded as a function of time until there was no further increase in fluorescence. A fresh cuvette of cells with NPN was used for each concentration for each peptide and control experiments were performed to demonstrate that enhanced fluorescence was due to uptake of NPN into cells, as described previously (Hancock and Wong, 1984; Loh, et al., 1984; Hancock, 1981).

EXAMPLE 8

Displacement of Dansyl-Polymixin from LPS

Dansyl-polymixin (DPX) displacement from *P. aeruginosa* LPS was measured as described (Moore, et al., 1986). Briefly, peptides were titrated into cuvettes containing 3 μg of LPS per mL and 2.5 μM dansyl-polymixin (approximately 90% saturation of LPS binding sites) in 1 mL of 5 mM sodium HEPES buffer, pH 7.0, and the decrease in fluorescence recorded. A plot of the inverse of the percent inhibition as a function of the inverse of inhibitor concentration gave a value for $I_{50}$, the inhibitor concentration resulting in 50% displacement of dansyl-polymixin from LPS (−1/x intercept).

EXAMPLE 9

Determination of Therapeutic Index

The results from antimicrobial and hemolytic assays are combined to provide a "Therapeutic Index" (TI) for each peptide with respect to individual microorganisms. As reported herein, the TI is calculated as the hemolytic activity divided by the antimicrobial activity. The TI thus is a measure of specificity of the particular peptide for microbial membranes as opposed to human blood cell membranes. In the present studies, antimicrobial activities are reported as minimum inhibitory concentrations (MIC)—the lowest concentration of peptide (μg/ml) found to inhibit growth of the particular microbe. Hemolytic activity is reported as the concentration of peptide that effected complete lysis of blood cells after four hours. Thus, in the context of the present invention high TI values indicate microbial specificity and relative lack of toxicity.

EXAMPLE 10

Analytical Reversed-Phase Analysis of Peptides

Pure cyclic peptides were analyzed by RP-HPLC on a Zorbax SB-C8 column (150×2.1 mm I.D., 5 μm particle size, 300 pore size; Rockland Technologies, Wilmington, Del.) using a Hewlett Packard 1100 chromatograph at either 25° C. or 70° C. with a linear AB gradient of either 0.5% or 1% B/min (where solvents A and B are as described above) and a flow rate of 0.25 ml/min. For analysis of diastereomers, 1% B/min, 70 degrees; for analysis of hydrophobic same class substitutions, 1% B/min, 25 degrees; for analysis of basic same class substitutions using 10-mers, 0.5% B/min., 30 degrees; for analysis of GS14inv, GS14invK1, GS14invV2, GS14na and GS14napol, 1% B/min, 25 degrees.

EXAMPLE 11

Nuclear Magnetic Spectroscopy NMR

All NMR specra were collected under aqueous conditions on a Varian Unity 200 MHz spectrometer equipped with a 5 mm inverse detection probe. Each peptide was dissolved in 500 μl of 80%H20/20%D20 (or 100% D20) giving a sample concentration of approximately 1–2 mM. The sample temperature was maintained at 25 degrees C. and the pH was adjusted to 5.5. 1H DQF-COSY (Piantini), NOESY (Kumar) and TOCSY (Braunschweiler) spectra were collected and processed using standard methods. Quadrature detection was achieved using the method of States et al. Alll 1H chemical shifts were referenced to internal DSS at 0.00 ppm.

While the invention has been described with reference to specific methods and embodiments, it will be appreciated that various modifications and changes may be made without departing from the invention.

It is claimed:

1. A 14-mer cyclic peptide having an amino acid substitution in the amino acid sequence V1-K2-L3-K4-V5-Y6-P7-L8-K9-V10-K11-L12-Y13-P14 also identified by SEQ ID NO: 1, where Y represents D-tyrosine, numerals represent relative positions in said peptide, P14 is linked to V1, and said amino acid substitution is a D-amino acid in at least one of positions 1–5, 7–12 and 14, or an L-amino acid in position 6 or 13, and further characterized by a therapeutic index of greater than 1, wherein said therapeutic index value is determined as a ratio of the concentration of peptide required to produce hemolysis of human red blood cells divided by the concentration of peptide required to inhibit growth of a specified microorganism.

2. The peptide of claim 1 wherein said specified microorganism is selected from the group consisting of Pseudomonas, Escherischia coli, Salmonella, Staphylococcus, Bacillus, Enterococcus, Corynebaterium, and Candida.

3. The peptide of claim 1 wherein said amino acid substitution is D-valine at a position selected from the group consisting of position 1 and position 5.

4. The peptide of claim 1 wherein said amino acid substitution is D-valine at position 10.

5. The peptide of claim 1 wherein said amino acid substitution is D-leucine at a position selected from the group consisting of position 8 and position 12.

6. The peptide of claim 1 wherein said amino acid substitution is D-leucine at position 3.

7. The peptide of claim 1 wherein said amino acid substitution is D-lysine at a position selected from the group consisting of position 2, position 4, position 9 and position 11.

8. The peptide of claim 1 further comprising an amino acid substitution at any of positions 1, 3, 5, 8, 10 or 12 with an amino acid selected from the group consisting of alanine, valine, leucine, norvaline, isoleucine, norleucine, methionine, phenylalanine, tyrosine and tryptophan.

9. The peptide of claim 7 further comprising additional amino acid substitutions selected from the group consisting of leucine at each of positions 1, 5 and 10; alanine at each of positions 3, 8 and 12, and an alanine at each of positions 1, 5 and 10.

10. The peptide of claim 9 wherein said additional substitutions consist of leucine at each of positions 1, 5 and 10 further comprising D-phenylalanine at each of positions 6 and 13.

11. The peptide of claim 10 wherein said amino acid substitution is D-lysine at position 4.

* * * * *

UNITED STATES PATENT AND TRADEMARK OFFICE
CERTIFICATE OF CORRECTION

PATENT NO. : 6,358,921 B1
DATED : March 19, 2001
INVENTOR(S) : Leslie H. Kondejewski et al.

It is certified that error appears in the above-identified patent and that said Letters Patent is hereby corrected as shown below:

Column 95,
Line 58, "Corynebaterium" should read -- Corynebacterium --.

Signed and Sealed this

Eighteenth Day of June, 2002

Attest:

Attesting Officer

JAMES E. ROGAN
Director of the United States Patent and Trademark Office

```
                            SEQUENCE LISTING (1) GENERAL INFORMATION:

(iii) NUMBER OF SEQUENCES: 42

(2) INFORMATION FOR SEQ ID NO:1:

(i) SEQUENCE CHARACTERISTICS:
         (A) LENGTH: 14 amino acids
         (B) TYPE: amino acid
         (C) STRANDEDNESS:
         (D) TOPOLOGY: cyclic (ii) MOLECULE TYPE: peptide (iii) HYPOTHETICAL: NO (iv) ANTI-SENSE: NO (ix) FEATURE:
         (A) NAME/KEY: Modified-site
         (B) LOCATION: 6
         (D) OTHER INFORMATION: /note= "Where Xaa is D-Tyrosine or
             D-phenylalanine"

(ix) FEATURE:
         (A) NAME/KEY: Modified-site
         (B) LOCATION: 13
         (D) OTHER INFORMATION: /note= "Where Xaa is D-Tyrosine or
             D-phenylalanine"

(xi) SEQUENCE DESCRIPTION: SEQ ID NO:1:

Val Lys Leu Lys Val Xaa Pro Leu Lys Val Lys Leu Xaa Pro
1               5                  10

(2) INFORMATION FOR SEQ ID NO:2:

(i) SEQUENCE CHARACTERISTICS:
         (A) LENGTH: 14 amino acids
         (B) TYPE: amino acid
         (C) STRANDEDNESS:
         (D) TOPOLOGY: cyclic (ii) MOLECULE TYPE: peptide (iii) HYPOTHETICAL: NO (iv) ANTI-SENSE: NO (ix) FEATURE:
         (A) NAME/KEY: Modified-site
         (B) LOCATION: 1
         (D) OTHER INFORMATION: /note= "Residue is a D-Valine "

(ix) FEATURE:
         (A) NAME/KEY: Modified-site
         (B) LOCATION: 6
         (D) OTHER INFORMATION: /note= "Residue is a D-Tyrosine"

(ix) FEATURE:
         (A) NAME/KEY: Modified-site
         (B) LOCATION: 13
         (D) OTHER INFORMATION: /note= "Residue is a D-Tyrosine"
```

```
       (xi) SEQUENCE DESCRIPTION: SEQ ID NO:2:

Xaa Lys Leu Lys Val Xaa Pro Leu Lys Val Lys Leu Xaa Pro
1               5                   10

(2) INFORMATION FOR SEQ ID NO:3:

(i) SEQUENCE CHARACTERISTICS:
           (A) LENGTH: 14 amino acids
           (B) TYPE: amino acid
           (C) STRANDEDNESS:
           (D) TOPOLOGY: cyclic (ii) MOLECULE TYPE: peptide (iii) HYPOTHETICAL: NO (iv) ANTI-SENSE: NO (ix) FEATURE:
           (A) NAME/KEY: Modified-site
           (B) LOCATION: 2
           (D) OTHER INFORMATION: /note= "Residue is a D-Lysine"

(ix) FEATURE:
           (A) NAME/KEY: Modified-site
           (B) LOCATION: 6
           (D) OTHER INFORMATION: /note= "Residue is a D-Tyrosine"

(ix) FEATURE:
           (A) NAME/KEY: Modified-site
           (B) LOCATION: 13
           (D) OTHER INFORMATION: /note= "Residue is a D-Tyrosine"

(xi) SEQUENCE DESCRIPTION: SEQ ID NO:3:

Val Xaa Leu Lys Val Xaa Pro Leu Lys Val Lys Leu Xaa Pro
1               5                   10

(2) INFORMATION FOR SEQ ID NO:4:

(i) SEQUENCE CHARACTERISTICS:
           (A) LENGTH: 14 amino acids
           (B) TYPE: amino acid
           (C) STRANDEDNESS:
           (D) TOPOLOGY: cyclic (ii) MOLECULE TYPE: peptide (ix) FEATURE:
           (A) NAME/KEY: Modified-site
           (B) LOCATION: 3
           (D) OTHER INFORMATION: /note= "Residue is a D-Leucine"

(ix) FEATURE:
           (A) NAME/KEY: Modified-site
           (B) LOCATION: 6
           (D) OTHER INFORMATION: /note= "Residue is a D-Tyrosine"

(ix) FEATURE:
           (A) NAME/KEY: Modified-site
           (B) LOCATION: 13
           (D) OTHER INFORMATION: /note= "Residue is a D-Tyrosine"

(xi) SEQUENCE DESCRIPTION: SEQ ID NO:4:

Val Lys Xaa Lys Val Xaa Pro Leu Lys Val Lys Leu Xaa Pro
1               5                   10

(2) INFORMATION FOR SEQ ID NO:5:

(i) SEQUENCE CHARACTERISTICS:
           (A) LENGTH: 14 amino acids
           (B) TYPE: amino acid
           (C) STRANDEDNESS:
           (D) TOPOLOGY: cyclic
```

```
        (ii) MOLECULE TYPE: peptide (ix) FEATURE:
              (A) NAME/KEY: Modified-site
              (B) LOCATION: 4
              (D) OTHER INFORMATION: /note= "Residue is a D-Lysine"

(ix) FEATURE:
              (A) NAME/KEY: Modified-site
              (B) LOCATION: 6
              (D) OTHER INFORMATION: /note= "Residue is a D-Tyrosine"

(ix) FEATURE:
              (A) NAME/KEY: Modified-site
              (B) LOCATION: 13
              (D) OTHER INFORMATION: /note= "Residue is a D-Tyrosine"

(xi) SEQUENCE DESCRIPTION: SEQ ID NO:5:

Val Lys Leu Xaa Val Xaa Pro Leu Lys Val Lys Leu Xaa Pro
1               5                  10

(2) INFORMATION FOR SEQ ID NO:6:

(i) SEQUENCE CHARACTERISTICS:
              (A) LENGTH: 14 amino acids
              (B) TYPE: amino acid
              (C) STRANDEDNESS:
              (D) TOPOLOGY: cyclic (ii) MOLECULE TYPE: peptide (iii) HYPOTHETICAL: NO (iv) ANTI-SENSE: NO (ix) FEATURE:
              (A) NAME/KEY: Modified-site
              (B) LOCATION: 5
              (D) OTHER INFORMATION: /note= "Residue is a D-Valine"

(ix) FEATURE:
              (A) NAME/KEY: Modified-site
              (B) LOCATION: 6
              (D) OTHER INFORMATION: /note= "Residue is a D-Tyrosine"

(ix) FEATURE:
              (A) NAME/KEY: Modified-site
              (B) LOCATION: 13
              (D) OTHER INFORMATION: /note= "Residue is a D-Tyrosine"

(xi) SEQUENCE DESCRIPTION: SEQ ID NO:6:

Val Lys Leu Lys Xaa Xaa Pro Leu Lys Val Lys Leu Xaa Pro
1               5                  10

(2) INFORMATION FOR SEQ ID NO:7:

(i) SEQUENCE CHARACTERISTICS:
              (A) LENGTH: 14 amino acids
              (B) TYPE: amino acid
              (C) STRANDEDNESS:
              (D) TOPOLOGY: cyclic (ii) MOLECULE TYPE: peptide (iii) HYPOTHETICAL: NO (iv) ANTI-SENSE: NO (ix) FEATURE:
              (A) NAME/KEY: Modified-site
              (B) LOCATION: 13
              (D) OTHER INFORMATION: /note= "Residue is a D-Tyrosine"
```

(xi) SEQUENCE DESCRIPTION: SEQ ID NO:7:

Val Lys Leu Lys Val Tyr Pro Leu Lys Val Lys Leu Xaa Pro
1               5                   10

(2) INFORMATION FOR SEQ ID NO:8:

(i) SEQUENCE CHARACTERISTICS:
        (A) LENGTH: 14 amino acids
        (B) TYPE: amino acid
        (C) STRANDEDNESS:
        (D) TOPOLOGY: cyclic (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 6
        (D) OTHER INFORMATION: /note= "Residue is a D-Tyrosine"

(ix) FEATURE:
        (A) NAME/KEY: Modified-site
        (B) LOCATION: 7
        (D) OTHER INFORMATION: /note= "Residue is a D-Proline"

(ix) FEATURE:
        (A) NAME/KEY: Modified-site
        (B) LOCATION: 13
        (D) OTHER INFORMATION: /note= "Residue is a D-Tyrosine"

(xi) SEQUENCE DESCRIPTION: SEQ ID NO:8:

Val Lys Leu Lys Val Xaa Xaa Leu Lys Val Lys Leu Xaa Pro
1               5                   10

(2) INFORMATION FOR SEQ ID NO:9:

(i) SEQUENCE CHARACTERISTICS:
        (A) LENGTH: 14 amino acids
        (B) TYPE: amino acid
        (C) STRANDEDNESS:
        (D) TOPOLOGY: cyclic (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 6
        (D) OTHER INFORMATION: /note= "Residue is a D-Tyrosine"

(ix) FEATURE:
        (A) NAME/KEY: Modified-site
        (B) LOCATION: 8
        (D) OTHER INFORMATION: /note= "Residue is a D-Leucine"

(ix) FEATURE:
        (A) NAME/KEY: Modified-site
        (B) LOCATION: 13
        (D) OTHER INFORMATION: /note= "Residue is a D-Tyrosine"

(xi) SEQUENCE DESCRIPTION: SEQ ID NO:9:

Val Lys Leu Lys Val Xaa Pro Xaa Lys Val Lys Leu Xaa Pro
1               5                   10

(2) INFORMATION FOR SEQ ID NO:10:

(i) SEQUENCE CHARACTERISTICS:
        (A) LENGTH: 14 amino acids
        (B) TYPE: amino acid
        (C) STRANDEDNESS:
        (D) TOPOLOGY: cyclic (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 6
        (D) OTHER INFORMATION: /note= "Residue is a D-Tyrosine"

(ix) FEATURE:
        (A) NAME/KEY: Modified-site
        (B) LOCATION: 9
        (D) OTHER INFORMATION: /note= "Residue is a D-Lysine"

(ix) FEATURE:
        (A) NAME/KEY: Modified-site
        (B) LOCATION: 13
        (D) OTHER INFORMATION: /note= "Residue is a D-Tyrosine"

(xi) SEQUENCE DESCRIPTION: SEQ ID NO:10:

```
Val Lys Leu Lys Val Xaa Pro Leu Xaa Val Lys Leu Xaa Pro
1               5                   10
```

(2) INFORMATION FOR SEQ ID NO:11:

(i) SEQUENCE CHARACTERISTICS:
        (A) LENGTH: 14 amino acids
        (B) TYPE: amino acid
        (C) STRANDEDNESS:
        (D) TOPOLOGY: cyclic (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 6
        (D) OTHER INFORMATION: /note= "Residue is a D-Tyrosine"

(ix) FEATURE:
        (A) NAME/KEY: Modified-site
        (B) LOCATION: 10
        (D) OTHER INFORMATION: /note= "Residue is a D-Valine"

(ix) FEATURE:
        (A) NAME/KEY: Modified-site
        (B) LOCATION: 13
        (D) OTHER INFORMATION: /note= "Residue is a D-Tyrosine"

(xi) SEQUENCE DESCRIPTION: SEQ ID NO:11:

```
Val Lys Leu Lys Val Xaa Pro Leu Lys Xaa Lys Leu Xaa Pro
1               5                   10
```

(2) INFORMATION FOR SEQ ID NO:12:

(i) SEQUENCE CHARACTERISTICS:
        (A) LENGTH: 14 amino acids
        (B) TYPE: amino acid
        (C) STRANDEDNESS:
        (D) TOPOLOGY: cyclic (ii) MOLECULE TYPE: peptide (iii) HYPOTHETICAL: NO (iv) ANTI-SENSE: NO (ix) FEATURE:
                 (A) NAME/KEY: Modified-site
                 (B) LOCATION: 6
                 (D) OTHER INFORMATION: /note= "Residue is a D-Tyrosine"

(ix) FEATURE:
                 (A) NAME/KEY: Modified-site
                 (B) LOCATION: 11
                 (D) OTHER INFORMATION: /note= "Residue is a D-Lysine"

(ix) FEATURE:
                 (A) NAME/KEY: Modified-site
                 (B) LOCATION: 13
                 (D) OTHER INFORMATION: /note= "Residue is a D-Tyrosine"

(xi) SEQUENCE DESCRIPTION: SEQ ID NO:12:

Val Lys Leu Lys Val Xaa Pro Leu Lys Val Xaa Leu Xaa Pro
1               5                   10

(2) INFORMATION FOR SEQ ID NO:13:

(i) SEQUENCE CHARACTERISTICS:
                 (A) LENGTH: 14 amino acids
                 (B) TYPE: amino acid
                 (C) STRANDEDNESS:
                 (D) TOPOLOGY: cyclic (ii) MOLECULE TYPE: peptide (iii) HYPOTHETICAL: NO (iv) ANTI-SENSE: NO (ix) FEATURE:
                 (A) NAME/KEY: Modified-site
                 (B) LOCATION: 6
                 (D) OTHER INFORMATION: /note= "Residue is a D-Tyrosine"

(ix) FEATURE:
                 (A) NAME/KEY: Modified-site
                 (B) LOCATION: 12
                 (D) OTHER INFORMATION: /note= "Residue is a D-Leucine"

(ix) FEATURE:
                 (A) NAME/KEY: Modified-site
                 (B) LOCATION: 13
                 (D) OTHER INFORMATION: /note= "Residue is a D-Tyrosine"

(xi) SEQUENCE DESCRIPTION: SEQ ID NO:13:

Val Lys Leu Lys Val Xaa Pro Leu Lys Val Lys Xaa Xaa Pro
1               5                   10

(2) INFORMATION FOR SEQ ID NO:14:

(i) SEQUENCE CHARACTERISTICS:
                 (A) LENGTH: 14 amino acids
                 (B) TYPE: amino acid
                 (C) STRANDEDNESS:
                 (D) TOPOLOGY: cyclic (ii) MOLECULE TYPE: peptide (iii) HYPOTHETICAL: NO (iv) ANTI-SENSE: NO

```
    (ix) FEATURE:
         (A) NAME/KEY: Modified-site
         (B) LOCATION: 6
         (D) OTHER INFORMATION: /note= "Residue is a D-Tyrosine"

(xi) SEQUENCE DESCRIPTION: SEQ ID NO:14:

Val Lys Leu Lys Val Xaa Pro Leu Lys Val Lys Leu Tyr Pro
1               5                   10

(2) INFORMATION FOR SEQ ID NO:15:

(i) SEQUENCE CHARACTERISTICS:
        (A) LENGTH: 14 amino acids
        (B) TYPE: amino acid
        (C) STRANDEDNESS:
        (D) TOPOLOGY: cyclic (ii) MOLECULE TYPE: peptide (iii) HYPOTHETICAL: NO (iv) ANTI-SENSE: NO (ix) FEATURE:
         (A) NAME/KEY: Modified-site
         (B) LOCATION: 6
         (D) OTHER INFORMATION: /note= "Residue is a D-Tyrosine"

(ix) FEATURE:
         (A) NAME/KEY: Modified-site
         (B) LOCATION: 13
         (D) OTHER INFORMATION: /note= "Residue is a D-Tyrosine"

(ix) FEATURE:
         (A) NAME/KEY: Modified-site
         (B) LOCATION: 14
         (D) OTHER INFORMATION: /note= "Residue is a D-Proline"

(xi) SEQUENCE DESCRIPTION: SEQ ID NO:15:

Val Lys Leu Lys Val Xaa Pro Leu Lys Val Lys Leu Xaa Xaa
1               5                   10

(2) INFORMATION FOR SEQ ID NO:16:

(i) SEQUENCE CHARACTERISTICS:
        (A) LENGTH: 14 amino acids
        (B) TYPE: amino acid
        (C) STRANDEDNESS:
        (D) TOPOLOGY: cyclic (ii) MOLECULE TYPE: peptide (iii) HYPOTHETICAL: NO (iv) ANTI-SENSE: NO (ix) FEATURE:
         (A) NAME/KEY: Modified-site
         (B) LOCATION: 2
         (D) OTHER INFORMATION: /note= "Residue is a D-Lysine"

(ix) FEATURE:
         (A) NAME/KEY: Modified-site
         (B) LOCATION: 4
         (D) OTHER INFORMATION: /note= "Residue is a D-Lysine"

(ix) FEATURE:
         (A) NAME/KEY: Modified-site
         (B) LOCATION: 6
         (D) OTHER INFORMATION: /note= "Residue is a D-Tyrosine"

(ix) FEATURE:
         (A) NAME/KEY: Modified-site
         (B) LOCATION: 13
         (D) OTHER INFORMATION: /note= "Residue is a D-Tyrosine"
```

(xi) SEQUENCE DESCRIPTION: SEQ ID NO:16:

Val Xaa Leu Xaa Val Xaa Pro Leu Lys Val Lys Leu Xaa Pro
1               5                   10

(2) INFORMATION FOR SEQ ID NO:17:

(i) SEQUENCE CHARACTERISTICS:
         (A) LENGTH: 14 amino acids
         (B) TYPE: amino acid
         (C) STRANDEDNESS:
         (D) TOPOLOGY: cyclic (ii) MOLECULE TYPE: peptide (iii) HYPOTHETICAL: NO (iv) ANTI-SENSE: NO (ix) FEATURE:
          (A) NAME/KEY: Modified-site
          (B) LOCATION: 2
          (D) OTHER INFORMATION: /note= "Residue is a D-Lysine"

(ix) FEATURE:
          (A) NAME/KEY: Modified-site
          (B) LOCATION: 4
          (D) OTHER INFORMATION: /note= "Residue is a D-Lysine"

(ix) FEATURE:
          (A) NAME/KEY: Modified-site
          (B) LOCATION: 6
          (D) OTHER INFORMATION: /note= "Residue is a D-Tyrosine"

(ix) FEATURE:
          (A) NAME/KEY: Modified-site
          (B) LOCATION: 9
          (D) OTHER INFORMATION: /note= "Residue is a D-Lysine"

(ix) FEATURE:
          (A) NAME/KEY: Modified-site
          (B) LOCATION: 11
          (D) OTHER INFORMATION: /note= "Residue is a D-Lysine"

(ix) FEATURE:
          (A) NAME/KEY: Modified-site
          (B) LOCATION: 13
          (D) OTHER INFORMATION: /note= "Residue is a D-Tyrosine"

(xi) SEQUENCE DESCRIPTION: SEQ ID NO:17:

Val Xaa Leu Xaa Val Xaa Pro Leu Xaa Val Xaa Leu Xaa Pro
1               5                   10

(2) INFORMATION FOR SEQ ID NO:18:

(i) SEQUENCE CHARACTERISTICS:
         (A) LENGTH: 14 amino acids
         (B) TYPE: amino acid
         (C) STRANDEDNESS:
         (D) TOPOLOGY: cyclic (ii) MOLECULE TYPE: peptide (iii) HYPOTHETICAL: NO (iv) ANTI-SENSE: NO (ix) FEATURE:
          (A) NAME/KEY: Modified-site
          (B) LOCATION: 4
          (D) OTHER INFORMATION: /note= "Residue is a D-Lysine"

(ix) FEATURE:
          (A) NAME/KEY: Modified-site
          (B) LOCATION: 6
          (D) OTHER INFORMATION: /note= "Residue is a D-Tyrosine"

```
        (ix) FEATURE:
              (A) NAME/KEY: Modified-site
              (B) LOCATION: 13
              (D) OTHER INFORMATION: /note= "Residue is a D-Tyrosine"

(xi) SEQUENCE DESCRIPTION: SEQ ID NO:18:

Asx Lys Ala Xaa Val Xaa Pro Ala Lys Val Lys Ala Xaa Pro
1               5                  10

(2) INFORMATION FOR SEQ ID NO:19:

(i) SEQUENCE CHARACTERISTICS:
              (A) LENGTH: 14 amino acids
              (B) TYPE: amino acid
              (C) STRANDEDNESS:
              (D) TOPOLOGY: cyclic (ii) MOLECULE TYPE: peptide (iii) HYPOTHETICAL: NO (iv) ANTI-SENSE: NO (ix) FEATURE:
              (A) NAME/KEY: Modified-site
              (B) LOCATION: 4
              (D) OTHER INFORMATION: /note= "Residue is a D-Lysine"

(ix) FEATURE:
              (A) NAME/KEY: Modified-site
              (B) LOCATION: 6
              (D) OTHER INFORMATION: /note= "Residue is a D-Tyrosine"

(ix) FEATURE:
              (A) NAME/KEY: Modified-site
              (B) LOCATION: 13
              (D) OTHER INFORMATION: /note= "Residue is a D-Tyrosine"

(xi) SEQUENCE DESCRIPTION: SEQ ID NO:19:

Ala Lys Leu Xaa Ala Xaa Pro Leu Lys Ala Lys Leu Xaa Pro
1               5                  10

(2) INFORMATION FOR SEQ ID NO:20:

(i) SEQUENCE CHARACTERISTICS:
              (A) LENGTH: 14 amino acids
              (B) TYPE: amino acid
              (C) STRANDEDNESS:
              (D) TOPOLOGY: cyclic (ii) MOLECULE TYPE: peptide (iii) HYPOTHETICAL: NO (iv) ANTI-SENSE: NO (ix) FEATURE:
              (A) NAME/KEY: Modified-site
              (B) LOCATION: 4
              (D) OTHER INFORMATION: /note= "Residue is a D-Lysine"

(ix) FEATURE:
              (A) NAME/KEY: Modified-site
              (B) LOCATION: 6
              (D) OTHER INFORMATION: /note= "Residue is a D-Tyrosine"

(ix) FEATURE:
              (A) NAME/KEY: Modified-site
              (B) LOCATION: 13
              (D) OTHER INFORMATION: /note= "Residue is a D-Tyrosine"

(xi) SEQUENCE DESCRIPTION: SEQ ID NO:20:

Ala Lys Ala Xaa Ala Xaa Pro Ala Lys Ala Lys Ala Xaa Pro
1               5                  10
```

(2) INFORMATION FOR SEQ ID NO:21:

(i) SEQUENCE CHARACTERISTICS:
        (A) LENGTH: 14 amino acids
        (B) TYPE: amino acid
        (C) STRANDEDNESS:
        (D) TOPOLOGY: cyclic (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 4
        (D) OTHER INFORMATION: /note= "Residue is a D-Lysine"

(ix) FEATURE:
        (A) NAME/KEY: Modified-site
        (B) LOCATION: 6
        (D) OTHER INFORMATION: /note= "Residue is a D-Tyrosine"

(ix) FEATURE:
        (A) NAME/KEY: Modified-site
        (B) LOCATION: 13
        (D) OTHER INFORMATION: /note= "Residue is a D-Tyrosine"

(xi) SEQUENCE DESCRIPTION: SEQ ID NO:21:

```
Leu Lys Leu Xaa Leu Xaa Pro Leu Lys Leu Lys Leu Xaa Pro
1               5                   10
```

(2) INFORMATION FOR SEQ ID NO:22:

(i) SEQUENCE CHARACTERISTICS:
        (A) LENGTH: 14 amino acids
        (B) TYPE: amino acid
        (C) STRANDEDNESS:
        (D) TOPOLOGY: cyclic (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 4
        (D) OTHER INFORMATION: /note= "Residue is a D-Lysine"

(ix) FEATURE:
        (A) NAME/KEY: Modified-site
        (B) LOCATION: 6
        (D) OTHER INFORMATION: /note= "Residue is a D-Phenylalanine"

(ix) FEATURE:
        (A) NAME/KEY: Modified-site
        (B) LOCATION: 13
        (D) OTHER INFORMATION: /note= "Residue is a D-Phenylalanine"

(xi) SEQUENCE DESCRIPTION: SEQ ID NO:22:

```
Val Lys Leu Xaa Val Xaa Pro Leu Lys Val Lys Leu Xaa Pro
1               5                   10
```

(2) INFORMATION FOR SEQ ID NO:23:

(i) SEQUENCE CHARACTERISTICS:
        (A) LENGTH: 14 amino acids
        (B) TYPE: amino acid
        (C) STRANDEDNESS:
        (D) TOPOLOGY: cyclic (ii) MOLECULE TYPE: peptide

```
       (iii) HYPOTHETICAL: NO (iv) ANTI-SENSE: NO (ix) FEATURE:
             (A) NAME/KEY: Modified-site
             (B) LOCATION: 4
             (D) OTHER INFORMATION: /note= "Residue is a D-Lysine"

(ix) FEATURE:
             (A) NAME/KEY: Modified-site
             (B) LOCATION: 6
             (D) OTHER INFORMATION: /note= "Residue is a D-Phenylalanine"

(ix) FEATURE:
             (A) NAME/KEY: Modified-site
             (B) LOCATION: 13
             (D) OTHER INFORMATION: /note= "Residue is a D-Phenylalanine"

(xi) SEQUENCE DESCRIPTION: SEQ ID NO:23:

Leu Lys Leu Xaa Leu Xaa Pro Leu Lys Leu Lys Leu Xaa Pro
 1               5                  10

(2) INFORMATION FOR SEQ ID NO:24:

(i) SEQUENCE CHARACTERISTICS:
             (A) LENGTH: 14 amino acids
             (B) TYPE: amino acid
             (C) STRANDEDNESS:
             (D) TOPOLOGY: linear (ii) MOLECULE TYPE: cyclic (iii) HYPOTHETICAL: NO (iv) ANTI-SENSE: NO (ix) FEATURE:
             (A) NAME/KEY: Modified-site
             (B) LOCATION: 6
             (D) OTHER INFORMATION: /note= "Residue is a D-Tyrosine"

(ix) FEATURE:
             (A) NAME/KEY: Modified-site
             (B) LOCATION: 13
             (D) OTHER INFORMATION: /note= "Residue is a D-Tyrosine"

(xi) SEQUENCE DESCRIPTION: SEQ ID NO:24:

Val Lys Leu Val Lys Xaa Pro Leu Lys Val Leu Lys Xaa Pro
 1               5                  10

(2) INFORMATION FOR SEQ ID NO:25:

(i) SEQUENCE CHARACTERISTICS:
             (A) LENGTH: 14 amino acids
             (B) TYPE: amino acid
             (C) STRANDEDNESS:
             (D) TOPOLOGY: cyclic (ii) MOLECULE TYPE: peptide (iii) HYPOTHETICAL: NO (iv) ANTI-SENSE: NO (ix) FEATURE:
             (A) NAME/KEY: Modified-site
             (B) LOCATION: 6
             (D) OTHER INFORMATION: /note= "Residue is a D-Tyrosine"

(ix) FEATURE:
             (A) NAME/KEY: Modified-site
             (B) LOCATION: 13
             (D) OTHER INFORMATION: /note= "Residue is a D-Tyrosine"
```

(xi) SEQUENCE DESCRIPTION: SEQ ID NO:25:

Leu Val Leu Lys Lys Xaa Pro Lys Lys Val Leu Val Xaa Pro
1               5                   10

(2) INFORMATION FOR SEQ ID NO:26:

(i) SEQUENCE CHARACTERISTICS:
            (A) LENGTH: 14 amino acids
            (B) TYPE: amino acid
            (C) STRANDEDNESS:
            (D) TOPOLOGY: cyclic (ii) MOLECULE TYPE: peptide (iii) HYPOTHETICAL: NO (iv) ANTI-SENSE: NO (ix) FEATURE:
            (A) NAME/KEY: Modified-site
            (B) LOCATION: 6
            (D) OTHER INFORMATION: /note= "Residue is a D-Tyrosine"

(ix) FEATURE:
            (A) NAME/KEY: Modified-site
            (B) LOCATION: 13
            (D) OTHER INFORMATION: /note= "Residue is a D-Tyrosine"

(xi) SEQUENCE DESCRIPTION: SEQ ID NO:26:

Lys Val Lys Leu Lys Xaa Pro Lys Val Lys Leu Lys Xaa Pro
1               5                   10

(2) INFORMATION FOR SEQ ID NO:27:

(i) SEQUENCE CHARACTERISTICS:
            (A) LENGTH: 14 amino acids
            (B) TYPE: amino acid
            (C) STRANDEDNESS:
            (D) TOPOLOGY: cyclic (ii) MOLECULE TYPE: peptide (iii) HYPOTHETICAL: NO (iv) ANTI-SENSE: NO (ix) FEATURE:
            (A) NAME/KEY: Modified-site
            (B) LOCATION: 1
            (D) OTHER INFORMATION: /note= "Residue is a D-Lysine"

(ix) FEATURE:
            (A) NAME/KEY: Modified-site
            (B) LOCATION: 6
            (D) OTHER INFORMATION: /note= "Residue is a D-Tyrosine"

(ix) FEATURE:
            (A) NAME/KEY: Modified-site
            (B) LOCATION: 13
            (D) OTHER INFORMATION: /note= "Residue is a D-Tyrosine"

(xi) SEQUENCE DESCRIPTION: SEQ ID NO:27:

Xaa Val Lys Leu Lys Xaa Pro Lys Val Lys Leu Lys Xaa Pro
1               5                   10

(2) INFORMATION FOR SEQ ID NO:28:

(i) SEQUENCE CHARACTERISTICS:
            (A) LENGTH: 14 amino acids
            (B) TYPE: amino acid
            (C) STRANDEDNESS:
            (D) TOPOLOGY: cyclic

```
        (ii) MOLECULE TYPE: peptide (iii) HYPOTHETICAL: NO (iv) ANTI-SENSE: NO (ix) FEATURE:
             (A) NAME/KEY: Modified-site
             (B) LOCATION: 2
             (D) OTHER INFORMATION: /note= "Residue is a D-Valine"

(ix) FEATURE:
             (A) NAME/KEY: Modified-site
             (B) LOCATION: 6
             (D) OTHER INFORMATION: /note= "Residue is a D-Tyrosine"

(ix) FEATURE:
             (A) NAME/KEY: Modified-site
             (B) LOCATION: 13
             (D) OTHER INFORMATION: /note= "Residue is a D-Tyrosine"

(xi) SEQUENCE DESCRIPTION: SEQ ID NO:28:

Lys Xaa Lys Leu Lys Xaa Pro Lys Val Lys Leu Lys Xaa Pro
1               5                   10

(2) INFORMATION FOR SEQ ID NO:29:

(i) SEQUENCE CHARACTERISTICS:
             (A) LENGTH: 12 amino acids
             (B) TYPE: amino acid
             (C) STRANDEDNESS:
             (D) TOPOLOGY: cyclic (ii) MOLECULE TYPE: peptide (iii) HYPOTHETICAL: NO (iv) ANTI-SENSE: NO (ix) FEATURE:
             (A) NAME/KEY: Modified-site
             (B) LOCATION: 1
             (D) OTHER INFORMATION: /note= "Residue is a D-Tyrosine"

(ix) FEATURE:
             (A) NAME/KEY: Modified-site
             (B) LOCATION: 7
             (D) OTHER INFORMATION: /note= "Residue is a D-Tyrosine"

(xi) SEQUENCE DESCRIPTION: SEQ ID NO:29:

Xaa Pro Val Lys Leu Lys Xaa Pro Lys Val Lys Leu
1               5                   10

(2) INFORMATION FOR SEQ ID NO:30:

(i) SEQUENCE CHARACTERISTICS:
             (A) LENGTH: 12 amino acids
             (B) TYPE: amino acid
             (C) STRANDEDNESS:
             (D) TOPOLOGY: cyclic (ii) MOLECULE TYPE: peptide (iii) HYPOTHETICAL: NO (iv) ANTI-SENSE: NO (ix) FEATURE:
             (A) NAME/KEY: Modified-site
             (B) LOCATION: 1
             (D) OTHER INFORMATION: /note= "Residue is a D-Tyrosine"
```

```
    (ix) FEATURE:
         (A) NAME/KEY: Modified-site
         (B) LOCATION: 7
         (D) OTHER INFORMATION: /note= "Residue is a D-Tyrosine"

(xi) SEQUENCE DESCRIPTION: SEQ ID NO:30:

Xaa Pro Leu Lys Val Lys Xaa Pro Lys Leu Lys Val
1               5                  10

(2) INFORMATION FOR SEQ ID NO:31:

(i) SEQUENCE CHARACTERISTICS:
         (A) LENGTH: 12 amino acids
         (B) TYPE: amino acid
         (C) STRANDEDNESS:
         (D) TOPOLOGY: cyclic (ii) MOLECULE TYPE: peptide (iii) HYPOTHETICAL: NO (iv) ANTI-SENSE: NO (ix) FEATURE:
         (A) NAME/KEY: Modified-site
         (B) LOCATION: 1
         (D) OTHER INFORMATION: /note= "Residue is a D-Phenylalanine"

(ix) FEATURE:
         (A) NAME/KEY: Modified-site
         (B) LOCATION: 7
         (D) OTHER INFORMATION: /note= "Residue is a D-Phenylalanine"

(xi) SEQUENCE DESCRIPTION: SEQ ID NO:31:

Xaa Pro Val Lys Leu Lys Xaa Pro Lys Val Lys Leu
1               5                  10

(2) INFORMATION FOR SEQ ID NO:32:

(i) SEQUENCE CHARACTERISTICS:
         (A) LENGTH: 12 amino acids
         (B) TYPE: amino acid
         (C) STRANDEDNESS:
         (D) TOPOLOGY: cyclic (ii) MOLECULE TYPE: peptide (iii) HYPOTHETICAL: NO (iv) ANTI-SENSE: NO (ix) FEATURE:
         (A) NAME/KEY: Modified-site
         (B) LOCATION: 1
         (D) OTHER INFORMATION: /note= "Residue is a D-Phenylalanine"

(ix) FEATURE:
         (A) NAME/KEY: Modified-site
         (B) LOCATION: 4
         (D) OTHER INFORMATION: /product= "Orn"

(ix) FEATURE:
         (A) NAME/KEY: Modified-site
         (B) LOCATION: 6
         (D) OTHER INFORMATION: /product= "Orn"

(ix) FEATURE:
         (A) NAME/KEY: Modified-site
         (B) LOCATION: 7
         (D) OTHER INFORMATION: /note= "Residue is a D-Phenylalanine"

(ix) FEATURE:
         (A) NAME/KEY: Modified-site
         (B) LOCATION: 9
         (D) OTHER INFORMATION: /product= "Orn"
```

```
    (ix) FEATURE:
        (A) NAME/KEY: Modified-site
        (B) LOCATION: 11
        (D) OTHER INFORMATION: /product= "Orn"

(xi) SEQUENCE DESCRIPTION: SEQ ID NO:32:

Xaa Pro Val Xaa Leu Xaa Xaa Pro Xaa Val Xaa Leu
1               5                   10

(2) INFORMATION FOR SEQ ID NO:33:

(i) SEQUENCE CHARACTERISTICS:
        (A) LENGTH: 12 amino acids
        (B) TYPE: amino acid
        (C) STRANDEDNESS:
        (D) TOPOLOGY: cyclic (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 1
        (D) OTHER INFORMATION: /note= "Residue is a D-Phenylalanine"

(ix) FEATURE:
        (A) NAME/KEY: Modified-site
        (B) LOCATION: 4
        (D) OTHER INFORMATION: /product= "Orn"

(ix) FEATURE:
        (A) NAME/KEY: Modified-site
        (B) LOCATION: 6
        (D) OTHER INFORMATION: /product= "Orn"

(ix) FEATURE:
        (A) NAME/KEY: Modified-site
        (B) LOCATION: 7
        (D) OTHER INFORMATION: /note= "Residue is a D-Phenylalanine"

(ix) FEATURE:
        (A) NAME/KEY: Modified-site
        (B) LOCATION: 9
        (D) OTHER INFORMATION: /product= "Orn"

(ix) FEATURE:
        (A) NAME/KEY: Modified-site
        (B) LOCATION: 11
        (D) OTHER INFORMATION: /product= "Orn"

(xi) SEQUENCE DESCRIPTION: SEQ ID NO:33:

Xaa Pro Leu Xaa Leu Xaa Xaa Pro Xaa Leu Xaa Leu
1               5                   10

(2) INFORMATION FOR SEQ ID NO:34:

(i) SEQUENCE CHARACTERISTICS:
        (A) LENGTH: 10 amino acids
        (B) TYPE: amino acid
        (C) STRANDEDNESS:
        (D) TOPOLOGY: cyclic (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 2
        (D) OTHER INFORMATION: /product= "Orn"
```

```
    (ix) FEATURE:
         (A) NAME/KEY: Modified-site
         (B) LOCATION: 4
         (D) OTHER INFORMATION: /note= "Residue is a D-Phenylalanine"

(ix) FEATURE:
         (A) NAME/KEY: Modified-site
         (B) LOCATION: 7
         (D) OTHER INFORMATION: /product= "Orn"

(ix) FEATURE:
         (A) NAME/KEY: Modified-site
         (B) LOCATION: 9
         (D) OTHER INFORMATION: /note= "Residue is a D-Phenylalanine"

(xi) SEQUENCE DESCRIPTION: SEQ ID NO:34:

Val Xaa Leu Phe Pro Val Xaa Leu Phe Pro
1               5                   10

(2) INFORMATION FOR SEQ ID NO:35:

(i) SEQUENCE CHARACTERISTICS:
        (A) LENGTH: 14 amino acids
        (B) TYPE: amino acid
        (C) STRANDEDNESS:
        (D) TOPOLOGY: cyclic (ii) MOLECULE TYPE: peptide (ix) FEATURE:
         (A) NAME/KEY: Modified-site
         (B) LOCATION: 1
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 2
         (D) OTHER INFORMATION: /note= "Xaa = Lys, Arg, His, Orn, Dbu,
             Dpr"

(ix) FEATURE:
         (A) NAME/KEY: Modified-site
         (B) LOCATION: 3
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 4
         (D) OTHER INFORMATION: /note= "Xaa = Lys, Arg, His, Orn, Dbu,
             Dpr"

(ix) FEATURE:
         (A) NAME/KEY: Modified-site
         (B) LOCATION: 5
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 6
         (D) OTHER INFORMATION: /note= "Xaa = D-amino acid selected
             from the group Ala, Val, Leu, Nva, Ile, Nle, Met, Phe,
             Tyr, Trp"

(ix) FEATURE:
         (A) NAME/KEY: Modified-site
         (B) LOCATION: 8
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 9
         (D) OTHER INFORMATION: /note= "Xaa = Lys, Arg, His, Orn, Dbu,
             Dpr"
```

```
     (ix) FEATURE:
          (A) NAME/KEY: Modified-site
          (B) LOCATION: 10
          (D) OTHER INFORMATION: /note= "Xaa = Ala, Val, Leu, Nva, Ile,
              Nle Met Phe, Tyr or Trp"

(ix) FEATURE:
          (A) NAME/KEY: Modified-site
          (B) LOCATION: 11
          (D) OTHER INFORMATION: /note= "Xaa = Lys, Arg, His, Orn, Dbu,
              Dpr"

(ix) FEATURE:
          (A) NAME/KEY: Modified-site
          (B) LOCATION: 12
          (D) OTHER INFORMATION: /note= "Xaa = Ala, Val, Leu, Nva, Ile,
              Nle Met Phe, Tyr or Trp"

(ix) FEATURE:
          (A) NAME/KEY: Modified-site
          (B) LOCATION: 13
          (D) OTHER INFORMATION: /note= "Xaa = D-amino acid selected
              from the group Ala, Val, Leu, Nva, Ile, Nle, Met, Phe,
              Tyr, Trp"

(xi) SEQUENCE DESCRIPTION: SEQ ID NO:35:

Xaa Xaa Xaa Xaa Xaa Xaa Pro Xaa Xaa Xaa Xaa Xaa Xaa Pro
1               5                   10

(2) INFORMATION FOR SEQ ID NO:36:

(i) SEQUENCE CHARACTERISTICS:
          (A) LENGTH: 18 amino acids
          (B) TYPE: amino acid
          (C) STRANDEDNESS:
          (D) TOPOLOGY: cyclic (ii) MOLECULE TYPE: peptide (ix) FEATURE:
          (A) NAME/KEY: Modified-site
          (B) LOCATION: 1
          (D) OTHER INFORMATION: /note= "Xaa = Ala, Val, Leu, Nva, Ile,
              Nle Met Phe, Tyr or Trp"

(ix) FEATURE:
          (A) NAME/KEY: Modified-site
          (B) LOCATION: 2
          (D) OTHER INFORMATION: /note= "Xaa = Lys, Arg, His, Orn,
              Dbu, Dpr"

(ix) FEATURE:
          (A) NAME/KEY: Modified-site
          (B) LOCATION: 3
          (D) OTHER INFORMATION: /note= "Xaa = Ala, Val, Leu, Nva, Ile,
              Nle Met Phe, Tyr or Trp"

(ix) FEATURE:
          (A) NAME/KEY: Modified-site
          (B) LOCATION: 4
          (D) OTHER INFORMATION: /note= "Xaa = Lys, Arg, His, Orn,
              Dbu, Dpr"

(ix) FEATURE:
          (A) NAME/KEY: Modified-site
          (B) LOCATION: 5
          (D) OTHER INFORMATION: /note= "Xaa = Ala, Val, Leu, Nva, Ile,
              Nle Met Phe, Tyr or Trp"

(ix) FEATURE:
          (A) NAME/KEY: Modified-site
          (B) LOCATION: 6
          (D) OTHER INFORMATION: /note= "Xaa = Lys, Arg, His, Orn, Dbu,
              Dpr"
```

```
    (ix) FEATURE:
         (A) NAME/KEY: Modified-site
         (B) LOCATION: 7
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 8
         (D) OTHER INFORMATION: /note= "Xaa = D-amino acid selected
             from the group Ala, Val, Leu, Nva, Ile, Met, Phe, Tyr,
             Trp"

(ix) FEATURE:
         (A) NAME/KEY: Modified-site
         (B) LOCATION: 10
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 11
         (D) OTHER INFORMATION: /note= "Xaa = Lys, Arg, His, Orn, Dbu,
             Dpr"

(ix) FEATURE:
         (A) NAME/KEY: Modified-site
         (B) LOCATION: 12
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 13
         (D) OTHER INFORMATION: /note= "Xaa = Lys, Arg, His, Orn, Dbu,
             Dpr"

(ix) FEATURE:
         (A) NAME/KEY: Modified-site
         (B) LOCATION: 14
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 15
         (D) OTHER INFORMATION: /note= "Xaa = Lys, Arg, His, Orn, Dbu,
             Dpr"

(ix) FEATURE:
         (A) NAME/KEY: Modified-site
         (B) LOCATION: 16
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 17
         (D) OTHER INFORMATION: /note= "Xaa = D-amino acid selected
             from the group Ala, Val, Leu, Nva, Ile, Nle, Met, Phe,
             Tyr, Trp"

(xi) SEQUENCE DESCRIPTION: SEQ ID NO:36:

Xaa Xaa Xaa Xaa Xaa Xaa Xaa Xaa Pro Xaa Xaa Xaa Xaa Xaa Xaa Xaa
1               5                   10                  15

Xaa Pro (2) INFORMATION FOR SEQ ID NO:37:

(i) SEQUENCE CHARACTERISTICS:
        (A) LENGTH: 22 amino acids
        (B) TYPE: amino acid
        (C) STRANDEDNESS:
        (D) TOPOLOGY: cyclic (ii) MOLECULE TYPE: peptide
```

```
(ix) FEATURE:
    (A) NAME/KEY: Modified-site
    (B) LOCATION: 1
    (D) OTHER INFORMATION: /note= "Xaa = Ala, Val, Leu, Nva, Ile,
        Nle Met Phe, Tyr or Trp"

(ix) FEATURE:
    (A) NAME/KEY: Modified-site
    (B) LOCATION: 2
    (D) OTHER INFORMATION: /note= "Xaa = Lys, Arg, His, Orn, Dbu,
        Dpr"

(ix) FEATURE:
    (A) NAME/KEY: Modified-site
    (B) LOCATION: 3
    (D) OTHER INFORMATION: /note= "Xaa = Ala, Val, Leu, Nva, Ile,
        Nle Met Phe, Tyr or Trp"

(ix) FEATURE:
    (A) NAME/KEY: Modified-site
    (B) LOCATION: 4
    (D) OTHER INFORMATION: /note= "Xaa = Lys, Arg, His, Orn, Dbu,
        Dpr"

(ix) FEATURE:
    (A) NAME/KEY: Modified-site
    (B) LOCATION: 5
    (D) OTHER INFORMATION: /note= "Xaa = Ala, Val, Leu, Nva, Ile,
        Nle Met Phe, Tyr or Trp"

(ix) FEATURE:
    (A) NAME/KEY: Modified-site
    (B) LOCATION: 6
    (D) OTHER INFORMATION: /note= "Xaa = Lys, Arg, His, Orn, Dbu,
        Dpr"

(ix) FEATURE:
    (A) NAME/KEY: Modified-site
    (B) LOCATION: 7
    (D) OTHER INFORMATION: /note= "Xaa = Ala, Val, Leu, Nva, Ile,
        Nle Met Phe, Tyr or Trp"

(ix) FEATURE:
    (A) NAME/KEY: Modified-site
    (B) LOCATION: 8
    (D) OTHER INFORMATION: /note= "Xaa = Lys, Arg, His, Orn, Dbu,
        Dpr"

(ix) FEATURE:
    (A) NAME/KEY: Modified-site
    (B) LOCATION: 9
    (D) OTHER INFORMATION: /note= "Xaa = Ala, Val, Leu, Nva, Ile,
        Nle Met Phe, Tyr or Trp"

(ix) FEATURE:
    (A) NAME/KEY: Modified-site
    (B) LOCATION: 10
    (D) OTHER INFORMATION: /note= "Xaa = D-amino acid selected
        from the group Ala, Val, Leu, Nva, Ile, Nle, Met, Phe,
        tyr, Trp"

(ix) FEATURE:
    (A) NAME/KEY: Modified-site
    (B) LOCATION: 12
    (D) OTHER INFORMATION: /note= "Xaa = Ala, Val, Leu, Nva, Ile,
        Nle Met Phe, Tyr or Trp"

(ix) FEATURE:
    (A) NAME/KEY: Modified-site
    (B) LOCATION: 13
    (D) OTHER INFORMATION: /note= "Xaa = Lys, Arg, His, Orn, Dbu,
        Dpr"

(ix) FEATURE:
    (A) NAME/KEY: Modified-site
    (B) LOCATION: 14
    (D) OTHER INFORMATION: /note= "Xaa = Ala, Val, Leu, Nva, Ile,
        Nle Met Phe, Tyr or Trp"
```

```
      (ix) FEATURE:
            (A) NAME/KEY: Modified-site
            (B) LOCATION: 15
            (D) OTHER INFORMATION: /note= "Xaa = Lys, Arg, His, Orn, Dbu,
                Dpr"

(ix) FEATURE:
            (A) NAME/KEY: Modified-site
            (B) LOCATION: 16
            (D) OTHER INFORMATION: /note= "Xaa = Ala, Val, Leu, Nva, Ile,
                Nle Met Phe, Tyr or Trp"

(ix) FEATURE:
            (A) NAME/KEY: Modified-site
            (B) LOCATION: 17
            (D) OTHER INFORMATION: /note= "Xaa = Lys, Arg, His, Orn, Dbu,
                Dpr"

(ix) FEATURE:
            (A) NAME/KEY: Modified-site
            (B) LOCATION: 18
            (D) OTHER INFORMATION: /note= "Xaa = Ala, Val, Leu, Nva, Ile,
                Nle Met Phe, Tyr or Trp"

(ix) FEATURE:
            (A) NAME/KEY: Modified-site
            (B) LOCATION: 19
            (D) OTHER INFORMATION: /note= "Xaa = Lys, Arg, His, Orn, Dbu,
                Dpr"

(ix) FEATURE:
            (A) NAME/KEY: Modified-site
            (B) LOCATION: 20
            (D) OTHER INFORMATION: /note= "Xaa = Ala, Val, Leu, Nva, Ile,
                Nle Met Phe, Tyr or Trp"

(ix) FEATURE:
            (A) NAME/KEY: Modified-site
            (B) LOCATION: 21
            (D) OTHER INFORMATION: /note= "Xaa = D-amino acid selected
                from the group Ala, Val, Leu, Nva, Ile, Nle, Met, Phe,
                Tyr, Trp"

(xi) SEQUENCE DESCRIPTION: SEQ ID NO:37:

Xaa Xaa Xaa Xaa Xaa Xaa Xaa Xaa Xaa Xaa Pro Xaa Xaa Xaa Xaa Xaa
 1               5                  10                  15

Xaa Xaa Xaa Xaa Xaa Pro
            20

(2) INFORMATION FOR SEQ ID NO:38:

(i) SEQUENCE CHARACTERISTICS:
            (A) LENGTH: 26 amino acids
            (B) TYPE: amino acid
            (C) STRANDEDNESS:
            (D) TOPOLOGY: cyclic (ii) MOLECULE TYPE: peptide (ix) FEATURE:
            (A) NAME/KEY: Modified-site
            (B) LOCATION: 1
            (D) OTHER INFORMATION: /note= "Xaa = Ala, Val, Leu, Nva, Ile,
                Nle Met Phe, Tyr or Trp"

(ix) FEATURE:
            (A) NAME/KEY: Modified-site
            (B) LOCATION: 2
            (D) OTHER INFORMATION: /note= "Xaa = Lys, Arg, His, Orn, Dbu,
                Dpr"

(ix) FEATURE:
            (A) NAME/KEY: Modified-site
            (B) LOCATION: 3
            (D) OTHER INFORMATION: /note= "Xaa = Ala, Val, Leu, Nva, Ile,
                Nle Met Phe, Tyr or Trp"
```

```
(ix) FEATURE:
    (A) NAME/KEY: Modified-site
    (B) LOCATION: 4
    (D) OTHER INFORMATION: /note= "Xaa = Lys, Arg, His, Orn, Dbu,
        Dpr"

(ix) FEATURE:
    (A) NAME/KEY: Modified-site
    (B) LOCATION: 5
    (D) OTHER INFORMATION: /note= "Xaa = Ala, Val, Leu, Nva, Ile,
        Nle Met Phe, Tyr or Trp"

(ix) FEATURE:
    (A) NAME/KEY: Modified-site
    (B) LOCATION: 6
    (D) OTHER INFORMATION: /note= "Xaa = Lys, Arg, His, Orn, Dbu,
        Dpr"

(ix) FEATURE:
    (A) NAME/KEY: Modified-site
    (B) LOCATION: 7
    (D) OTHER INFORMATION: /note= "Xaa = Ala, Val, Leu, Nva, Ile,
        Nle Met Phe, Tyr or Trp"

(ix) FEATURE:
    (A) NAME/KEY: Modified-site
    (B) LOCATION: 8
    (D) OTHER INFORMATION: /note= "Xaa = Lys, Arg, His, Orn, Dbu,
        Dpr"

(ix) FEATURE:
    (A) NAME/KEY: Modified-site
    (B) LOCATION: 9
    (D) OTHER INFORMATION: /note= "Xaa = Ala, Val, Leu, Nva, Ile,
        Nle Met Phe, Tyr or Trp"

(ix) FEATURE:
    (A) NAME/KEY: Modified-site
    (B) LOCATION: 10
    (D) OTHER INFORMATION: /note= "Xaa = Lys, Arg, His, Orn, Dbu,
        Dpr"

(ix) FEATURE:
    (A) NAME/KEY: Modified-site
    (B) LOCATION: 11
    (D) OTHER INFORMATION: /note= "Xaa = Ala, Val, Leu, Nva, Ile,
        Nle Met Phe, Tyr or Trp"

(ix) FEATURE:
    (A) NAME/KEY: Modified-site
    (B) LOCATION: 12
    (D) OTHER INFORMATION: /note= "Xaa = D-amino acid selected
        from the group Ala, Val , Leu, Nva, Ile, Nle, Met, Phe,
        Tyr, Trp"

(ix) FEATURE:
    (A) NAME/KEY: Modified-site
    (B) LOCATION: 14
    (D) OTHER INFORMATION: /note= "Xaa = Ala, Val, Leu, Nva, Ile,
        Nle Met Phe, Tyr or Trp"

(ix) FEATURE:
    (A) NAME/KEY: Modified-site
    (B) LOCATION: 15
    (D) OTHER INFORMATION: /note= "Xaa = Lys, Arg, His, Orn, Dbu,
        Dpr"

(ix) FEATURE:
    (A) NAME/KEY: Modified-site
    (B) LOCATION: 16
    (D) OTHER INFORMATION: /note= "Xaa = Ala, Val, Leu, Nva, Ile,
        Nle Met Phe, Tyr or Trp"

(ix) FEATURE:
    (A) NAME/KEY: Modified-site
    (B) LOCATION: 17
    (D) OTHER INFORMATION: /note= "Xaa = Lys, Arg, His, Orn, Dbu,
        Dpr"
```

```
    (ix) FEATURE:
         (A) NAME/KEY: Modified-site
         (B) LOCATION: 18
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 19
         (D) OTHER INFORMATION: /note= "Xaa = Lys, Arg, His, Orn, Dbu,
             Dpr"

(ix) FEATURE:
         (A) NAME/KEY: Modified-site
         (B) LOCATION: 20
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 21
         (D) OTHER INFORMATION: /note= "Xaa = Lys, Arg, His, Orn, Dbu,
             Dpr"

(ix) FEATURE:
         (A) NAME/KEY: Modified-site
         (B) LOCATION: 22
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 23
         (D) OTHER INFORMATION: /note= "Xaa = Lys, Arg, His, Orn, Dbu,
             Dpr"

(ix) FEATURE:
         (A) NAME/KEY: Modified-site
         (B) LOCATION: 24
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 25
         (D) OTHER INFORMATION: /note= "Xaa = D-amino acid selected
             from the group Ala, Val, Leu, Nva, Ile, Nle, Met, Phe,
             Tyr, Trp"

(xi) SEQUENCE DESCRIPTION: SEQ ID NO:38:

Xaa Xaa Xaa Xaa Xaa Xaa Xaa Xaa Xaa Xaa Xaa Xaa Pro Xaa Xaa Xaa
1               5                   10                  15

Xaa Xaa Xaa Xaa Xaa Xaa Xaa Xaa Xaa Pro
            20                  25

(2) INFORMATION FOR SEQ ID NO:39:

(i) SEQUENCE CHARACTERISTICS:
         (A) LENGTH: 12 amino acids
         (B) TYPE: amino acid
         (C) STRANDEDNESS:
         (D) TOPOLOGY: cyclic (ii) MOLECULE TYPE: peptide (ix) FEATURE:
         (A) NAME/KEY: Modified-site
         (B) LOCATION: 1
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 2
         (D) OTHER INFORMATION: /note= "Xaa = Lys, Arg, His, Orn, Dbu,
             Dpr"
```

```
    (ix) FEATURE:
         (A) NAME/KEY: Modified-site
         (B) LOCATION: 3
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 4
         (D) OTHER INFORMATION: /note= "Xaa = Lys, Arg, His, Orn, Dbu,
             Dpr"

(ix) FEATURE:
         (A) NAME/KEY: Modified-site
         (B) LOCATION: 5
         (D) OTHER INFORMATION: /note= "Xaa = D-amino acid selected
             from the group Ala, Val, Leu, Nva, Ile, Nle, Met, Phe,
             Tyr, Trp"

(ix) FEATURE:
         (A) NAME/KEY: Modified-site
         (B) LOCATION: 7
         (D) OTHER INFORMATION: /note= "Xaa = Lys, Arg, His, Orn, Dbu,
             Dpr"

(ix) FEATURE:
         (A) NAME/KEY: Modified-site
         (B) LOCATION: 8
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 9
         (D) OTHER INFORMATION: /note= "Xaa = Lys, Arg, His, Orn, Dbu,
             Dpr"

(ix) FEATURE:
         (A) NAME/KEY: Modified-site
         (B) LOCATION: 10
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 11
         (D) OTHER INFORMATION: /note= "Xaa = D-amino acid selected
             from the group Ala, Val, Leu, Nva, Ile, Nle, Met, Phe,
             Tyr, Trp"

(xi) SEQUENCE DESCRIPTION: SEQ ID NO:39:

Xaa Xaa Xaa Xaa Xaa Pro Xaa Xaa Xaa Xaa Xaa Pro
1               5                   10

(2) INFORMATION FOR SEQ ID NO:40:

(i) SEQUENCE CHARACTERISTICS:
         (A) LENGTH: 16 amino acids
         (B) TYPE: amino acid
         (C) STRANDEDNESS:
         (D) TOPOLOGY: cyclic (ii) MOLECULE TYPE: peptide (ix) FEATURE:
         (A) NAME/KEY: Modified-site
         (B) LOCATION: 1
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 2
         (D) OTHER INFORMATION: /note= "Xaa = Lys, Arg, His, Orn, Dbu,
             Dpr"
```

```
    (ix) FEATURE:
         (A) NAME/KEY: Modified-site
         (B) LOCATION: 3
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 4
         (D) OTHER INFORMATION: /note= "Xaa = Lys, Arg, His, Orn, Dbu,
             Dpr"

(ix) FEATURE:
         (A) NAME/KEY: Modified-site
         (B) LOCATION: 5
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 6
         (D) OTHER INFORMATION: /note= "Xaa = Lys, Arg, His, Orn, Dbu,
             Dpr"

(ix) FEATURE:
         (A) NAME/KEY: Modified-site
         (B) LOCATION: 7
         (D) OTHER INFORMATION: /note= "Xaa = D-amino acid selected
             from the group Ala, Val, Leu, Nva, Ile, Nle, Met, Phe,
             Tyr, Trp"

(ix) FEATURE:
         (A) NAME/KEY: Modified-site
         (B) LOCATION: 9
         (D) OTHER INFORMATION: /note= "Xaa = Lys, Arg, His, Orn, Dbu,
             Dpr"

(ix) FEATURE:
         (A) NAME/KEY: Modified-site
         (B) LOCATION: 10
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 11
         (D) OTHER INFORMATION: /note= "Xaa = Lys, Arg, His, Orn, Dbu,
             Dpr"

(ix) FEATURE:
         (A) NAME/KEY: Modified-site
         (B) LOCATION: 12
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 13
         (D) OTHER INFORMATION: /note= "Xaa = Lys, Arg, His, Orn, Dbu,
             Dpr"

(ix) FEATURE:
         (A) NAME/KEY: Modified-site
         (B) LOCATION: 14
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 15
         (D) OTHER INFORMATION: /note= "Xaa = D-amino acid selected
             from the group Ala, Val, Leu, Nva, Ile, Nle, Met, Phe,
             Tyr Trp"

(xi) SEQUENCE DESCRIPTION: SEQ ID NO:40:

Xaa Xaa Xaa Xaa Xaa Xaa Xaa Pro Xaa Xaa Xaa Xaa Xaa Xaa Xaa Pro
1               5                   10                  15
```

(2) INFORMATION FOR SEQ ID NO:41:

(i) SEQUENCE CHARACTERISTICS:
        (A) LENGTH: 20 amino acids
        (B) TYPE: amino acid
        (C) STRANDEDNESS:
        (D) TOPOLOGY: cyclic (ii) MOLECULE TYPE: peptide (ix) FEATURE:
        (A) NAME/KEY: Modified-site
        (B) LOCATION: 1
        (D) OTHER INFORMATION: /note= "Xaa = Ala, Val, Leu, Nva, Ile,
           Nle Met Phe, Tyr or Trp"

(ix) FEATURE:
        (A) NAME/KEY: Modified-site
        (B) LOCATION: 2
        (D) OTHER INFORMATION: /note= "Xaa = Lys, Arg, His, Orn, Dbu,
           Dpr"

(ix) FEATURE:
        (A) NAME/KEY: Modified-site
        (B) LOCATION: 3
        (D) OTHER INFORMATION: /note= "Xaa = Ala, Val, Leu, Nva, Ile,
           Nle Met Phe, Tyr or Trp"

(ix) FEATURE:
        (A) NAME/KEY: Modified-site
        (B) LOCATION: 4
        (D) OTHER INFORMATION: /note= "Xaa = Lys, Arg, His, Orn, Dbu,
           Dpr"

(ix) FEATURE:
        (A) NAME/KEY: Modified-site
        (B) LOCATION: 5
        (D) OTHER INFORMATION: /note= "Xaa = Ala, Val, Leu, Nva, Ile,
           Nle Met Phe, Tyr or Trp"

(ix) FEATURE:
        (A) NAME/KEY: Modified-site
        (B) LOCATION: 6
        (D) OTHER INFORMATION: /note= "Xaa = Lys, Arg, His, Orn, Dbu,
           Dpr"

(ix) FEATURE:
        (A) NAME/KEY: Modified-site
        (B) LOCATION: 7
        (D) OTHER INFORMATION: /note= "Xaa = Ala, Val, Leu, Nva, Ile,
           Nle Met Phe, Tyr or Trp"

(ix) FEATURE:
        (A) NAME/KEY: Modified-site
        (B) LOCATION: 8
        (D) OTHER INFORMATION: /note= "Xaa = Lys, Arg, His, Orn, Dbu,
           Dpr"

(ix) FEATURE:
        (A) NAME/KEY: Modified-site
        (B) LOCATION: 9
        (D) OTHER INFORMATION: /note= "Xaa = D-amino acid selected
           from the group Ala, Val Leu, Nva, Ile, Nle, Met, Phe,
           Tyr Trp"

(ix) FEATURE:
        (A) NAME/KEY: Modified-site
        (B) LOCATION: 11
        (D) OTHER INFORMATION: /note= "Xaa = Lys, Arg, His, Orn, Dbu,
           Dpr"

(ix) FEATURE:
        (A) NAME/KEY: Modified-site
        (B) LOCATION: 12
        (D) OTHER INFORMATION: /note= "Xaa = Ala, Val, Leu, Nva, Ile,
           Nle Met Phe, Tyr or Trp"

```
    (ix) FEATURE:
         (A) NAME/KEY: Modified-site
         (B) LOCATION: 13
         (D) OTHER INFORMATION: /note= "Xaa = Lys, Arg, His, Orn, Dbu,
             Dpr"

(ix) FEATURE:
         (A) NAME/KEY: Modified-site
         (B) LOCATION: 14
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 15
         (D) OTHER INFORMATION: /note= "Xaa = Lys, Arg, His, Orn, Dbu,
             Dpr"

(ix) FEATURE:
         (A) NAME/KEY: Modified-site
         (B) LOCATION: 16
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 17
         (D) OTHER INFORMATION: /note= "Xaa = Lys, Arg, His, Orn, Dbu,
             Dpr"

(ix) FEATURE:
         (A) NAME/KEY: Modified-site
         (B) LOCATION: 18
         (D) OTHER INFORMATION: /note= "Xaa = Ala, Val, Leu, Nva, Ile,
             Nle Met Phe, Tyr or Trp (ix) FEATURE:
         (A) NAME/KEY: Modified-site
         (B) LOCATION: 19
         (D) OTHER INFORMATION: /note= "Xaa = D-amino acid selected
             from the group Ala, Val, Leu, Nva, Ile, Nle, Met, Phe,
             Tyr, Trp"

(xi) SEQUENCE DESCRIPTION: SEQ ID NO:41:

Xaa Xaa Xaa Xaa Xaa Xaa Xaa Xaa Xaa Pro Xaa Xaa Xaa Xaa Xaa Xaa
1               5                   10                  15

Xaa Xaa Xaa Pro
            20

(2) INFORMATION FOR SEQ ID NO:42:

(i) SEQUENCE CHARACTERISTICS:
         (A) LENGTH: 24 amino acids
         (B) TYPE: amino acid
         (C) STRANDEDNESS:
         (D) TOPOLOGY: cyclic (ii) MOLECULE TYPE: peptide (ix) FEATURE:
         (A) NAME/KEY: Modified-site
         (B) LOCATION: 1
         (D) OTHER INFORMATION: /note= "Xaa = Ala, Val, Leu, Nva, Ile,
             Nle Met Phe, Tyr or Trp"

(ix) FEATURE:
         (A) NAME/KEY: Modified-site
         (B) LOCATION: 2
         (D) OTHER INFORMATION: /note= "Xaa = Lys, Arg, His, Orn, Dbu,
             Dpr"

(ix) FEATURE:
         (A) NAME/KEY: Modified-site
         (B) LOCATION: 3
         (D) OTHER INFORMATION: /note= "Xaa = Ala, Val, Leu, Nva, Ile,
             Nle Met Phe, Tyr or Trp"
```

```
(ix) FEATURE:
    (A) NAME/KEY: Modified-site
    (B) LOCATION: 4
    (D) OTHER INFORMATION: /note= "Xaa = Lys, Arg, His, Orn, Dbu,
        Dpr"

(ix) FEATURE:
    (A) NAME/KEY: Modified-site
    (B) LOCATION: 5
    (D) OTHER INFORMATION: /note= "Xaa = Ala, Val, Leu, Nva, Ile,
        Nle Met Phe, Tyr or Trp"

(ix) FEATURE:
    (A) NAME/KEY: Modified-site
    (B) LOCATION: 6
    (D) OTHER INFORMATION: /note= "Xaa = Lys, Arg, His, Orn, Dbu,
        Dpr"

(ix) FEATURE:
    (A) NAME/KEY: Modified-site
    (B) LOCATION: 7
    (D) OTHER INFORMATION: /note= "Xaa = Ala, Val, Leu, Nva, Ile,
        Nle Met Phe, Tyr or Trp"

(ix) FEATURE:
    (A) NAME/KEY: Modified-site
    (B) LOCATION: 8
    (D) OTHER INFORMATION: /note= "Xaa = Lys, Arg, His, Orn, Dbu,
        Dpr"

(ix) FEATURE:
    (A) NAME/KEY: Modified-site
    (B) LOCATION: 9
    (D) OTHER INFORMATION: /note= "Xaa = Ala, Val, Leu, Nva, Ile,
        Nle Met Phe, Tyr or Trp"

(ix) FEATURE:
    (A) NAME/KEY: Modified-site
    (B) LOCATION: 10
    (D) OTHER INFORMATION: /note= "Xaa = Lys, Arg, His, Orn, Dbu,
        Dpr"

(ix) FEATURE:
    (A) NAME/KEY: Modified-site
    (B) LOCATION: 11
    (D) OTHER INFORMATION: /note= "Xaa = D-amino acid selected
        from the group Ala, Val, Leu, Nva, Ile, Nle, Met, Phe,
        Tyr Trp"

(ix) FEATURE:
    (A) NAME/KEY: Modified-site
    (B) LOCATION: 13
    (D) OTHER INFORMATION: /note= "Xaa = Lys, Arg, His, Orn, Dbu,
        Dpr"

(ix) FEATURE:
    (A) NAME/KEY: Modified-site
    (B) LOCATION: 14
    (D) OTHER INFORMATION: /note= "Xaa = Ala, Val, Leu, Nva, Ile,
        Nle Met Phe, Tyr or Trp"

(ix) FEATURE:
    (A) NAME/KEY: Modified-site
    (B) LOCATION: 15
    (D) OTHER INFORMATION: /note= "Xaa = Lys, Arg, His, Orn, Dbu,
        Dpr"

(ix) FEATURE:
    (A) NAME/KEY: Modified-site
    (B) LOCATION: 16
    (D) OTHER INFORMATION: /note= "Xaa = Ala, Val, Leu, Nva, Ile,
        Nle Met Phe, Tyr or Trp"

(ix) FEATURE:
    (A) NAME/KEY: Modified-site
    (B) LOCATION: 17
    (D) OTHER INFORMATION: /note= "Xaa = Lys, Arg, His, Orn, Dbu,
        Dpr"
```

```
        (ix) FEATURE:
              (A) NAME/KEY: Modified-site
              (B) LOCATION: 18
              (D) OTHER INFORMATION: /note= "Xaa = Ala, Val, Leu, Nva, Ile,
                  Nle Met Phe, Tyr or Trp"

(ix) FEATURE:
              (A) NAME/KEY: Modified-site
              (B) LOCATION: 19
              (D) OTHER INFORMATION: /note= "Xaa = Lys, Arg, His, Orn, Dbu,
                  Dpr"

(ix) FEATURE:
              (A) NAME/KEY: Modified-site
              (B) LOCATION: 20
              (D) OTHER INFORMATION: /note= "Xaa = Ala, Val, Leu, Nva, Ile,
                  Nle Met Phe, Tyr or Trp"

(ix) FEATURE:
              (A) NAME/KEY: Modified-site
              (B) LOCATION: 21
              (D) OTHER INFORMATION: /note= "Xaa = Lys, Arg, His, Orn, Dbu,
                  Dpr"

(ix) FEATURE:
              (A) NAME/KEY: Modified-site
              (B) LOCATION: 22
              (D) OTHER INFORMATION: /note= "Xaa = Ala, Val, Leu, Nva, Ile,
                  Nle Met Phe, Tyr or Trp"

(ix) FEATURE:
              (A) NAME/KEY: Modified-site
              (B) LOCATION: 23
              (D) OTHER INFORMATION: /note= "Xaa = D-amino acid selected
                  from the group Ala, Val, Leu, Nva, Ile, Nle, Met, Phe,
                  Tyr Trp"

(xi) SEQUENCE DESCRIPTION: SEQ ID NO:42:

Xaa Xaa Xaa Xaa Xaa Xaa Xaa Xaa Xaa Xaa Xaa Pro Xaa Xaa Xaa Xaa
1               5                   10                  15

Xaa Xaa Xaa Xaa Xaa Xaa Xaa Pro
            20
```